(12) United States Patent
Nishikawa

(10) Patent No.: US 7,439,332 B2
(45) Date of Patent: Oct. 21, 2008

(54) POLYPEPTIDE HAVING AN ACTIVITY TO SUPPORT PROLIFERATION OR SURVIVAL OF HEMATOPOIETIC STEM OR PROGENITOR CELLS

(75) Inventor: Mitsuo Nishikawa, Gunma (JP)

(73) Assignee: Kirin Pharma Kabushiki Kaisha, Tokyo-To (JP)

( * ) Notice: Subject to any disclaimer, the term of this patent is extended or adjusted under 35 U.S.C. 154(b) by 206 days.

(21) Appl. No.: 10/512,109

(22) PCT Filed: Apr. 25, 2003

(86) PCT No.: PCT/JP03/05383

§ 371 (c)(1),
(2), (4) Date: Jul. 21, 2005

(87) PCT Pub. No.: WO03/091280

PCT Pub. Date: Nov. 6, 2003

(65) Prior Publication Data

US 2005/0255546 A1 Nov. 17, 2005

Related U.S. Application Data

(60) Provisional application No. 60/376,001, filed on Apr. 26, 2002.

(51) Int. Cl.
*C07K 14/475* (2006.01)
*C07H 21/04* (2006.01)

(52) U.S. Cl. ..................... 530/399; 530/350; 536/23.5

(58) Field of Classification Search ....................... None
See application file for complete search history.

(56) References Cited

U.S. PATENT DOCUMENTS

| 5,350,836 A | * | 9/1994 | Kopchick et al. | ............ 530/399 |
| 2003/0022217 A1 | * | 1/2003 | Ceccardi et al. | ................. 435/6 |

FOREIGN PATENT DOCUMENTS

| EP | 0 953 354 A1 | 11/1999 |
| WO | WO 99 03980 A1 | 1/1999 |
| WO | WO 02 060942 A2 | 8/2002 |
| WO | WO 02 070539 A3 | 9/2002 |
| WO | WO 02 100898 A2 | 12/2002 |

OTHER PUBLICATIONS

Kapur et al. The presence of novel amino acids in the cytoplasmic domain of stem cell factor results in hematopoietic defects in Steel17H mice. Blood 94(6): 1915-1925, 1999.*
Sher et al. Mutations uncouple human fibroblast growth factor (FGF)-7 biological activity and receptor binding and support broad specificity in the secondary receptor binding site of FGFs. J Biol Chem 274(49): 35016-35022, 1999.*
Wuyts et al. NH2- and COOH-terminal truncations of murine granulocyte chemotactic protein-2 augment the in vitro and in vivo neutrophil chemotactic potency. J Immunol 163: 6155-6163, 1999.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells, J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Wognum et al. Identification and isolation of hematopoietic stem cells. Arch Med Res 34: 461-475, 2003.*
Quesenberry et al. "Hematopoietic stem cells, progenitor cells, and cytokines", pp. 153-174, Williams Hematology, Sixth Edition, New York: McGraw-Hill, 2001.*
Database WPI, Section Ch, Week 199911 Derwent Publications, AN 1999-13227, Abstract for WO 9903980, Database Accession No. 1999-132227, Jan. 28, 1999 (XP002248950), 2 pages.
Database EMBL 'Online!, the sequences from Adachi, J. et al., "Mus musculus adult male hippocampus cDNA, RIKEN full-length enriched library clone:C630007L04 product:hypothetical Thrombospondin type 1 repeat (TSP1) profile/Thrombospondin type I domain/Furin-like cystein rich region containing protein, full insert sequence," Database Accession No. AK049891, (XP002248970), 3 pages, Mar. 1, 2003.
Database EMBL 'Online!, the sequences from Strausberg, R.L. et al., "Homo sapiens hypothetical protein MGC35555, mRNA (cDNA clone MGC:35555 Image:5201681), complete cds," Database Accession No. BC027938, (XP002248948), 3 pages, May 15, 2003.
Database GenSeq 'Online!, the sequences from Tang, Y.T. et al., "Human polypeptide Seq ID No. 1165," Database Accession No. ABP69118, Jan. 20, 2003 (XP002248949), 1 page.
Drmanac, S. et al., "Accurate sequencing by hybridization for DNA diagnostics and individual genomics," Nature Biotechnology, vol. 16, Jan. 1998 (XP001064848), pp. 54-58.
Moore, K.A. et al., "Hermatopoietic activity of a stromal cell transmembrane protein containing epidermal growth factor-like repeat motifs," Proc. Natl. Acad. Sci. USA, vol. 94, Apr. 1997 (XP002943669), pp. 4011-4016.
Moore, K.A. et al., "In Vitro Maintainance of Highly Purified, Transplatable Hematopoietic Stem Cells," Blood, vol. 98, No. 12, Jun. 15, 1997 (XP002220989), pp. 4337-4347.
Xu, M. et al. "Stimulation of Human Primitive Hematopoiesis by Murine AGM-Derived Stromal Cells," Blood, vol. 90, No. 10, Nov. 15, 1997 (XP002911189), p. 483A.

* cited by examiner

*Primary Examiner*—Bridget E Bunner
(74) *Attorney, Agent, or Firm*—Stephen A. Bent; Richard B. McCaslin; Foley & Lardner LLP

(57) ABSTRACT

A gene encoding a polypeptide having an activity to support proliferation or survival of hematopoietic stem cells or hematopoietic progenitor cells is isolated by comparing expressed genes between cells which support proliferation or survival of hematopoietic stem cells or hematopoietic progenitor cells and cells which do not support the proliferation or survival. Proliferation or survival of hematopoietic stem cells or hematopoietic progenitor cells is supported by using stromal cells in which the isolated gene is expressed or a gene product of the isolated gene.

4 Claims, 10 Drawing Sheets

SEQUENCE LISTING

```
<160> NUMBER OF SEQ ID NOS: 49

<210> SEQ ID NO 1
<211> LENGTH: 343
<212> TYPE: DNA
<213> ORGANISM: Mus musculus

<400> SEQUENCE: 1
cctatggcgg caacgacgtg gacttccagg atgctagtga tgacggcagt ggctccggca       60
gcggtggcgg atgcccagat gacacctgtg gccggagggt cagcaagaag agttccagct      120
cccggacccc cttgacccat gccctcccg gcctgtcaga acaggaggga cagaagacct       180
cagctgccac ctgcccagag ccccacagct tcttcctgct cttcctcgtc accttggtcc      240
ttgcggcagc caggcccagg tggcggtaac tgcccctat cccagacagt aactctgagt      300
gctgcggcag ggtgcatgga ggggtccctc cctccttgag tcg                         343
```

<210> SEQ ID NO 2
<211> LENGTH: 546
<212> TYPE: DNA
<213> ORGANISM: Mus musculus

<400> SEQUENCE: 2

```
tgtacccag ggacttcctg atcctcttac atgtataaat agcaagaccg ggccaggaac     60
agcaagcagt ctgaaggcca gctgggtctg cccactaaga agatgaagcc ttttcatact    120
gccctctcct tcctcattct tacaactgct cttggaatct gggcccagat cacacatgca    180
acagagacaa agaagtcca gagcagtctg aaggcacagc aagggcttga aattgaaatg     240
tttcacatgg gctttcaaga ctcttcagat tgctgcctgt cctataactc acggattcag    300
tgttcaagat ttataggtta ttttcccacc agtggtgggt gtaccaggcc gggcatcatc    360
tttatcagca agagggggtt ccaggtctgt gccaacccca gtgatcggag agttcagaga    420
tgcattgaaa gattggagca aaactcacaa ccacggacct acaaacaata acatttgctt    480
gaagagaagg gtgtgaactg ccagctactt tctttggtct tccccagtga ccacctaagt    540
ggctct                                                               546
```

<210> SEQ ID NO 3
<211> LENGTH: 1223
<212> TYPE: DNA
<213> ORGANISM: Mus musculus

<400> SEQUENCE: 3

```
gtgacccgga agggagcccc gtggtagagg tgaccggagc tgagcatttc agatctgctt     60
agtaaaccgg tgtatcgccc accatgttgg ctgcaaggct tgtgtgtctc cggacactac    120
cttccagggt tttccagccc actttcatca ccaaggcctc tccacttgtg aagaattcca    180
tcacaaagaa ccaatggctc gtaacaccca gcagggaata tgctaccaag acaagaatta    240
ggactcaccg tgggaaaact ggacaagaac tgaaagaggc agccttggaa ccatcaatgg    300
aaaaaatctt taaaatcgat caaatgggaa ggtggtttgt tgctggagga gcagctgttg    360
gtcttggagc gctctgctac tatggcttgg gaatgtctaa tgagattgga gctatcgaaa    420
aggctgtaat ttggcctcag tatgtaaagg atagaattca ttctacttac atgtacttag    480
caggaaggta ttgtttaaca gctttgtctg ccttggcagt agccagaaca cctgctctca    540
tgaacttcat gatgacaggc tcttgggtga caattggtgc gacctttgca gccatgattg    600
gagctggaat gcttgtacac tcaatatcat atgagcagag cccaggccca aagcatctgg    660
cttggatgct gcattctggt gtgatgggtg cagttgtggc tcctctgacg atcttagggg    720
ggcctcttct cctgagagcc gcatggtaca ccgctggtat tgtgggaggc ctctctactg    780
tggccatgtg tgcgcctagt gagaagtttc tgaacatggg agcaccctg ggagtgggcc    840
tgggtcttgt ctttgcgtct ctctgggggt ctatgtttct tccccctacc tctgtggctg    900
gtgccactct gtactcagtg gcaatgtatg gtggattagt tcttttcagc atgttccttc    960
tgtatgatac tcagaaagta atcaaacgtg cagaaataac acccatgtat ggagctcaaa   1020
agtatgatcc catcaattcg atgttgacaa tctacatgga tacattaaat atatttatgc   1080
gagttgcaac tatgctagca actggaagca acagaaagaa atgaagtaac cgcttgtgat   1140
gtctccgctc actgatgtct tgcttgttta ataggagcag atagtcatta cagtttgcat   1200
cagcagaatt cccgcgcggc cgc                                           1223
```

```
<210> SEQ ID NO 4
<211> LENGTH: 839
<212> TYPE: DNA
<213> ORGANISM: Mus musculus

<400> SEQUENCE: 4
gctgtgcctg gcatcagtct tgccctctcc cctttggcca cgcggcccctt ctcagcgatt      60 tgcagcagac ccgcagggca gtgtgcctcg gtggcattga actgaagctt ggctctcggc     120
ctggcctgct ggctagttgc ccaccctgtg ggtcccgccc agagcaagga tactggagct     180
ttcgcctgcc tcactgagcc tgggtctcca ctccagtcat ccctccagct actttgcagc     240
actctgtcgc catgagcacc tcgtctgcgc ggcctgcagt cctggcccctt gccgggctgg     300 ctctgctcct tctgctgtgc ctgggtccag atggcataag tggaaacaaa ctcaagaaga     360
tgctccagaa acgagaagga cctgtcccgt caaagactaa tgtagctgta gccgagaaca     420
cagcaaagga attcctaggt ggcctgaagc gtgccaaacg acagctgtgg gaccgtacgc     480
ggcctgaggt acagcagtgg taccagcagt tcctctacat gggctttgat gaggctaaat     540
ttgaagatga tgtcaactat tggctaaaca gaaatcgaaa cggccatgac tactatggtg     600
actactacca gcgtcattat gatgaagatg cggccattgg tccccacagc cgggaaagct     660
tcaggcatgg agccagtgtg aactatgatg actattaagc ttcctgaggt gcccacagag     720
cttgtgcctg cttcagtagg cctctctac ctataccacg tgaccatcag gctaaggaa      780 agaatataag tgcttttgc atttcatgca tgtgcttaac gatatgtctc acttaaaaa      839

<210> SEQ ID NO 5
<211> LENGTH: 1420
<212> TYPE: DNA
<213> ORGANISM: Mus musculus

<400> SEQUENCE: 5
cctgtgccta ttttgatgga tggcaatgct aagcaagcaa gcactgttca cttgtgactt      60
tcatttctca cactgtgcac tgtcaaagac aaatgtgcat ggaaaaatgt ttagtgtcac     120
ctcatggcgt tctcagcatc agtgaccttc aaacggtcct acaatgagac tgtgttctag     180
ctaggggtat gctgtggaaa ttcctgctac atttcatctt agtgctaaca tgtacagatt     240
ctgctgcgct acattcaaag ctcattactg tatatttatg ctttctctgt gtaacaagtt     300
atacctgata agatgtcact ttgtttctag tgattcttaa ccatggtctg gtacatggct     360
attctagttt tggaaattaa caagtgtttt gttgcctctt gttttctttt gttcctatca     420
tttttggcgg gggttgggtg ggcttgattc taaccgtaag tataggataa gctagttttg     480
tatatagagt caaatgactg atgtcagagg atcagtgctg atagaacttc cccagttcat     540
gtcacgatac acacagagag aaagcagcat gaggcatctt gccatcagaa gccaaatttc     600
ttttgagtcc caaaattgat gacttatgaa atatagctga aaacaagatt tgggtgtagt     660
tacttgtatt tattatacaa tttccaatta catttttttt caaactcaaa ataacccatg     720
actttgagtg ataggtcact tggcaatgtt cttgaattac tggggaagct gttgtcacta     780
agataatgag agagaaaata gaatggcttc gcccaagtga gagccacatc ttacatttct     840
ctgttgaatc ggaatcaact atattagaac agaagcctga tagaagcttt ctagttaaca     900
cacacaaggc catggtttca aaacatctt tgtccccta ggtcagtttg tccttagatt     960
atgaattggc aggttctaat tgcattattt ccctggctga tccaggaaaa agttagaaca    1020
aaataagttg catagttttg aggaaacatc caaagcaagg cgaagccttt ccttgccttg    1080
```

-continued

```
cattggcaaa actacctctt tagcatttat gttgattcag aaacatcttg ctgatatgtg    1140
tagatgtttt aagcttcatt gtgaaaatat tgatgcaaga taagccatat atgaatgttg    1200
tattcaactt tagggcttga aattaatcct aaagtgttca cctctctcca tgtctattta    1260
cactctgttc ctatttacta agagggtagg ggtctcctta atatcatact tcattgttaa    1320
taagtcaatg cttgttatgt ttcttggctg ttgttttgt gcattaaaaa ctcaaaattg     1380
gaaaaaaaaa aaaaaaaaaa aaaaaaaaaa aaaaaaaaa                          1420
```

<210> SEQ ID NO 6
<211> LENGTH: 763
<212> TYPE: DNA
<213> ORGANISM: Mus musculus

<400> SEQUENCE: 6

```
cccgccctcg cgaccccggc tctcctggac tcggcgccgc caacctgggc gatgccccgc      60
tacgagttgg ctttgattct gaaagccatg cggcggccag agaccgctgc tgctttgaaa     120
cgtacaatag aatccctgat ggaccgagga gccatagtga ggaacttgga aagcctgggt     180
gagcgtgcgc tcccctacag gatctcgagt cacagccagc agcacagccg aggagggtat     240
ttcctggtgg attttatgc tccgacaagt gctgtggaga acatactgga acacttggcg      300
cgagacattg acgtggttag accaaatatt gtgaaacacc ctctgaccca ggaagtaaaa     360
gagtgtgacg gcatagtccc agtcccactt gaagaaaaac tgtattcaac aaagaggagg    420
aagaagtgag aagattcacc agattctggc cttatattta atcctaaggg cactatgggt     480
gctgctaggt tgttgtctag gatactttag cccatgacca ttttgctgca ggaggtagaa     540
actgctggcc gagacctgcc ctgatgtctc tgctgagatt tcatcccact tgtgggttt      600 gtcgggagtg ggggtgttca cagtaccact gtagcgtttc caagagcaaa atgtttgtca    660
ttcacacttg gttgtcttgc aagcctatat ggaacactgg gagcagagta ataaacatga    720
ctttatcaac actggaaaaa aaaaaaaaaa aaaaaaaaa aaa                       763
```

<210> SEQ ID NO 7
<211> LENGTH: 1300
<212> TYPE: DNA
<213> ORGANISM: Mus musculus

<400> SEQUENCE: 7

```
ggtatgcagt cttccgcttg aatttgctgt tgtttatat agtaataaca gcgctatcta      60
taaggcttac tggccttatt cctggttcca taagacacag gctgtacccc tttactgaat    120
ggcatgggct cagcttggag gaaagtcaga ggaaattcag ataacttggt atctcttcct    180
gtcgttgcaa tgtttcgggg tccacttcac tatgagatac caagcagctg ccaacctcac    240
catactcatt tcgttacaat ttctgaggca ccgtggtgac ttgatccgac atacgaccac    300
gtcagttaca aaccagatct ttatggttaa cttttgaaca tttcacaaac aacattgtaa    360
atgtgcgatg ttatgtttta aatcagacca cagtggtccc caaatattat gtacatatga    420
caaatgtcag tgtaactttt tgttacactg acagtttcat aggtaaacaa acctacgctc    480
caatgttaaa ttatgcttgt gtatgtaaaa tacacaagca ttgggctatg tgtgtacgga    540
catgagggta gtgcaatcgt actgtacgaa atgggtcaga atcattttca gtggtgttag    600
gttatgtagt ttcagactcc atgctgcatt ttctcttgca catgccatcc atttgcttat    660
tttggagtgt gagtattcct tcttattaat ttgaattcaa agcacaagcc tcccattgtt    720
caacattacc caacaagagt gtccagtgat gaccgagtta tctcacctgc tatacttta    780
```

-continued

```
ctgcaataat taatgacacc tggatgagga ggcgtgcgct gacttcattg ttcacccggg      840
atagtgcatg agcccactga attagagctg cttctaccag caaaagtgag cagtacacat      900
aggtgcatgt ttgaaacatg aatcacatag agctatggag ttttgccaag tgatgtgttt      960 tcttttctt ttttctttt tttcttttt cttctttttt ttcctttct tcttcttctt          1020 cttttttttt ttttttacta tgcaaagatg ggaaatgcac aaacttccaa gacatgtctg      1080
aagaacttta caatacttga atttttcttt taatcatccc atcacattta tggcattgat      1140
gcttccattg tattttcttt ttgtccctc aacttcaatg gtttgtaatt tcaatgcaca       1200
acctaacttt tgtttgcagt aacttccaat cctattggct gcctggaacg agattctgt       1260 catcctacac gcatctttta gttgactgtg cataaaagtt                            1300
```

<210> SEQ ID NO 8
<211> LENGTH: 1674
<212> TYPE: DNA
<213> ORGANISM: Mus musculus
<220> FEATURE:
<221> NAME/KEY: CDS
<222> LOCATION: (1)..(1671)

<400> SEQUENCE: 8

```
atg gaa ctc cgg acc cga ggc tgg tgg ctg ctg tgc gcg gcc gcc gcg      48
Met Glu Leu Arg Thr Arg Gly Trp Trp Leu Leu Cys Ala Ala Ala Ala
1               5                   10                  15 ctg gtc gtc tgc gcc cgc ggg gac ccc gcc agc aag agc cgg agc tgc      96
Leu Val Val Cys Ala Arg Gly Asp Pro Ala Ser Lys Ser Arg Ser Cys
            20                  25                  30 agc gaa gtc cgc cag atc tac ggg gct aag ggc ttt agc ctg agc gat     144
Ser Glu Val Arg Gln Ile Tyr Gly Ala Lys Gly Phe Ser Leu Ser Asp
        35                  40                  45 gtg ccc cag gca gag atc tcg ggt gag cac ctg cgg atc tgc ccc cag     192
Val Pro Gln Ala Glu Ile Ser Gly Glu His Leu Arg Ile Cys Pro Gln
    50                  55                  60 ggc tac act tgc tgt acc agt gag atg gag gag aat ttg gcc aac cac     240
Gly Tyr Thr Cys Cys Thr Ser Glu Met Glu Glu Asn Leu Ala Asn His
65                  70                  75                  80 agc cga atg gag ctg gag agc gca ctc cat gac agc agc cgc gcc ctg     288
Ser Arg Met Glu Leu Glu Ser Ala Leu His Asp Ser Ser Arg Ala Leu
                85                  90                  95 cag gcc aca ctg gcc acc cag ctg cat ggc atc gat gac cac ttc cag     336
Gln Ala Thr Leu Ala Thr Gln Leu His Gly Ile Asp Asp His Phe Gln
            100                 105                 110 cgc ctg ctg aat gac tcg gag cgc aca ctg cag gag gct ttc cct ggg     384
Arg Leu Leu Asn Asp Ser Glu Arg Thr Leu Gln Glu Ala Phe Pro Gly
        115                 120                 125 gcc ttt ggg gac ctg tat acg cag aac act cgt gcc ttc cgg gac cta     432
Ala Phe Gly Asp Leu Tyr Thr Gln Asn Thr Arg Ala Phe Arg Asp Leu
    130                 135                 140 tat gtt gag ctg cgc ctc tac tac cgt ggg gcc aac ctg cac ctt gag     480
Tyr Val Glu Leu Arg Leu Tyr Tyr Arg Gly Ala Asn Leu His Leu Glu
145                 150                 155                 160 gag acg ctg gcc gag ttc tgg gca cgg ctg ctg gag cgc ctc ttc aag     528
Glu Thr Leu Ala Glu Phe Trp Ala Arg Leu Leu Glu Arg Leu Phe Lys
                165                 170                 175 cag ctg cac ccc cag ctg ctg cct gat gac tac ctg gac tgc ctg ggc     576
Gln Leu His Pro Gln Leu Leu Pro Asp Asp Tyr Leu Asp Cys Leu Gly
            180                 185                 190
```

```
aag cag gcg gag gca ctg cgg ccg ttt gga gat gcc cct cga gaa ctg      624
Lys Gln Ala Glu Ala Leu Arg Pro Phe Gly Asp Ala Pro Arg Glu Leu
        195                 200                 205 cgc ctg cgg gcc acc cgt gcc ttt gtg gct gca cgt tcc ttt gtg cag      672
Arg Leu Arg Ala Thr Arg Ala Phe Val Ala Ala Arg Ser Phe Val Gln
    210                 215                 220 ggc ctg ggt gtg gcc agt gat gta gtc cgg aag gtg gcc cag gta cct      720
Gly Leu Gly Val Ala Ser Asp Val Val Arg Lys Val Ala Gln Val Pro
225                 230                 235                 240 ctg gcc cca gaa tgt tct cgg gcc atc atg aag ttg gtc tac tgt gct      768
Leu Ala Pro Glu Cys Ser Arg Ala Ile Met Lys Leu Val Tyr Cys Ala
                245                 250                 255 cat tgc cgg gga gtc ccg ggc gcc cgg ccc tgc ccc gac tat tgc cga      816
His Cys Arg Gly Val Pro Gly Ala Arg Pro Cys Pro Asp Tyr Cys Arg
            260                 265                 270 aat gtg ctc aaa ggc tgc ctt gcc aac cag gcc gac ctg gat gcc gag      864
Asn Val Leu Lys Gly Cys Leu Ala Asn Gln Ala Asp Leu Asp Ala Glu
        275                 280                 285 tgg agg aac ctc ctg gac tcc atg gtg ctc atc act gac aag ttc tgg      912
Trp Arg Asn Leu Leu Asp Ser Met Val Leu Ile Thr Asp Lys Phe Trp
    290                 295                 300 ggc ccg tcg ggt gcg gag agt gtc att ggc ggt gtg cac gtg tgg ctg      960
Gly Pro Ser Gly Ala Glu Ser Val Ile Gly Gly Val His Val Trp Leu
305                 310                 315                 320 gcg gag gcc atc aac gcc ctc cag gac aac aag gac aca ctc aca gct     1008
Ala Glu Ala Ile Asn Ala Leu Gln Asp Asn Lys Asp Thr Leu Thr Ala
                325                 330                 335 aag gtc atc cag gcc tgt gga aac ccc aag gtc aat ccc cac ggc tct     1056
Lys Val Ile Gln Ala Cys Gly Asn Pro Lys Val Asn Pro His Gly Ser
            340                 345                 350 ggg ccc gag gag aag cgt cgc cgt ggc aaa ttg gca ctg cag gag aag     1104
Gly Pro Glu Glu Lys Arg Arg Arg Gly Lys Leu Ala Leu Gln Glu Lys
        355                 360                 365 ccc tcc aca ggt act ctg gaa aaa ctg gtc tct gag gcc aag gcc cag     1152
Pro Ser Thr Gly Thr Leu Glu Lys Leu Val Ser Glu Ala Lys Ala Gln
    370                 375                 380 ctc cga gac att cag gac ttc tgg atc agc ctc cca ggg aca ctg tgc     1200
Leu Arg Asp Ile Gln Asp Phe Trp Ile Ser Leu Pro Gly Thr Leu Cys
385                 390                 395                 400 agt gag aag atg gcc atg agt cct gcc agt gat gac cgc tgc tgg aat     1248
Ser Glu Lys Met Ala Met Ser Pro Ala Ser Asp Asp Arg Cys Trp Asn
                405                 410                 415 gga att tcc aag ggc cgg tac cta cca gag gtg atg ggt gac ggg ctg     1296
Gly Ile Ser Lys Gly Arg Tyr Leu Pro Glu Val Met Gly Asp Gly Leu
            420                 425                 430 gcc aac cag atc aac aac cct gag gtg gaa gtg gac atc acc aag cca     1344
Ala Asn Gln Ile Asn Asn Pro Glu Val Glu Val Asp Ile Thr Lys Pro
        435                 440                 445 gac atg acc atc cgc cag cag att atg cag ctc aag atc atg acc aac     1392
Asp Met Thr Ile Arg Gln Gln Ile Met Gln Leu Lys Ile Met Thr Asn
    450                 455                 460 cgt tta cgt ggc gcc tat ggc ggc aac gac gtg gac ttc cag gat gct     1440
Arg Leu Arg Gly Ala Tyr Gly Gly Asn Asp Val Asp Phe Gln Asp Ala
465                 470                 475                 480 agt gat gac ggc agt ggc tcc ggc agc ggt ggc gga tgc cca gat gac     1488
Ser Asp Asp Gly Ser Gly Ser Gly Ser Gly Gly Gly Cys Pro Asp Asp
                485                 490                 495 acc tgt ggc cgg agg gtc agc aag aag agt tcc agc tcc cgg acc ccc     1536
Thr Cys Gly Arg Arg Val Ser Lys Lys Ser Ser Ser Ser Arg Thr Pro
            500                 505                 510
```

```
ttg acc cat gcc ctc ccc ggc ctg tca gaa cag gag gga cag aag acc    1584
Leu Thr His Ala Leu Pro Gly Leu Ser Glu Gln Glu Gly Gln Lys Thr
        515                 520                 525 tca gct gcc acc tgc cca gag ccc cac agc ttc ttc ctg ctc ttc ctc    1632
Ser Ala Ala Thr Cys Pro Glu Pro His Ser Phe Phe Leu Leu Phe Leu
530                 535                 540 gtc acc ttg gtc ctt gcg gca gcc agg ccc agg tgg cgg taa             1674
Val Thr Leu Val Leu Ala Ala Ala Arg Pro Arg Trp Arg
545                 550                 555

<210> SEQ ID NO 9
<211> LENGTH: 557
<212> TYPE: PRT
<213> ORGANISM: Mus musculus

<400> SEQUENCE: 9

Met Glu Leu Arg Thr Arg Gly Trp Trp Leu Leu Cys Ala Ala Ala
1               5                   10                  15

Leu Val Val Cys Ala Arg Gly Asp Pro Ala Ser Lys Ser Arg Ser Cys
                20                  25                  30

Ser Glu Val Arg Gln Ile Tyr Gly Ala Lys Gly Phe Ser Leu Ser Asp
            35                  40                  45

Val Pro Gln Ala Glu Ile Ser Gly Glu His Leu Arg Ile Cys Pro Gln
        50                  55                  60

Gly Tyr Thr Cys Cys Thr Ser Glu Met Glu Glu Asn Leu Ala Asn His
65                  70                  75                  80

Ser Arg Met Glu Leu Glu Ser Ala Leu His Asp Ser Ser Arg Ala Leu
                85                  90                  95

Gln Ala Thr Leu Ala Thr Gln Leu His Gly Ile Asp Asp His Phe Gln
            100                 105                 110

Arg Leu Leu Asn Asp Ser Glu Arg Thr Leu Gln Glu Ala Phe Pro Gly
        115                 120                 125

Ala Phe Gly Asp Leu Tyr Thr Gln Asn Thr Arg Ala Phe Arg Asp Leu
    130                 135                 140

Tyr Val Glu Leu Arg Leu Tyr Tyr Arg Gly Ala Asn Leu His Leu Glu
145                 150                 155                 160

Glu Thr Leu Ala Glu Phe Trp Ala Arg Leu Leu Glu Arg Leu Phe Lys
                165                 170                 175

Gln Leu His Pro Gln Leu Leu Pro Asp Asp Tyr Leu Asp Cys Leu Gly
            180                 185                 190

Lys Gln Ala Glu Ala Leu Arg Pro Phe Gly Asp Ala Pro Arg Glu Leu
        195                 200                 205

Arg Leu Arg Ala Thr Arg Ala Phe Val Ala Ala Arg Ser Phe Val Gln
    210                 215                 220

Gly Leu Gly Val Ala Ser Asp Val Val Arg Lys Val Ala Gln Val Pro
225                 230                 235                 240

Leu Ala Pro Glu Cys Ser Arg Ala Ile Met Lys Leu Val Tyr Cys Ala
                245                 250                 255

His Cys Arg Gly Val Pro Gly Ala Arg Pro Cys Pro Asp Tyr Cys Arg
            260                 265                 270

Asn Val Leu Lys Gly Cys Leu Ala Asn Gln Ala Asp Leu Asp Ala Glu
        275                 280                 285

Trp Arg Asn Leu Leu Asp Ser Met Val Leu Ile Thr Asp Lys Phe Trp
    290                 295                 300

Gly Pro Ser Gly Ala Glu Ser Val Ile Gly Gly Val His Val Trp Leu
305                 310                 315                 320
```

```
Ala Glu Ala Ile Asn Ala Leu Gln Asp Asn Lys Asp Thr Leu Thr Ala
            325                 330                 335

Lys Val Ile Gln Ala Cys Gly Asn Pro Lys Val Asn Pro His Gly Ser
        340                 345                 350

Gly Pro Glu Glu Lys Arg Arg Gly Lys Leu Ala Leu Gln Glu Lys
    355                 360                 365

Pro Ser Thr Gly Thr Leu Glu Lys Leu Val Ser Glu Ala Lys Ala Gln
    370                 375                 380

Leu Arg Asp Ile Gln Asp Phe Trp Ile Ser Leu Pro Gly Thr Leu Cys
385                 390                 395                 400

Ser Glu Lys Met Ala Met Ser Pro Ala Ser Asp Asp Arg Cys Trp Asn
                405                 410                 415

Gly Ile Ser Lys Gly Arg Tyr Leu Pro Glu Val Met Gly Asp Gly Leu
            420                 425                 430

Ala Asn Gln Ile Asn Asn Pro Glu Val Glu Val Asp Ile Thr Lys Pro
        435                 440                 445

Asp Met Thr Ile Arg Gln Gln Ile Met Gln Leu Lys Ile Met Thr Asn
    450                 455                 460

Arg Leu Arg Gly Ala Tyr Gly Gly Asn Asp Val Asp Phe Gln Asp Ala
465                 470                 475                 480

Ser Asp Asp Gly Ser Gly Ser Gly Gly Gly Cys Pro Asp Asp
                485                 490                 495

Thr Cys Gly Arg Arg Val Ser Lys Lys Ser Ser Ser Arg Thr Pro
            500                 505                 510

Leu Thr His Ala Leu Pro Gly Leu Ser Glu Gln Glu Gly Gln Lys Thr
        515                 520                 525

Ser Ala Ala Thr Cys Pro Glu Pro His Ser Phe Phe Leu Leu Phe Leu
    530                 535                 540

Val Thr Leu Val Leu Ala Ala Ala Arg Pro Arg Trp Arg
545                 550                 555

<210> SEQ ID NO 10
<211> LENGTH: 1677
<212> TYPE: DNA
<213> ORGANISM: Homo sapiens
<220> FEATURE:
<221> NAME/KEY: CDS
<222> LOCATION: (1)..(1674)

<400> SEQUENCE: 10 atg gag ctc cgg gcc cga ggc tgg tgg ctg cta tgt gcg gcc gca gcg      48
Met Glu Leu Arg Ala Arg Gly Trp Trp Leu Leu Cys Ala Ala Ala Ala
1               5                   10                  15 ctg gtc gcc tgc gcc cgc ggg gac ccg gcc agc aag agc cgg agc tgc      96
Leu Val Ala Cys Ala Arg Gly Asp Pro Ala Ser Lys Ser Arg Ser Cys
                20                  25                  30 ggc gag gtc cgc cag atc tac gga gcc aag ggc ttc agc ctg agc gac     144
Gly Glu Val Arg Gln Ile Tyr Gly Ala Lys Gly Phe Ser Leu Ser Asp
            35                  40                  45 gtg ccc cag gcg gag atc tcg ggt gag cac ctg cgg atc tgt ccc cag     192
Val Pro Gln Ala Glu Ile Ser Gly Glu His Leu Arg Ile Cys Pro Gln
        50                  55                  60 ggc tac acc tgc tgc acc agc gag atg gag gag aac ctg gcc aac cgc     240
Gly Tyr Thr Cys Cys Thr Ser Glu Met Glu Glu Asn Leu Ala Asn Arg
65                  70                  75                  80 agc cat gcc gag ctg gag acc gcg ctc cgg gac agc agc cgc gtc ctg     288
Ser His Ala Glu Leu Glu Thr Ala Leu Arg Asp Ser Ser Arg Val Leu
                85                  90                  95
```

-continued

| | |
|---|---|
| cag gcc atg ctt gcc acc cag ctg cgc agc ttc gat gac cac ttc cag<br>Gln Ala Met Leu Ala Thr Gln Leu Arg Ser Phe Asp Asp His Phe Gln<br>       100                  105                  110 | 336 |
| cac ctg ctg aac gac tcg gag cgg acg ctg cag gcc acc ttc ccc ggc<br>His Leu Leu Asn Asp Ser Glu Arg Thr Leu Gln Ala Thr Phe Pro Gly<br>   115                  120                  125 | 384 |
| gcc ttc gga gag ctg tac acg cag aac gcg agg gcc ttc cgg gac ctg<br>Ala Phe Gly Glu Leu Tyr Thr Gln Asn Ala Arg Ala Phe Arg Asp Leu<br>130                  135                  140 | 432 |
| tac tca gag ctg cgc ctg tac tac cgc ggt gcc aac ctg cac ctg gag<br>Tyr Ser Glu Leu Arg Leu Tyr Tyr Arg Gly Ala Asn Leu His Leu Glu<br>145                  150                  155                  160 | 480 |
| gag acg ctg gcc gag ttc tgg gcc cgc ctg ctc gag cgc ctc ttc aag<br>Glu Thr Leu Ala Glu Phe Trp Ala Arg Leu Leu Glu Arg Leu Phe Lys<br>                          165                  170                  175 | 528 |
| cag ctg cac ccc cag ctg ctg cct gat gac tac ctg gac tgc ctg<br>Gln Leu His Pro Gln Leu Leu Pro Asp Asp Tyr Leu Asp Cys Leu<br>                      180                  185                  190 | 576 |
| ggc aag cag gcc gag gcg ctg cgg ccc ttc ggg gag gcc ccg aga gag<br>Gly Lys Gln Ala Glu Ala Leu Arg Pro Phe Gly Glu Ala Pro Arg Glu<br>                  195                  200                  205 | 624 |
| ctg cgc ctg cgg gcc acc cgt gcc ttc gtg gct gct cgc tcc ttt gtg<br>Leu Arg Leu Arg Ala Thr Arg Ala Phe Val Ala Ala Arg Ser Phe Val<br>210                  215                  220 | 672 |
| cag ggc ctg ggc gtg gcc agc gac gtg gtc cgg aaa gtg gct cag gtc<br>Gln Gly Leu Gly Val Ala Ser Asp Val Val Arg Lys Val Ala Gln Val<br>225                  230                  235                  240 | 720 |
| ccc ctg ggc ccg gag tgc tcg aga gct gtc atg aag ctg gtc tac tgt<br>Pro Leu Gly Pro Glu Cys Ser Arg Ala Val Met Lys Leu Val Tyr Cys<br>                          245                  250                  255 | 768 |
| gct cac tgc ctg gga gtc ccc ggc gcc agg ccc tgc cct gac tat tgc<br>Ala His Cys Leu Gly Val Pro Gly Ala Arg Pro Cys Pro Asp Tyr Cys<br>                      260                  265                  270 | 816 |
| cga aat gtg ctc aag ggc tgc ctt gcc aac cag gcc gac ctg gac gcc<br>Arg Asn Val Leu Lys Gly Cys Leu Ala Asn Gln Ala Asp Leu Asp Ala<br>                275                  280                  285 | 864 |
| gag tgg agg aac ctc ctg gac tcc atg gtg ctc atc acc gac aag ttc<br>Glu Trp Arg Asn Leu Leu Asp Ser Met Val Leu Ile Thr Asp Lys Phe<br>290                  295                  300 | 912 |
| tgg ggt aca tcg ggt gtg gag agt gtc atc ggc agc gtg cac acg tgg<br>Trp Gly Thr Ser Gly Val Glu Ser Val Ile Gly Ser Val His Thr Trp<br>305                  310                  315                  320 | 960 |
| ctg gcg gag gcc atc aac gcc ctc cag gac aac agg gac acg ctc acg<br>Leu Ala Glu Ala Ile Asn Ala Leu Gln Asp Asn Arg Asp Thr Leu Thr<br>                          325                  330                  335 | 1008 |
| gcc aag gtc atc cag ggc tgc ggg aac ccc aag gtc aac ccc cag ggc<br>Ala Lys Val Ile Gln Gly Cys Gly Asn Pro Lys Val Asn Pro Gln Gly<br>                      340                  345                  350 | 1056 |
| cct ggg cct gag gag aag cgg cgc cgg ggc aag ctg gcc ccg cgg gag<br>Pro Gly Pro Glu Glu Lys Arg Arg Arg Gly Lys Leu Ala Pro Arg Glu<br>                  355                  360                  365 | 1104 |
| agg cca cct tca ggc acg ctg gag aag ctg gtc tct gaa gcc aag gcc<br>Arg Pro Pro Ser Gly Thr Leu Glu Lys Leu Val Ser Glu Ala Lys Ala<br>370                  375                  380 | 1152 |
| cag ctc cgc gac gtc cag gac ttc tgg atc agc ctc cca ggg aca ctg<br>Gln Leu Arg Asp Val Gln Asp Phe Trp Ile Ser Leu Pro Gly Thr Leu<br>385                  390                  395                  400 | 1200 |
| tgc agt gag aag atg gcc ctg agc act gcc agt gat gac cgc tgc tgg<br>Cys Ser Glu Lys Met Ala Leu Ser Thr Ala Ser Asp Asp Arg Cys Trp<br>                          405                  410                  415 | 1248 |

```
aac ggg atg gcc aga ggc cgg tac ctc ccc gag gtc atg ggt gac ggc    1296
Asn Gly Met Ala Arg Gly Arg Tyr Leu Pro Glu Val Met Gly Asp Gly
            420                 425                 430 ctg gcc aac cag atc aac aac ccc gag gtg gag gtg gac atc acc aag    1344
Leu Ala Asn Gln Ile Asn Asn Pro Glu Val Glu Val Asp Ile Thr Lys
435                 440                 445 ccg gac atg acc atc cgg cag cag atc atg cag ctg aag atc atg acc    1392
Pro Asp Met Thr Ile Arg Gln Gln Ile Met Gln Leu Lys Ile Met Thr
    450                 455                 460 aac cgg ctg cgc agc gcc tac aac ggc aac gac gtg gac ttc cag gac    1440
Asn Arg Leu Arg Ser Ala Tyr Asn Gly Asn Asp Val Asp Phe Gln Asp
465                 470                 475                 480 gcc agt gac gac ggc agc ggc tcg ggc agc ggt gat ggc tgt ctg gat    1488
Ala Ser Asp Asp Gly Ser Gly Ser Gly Ser Gly Asp Gly Cys Leu Asp
                485                 490                 495 gac ctc tgc ggc cgg aag gtc agc agg aag agc tcc agc tcc cgg acg    1536
Asp Leu Cys Gly Arg Lys Val Ser Arg Lys Ser Ser Ser Ser Arg Thr
            500                 505                 510 ccc ttg acc cat gcc ctc cca ggc ctg tca gag cag gaa gga cag aag    1584
Pro Leu Thr His Ala Leu Pro Gly Leu Ser Glu Gln Glu Gly Gln Lys
        515                 520                 525 acc tcg gct gcc agc tgc ccc cag ccc ccg acc ttc ctc ctg ccc ctc    1632
Thr Ser Ala Ala Ser Cys Pro Gln Pro Pro Thr Phe Leu Leu Pro Leu
530                 535                 540 ctc ctc ttc ctg gcc ctt aca gta gcc agg ccc cgg tgg cgg taa        1677
Leu Leu Phe Leu Ala Leu Thr Val Ala Arg Pro Arg Trp Arg
545                 550                 555

<210> SEQ ID NO 11
<211> LENGTH: 558
<212> TYPE: PRT
<213> ORGANISM: Homo sapiens

<400> SEQUENCE: 11

Met Glu Leu Arg Ala Arg Gly Trp Trp Leu Leu Cys Ala Ala Ala
1               5                   10                  15

Leu Val Ala Cys Ala Arg Gly Asp Pro Ala Ser Lys Ser Arg Ser Cys
            20                  25                  30

Gly Glu Val Arg Gln Ile Tyr Gly Ala Lys Gly Phe Ser Leu Ser Asp
        35                  40                  45

Val Pro Gln Ala Glu Ile Ser Gly Glu His Leu Arg Ile Cys Pro Gln
    50                  55                  60

Gly Tyr Thr Cys Cys Thr Ser Glu Met Glu Glu Asn Leu Ala Asn Arg
65                  70                  75                  80

Ser His Ala Glu Leu Glu Thr Ala Leu Arg Asp Ser Ser Arg Val Leu
                85                  90                  95

Gln Ala Met Leu Ala Thr Gln Leu Arg Ser Phe Asp Asp His Phe Gln
            100                 105                 110

His Leu Leu Asn Asp Ser Glu Arg Thr Leu Gln Ala Thr Phe Pro Gly
        115                 120                 125

Ala Phe Gly Glu Leu Tyr Thr Gln Asn Ala Arg Ala Phe Arg Asp Leu
    130                 135                 140

Tyr Ser Glu Leu Arg Leu Tyr Tyr Arg Gly Ala Asn Leu His Leu Glu
145                 150                 155                 160

Glu Thr Leu Ala Glu Phe Trp Ala Arg Leu Leu Glu Arg Leu Phe Lys
                165                 170                 175

Gln Leu His Pro Gln Leu Leu Leu Pro Asp Asp Tyr Leu Asp Cys Leu
            180                 185                 190
```

```
Gly Lys Gln Ala Glu Ala Leu Arg Pro Phe Gly Glu Ala Pro Arg Glu
            195                 200                 205

Leu Arg Leu Arg Ala Thr Arg Ala Phe Val Ala Ala Arg Ser Phe Val
210                 215                 220

Gln Gly Leu Gly Val Ala Ser Asp Val Val Arg Lys Val Ala Gln Val
225                 230                 235                 240

Pro Leu Gly Pro Glu Cys Ser Arg Ala Val Met Lys Leu Val Tyr Cys
                245                 250                 255

Ala His Cys Leu Gly Val Pro Gly Ala Arg Pro Cys Pro Asp Tyr Cys
            260                 265                 270

Arg Asn Val Leu Lys Gly Cys Leu Ala Asn Gln Ala Asp Leu Asp Ala
        275                 280                 285

Glu Trp Arg Asn Leu Leu Asp Ser Met Val Leu Ile Thr Asp Lys Phe
290                 295                 300

Trp Gly Thr Ser Gly Val Glu Ser Val Ile Gly Ser Val His Thr Trp
305                 310                 315                 320

Leu Ala Glu Ala Ile Asn Ala Leu Gln Asp Asn Arg Asp Thr Leu Thr
                325                 330                 335

Ala Lys Val Ile Gln Gly Cys Gly Asn Pro Lys Val Asn Pro Gln Gly
            340                 345                 350

Pro Gly Pro Glu Glu Lys Arg Arg Gly Lys Leu Ala Pro Arg Glu
        355                 360                 365

Arg Pro Pro Ser Gly Thr Leu Glu Lys Leu Val Ser Glu Ala Lys Ala
370                 375                 380

Gln Leu Arg Asp Val Gln Asp Phe Trp Ile Ser Leu Pro Gly Thr Leu
385                 390                 395                 400

Cys Ser Glu Lys Met Ala Leu Ser Thr Ala Ser Asp Asp Arg Cys Trp
                405                 410                 415

Asn Gly Met Ala Arg Gly Arg Tyr Leu Pro Glu Val Met Gly Asp Gly
            420                 425                 430

Leu Ala Asn Gln Ile Asn Asn Pro Glu Val Glu Val Asp Ile Thr Lys
        435                 440                 445

Pro Asp Met Thr Ile Arg Gln Gln Ile Met Gln Leu Lys Ile Met Thr
450                 455                 460

Asn Arg Leu Arg Ser Ala Tyr Asn Gly Asn Asp Val Asp Phe Gln Asp
465                 470                 475                 480

Ala Ser Asp Asp Gly Ser Gly Ser Gly Asp Gly Cys Leu Asp
                485                 490                 495

Asp Leu Cys Gly Arg Lys Val Ser Arg Lys Ser Ser Ser Arg Thr
            500                 505                 510

Pro Leu Thr His Ala Leu Pro Gly Leu Ser Glu Gln Glu Gly Gln Lys
        515                 520                 525

Thr Ser Ala Ala Ser Cys Pro Gln Pro Thr Phe Leu Leu Pro Leu
530                 535                 540

Leu Leu Phe Leu Ala Leu Thr Val Ala Arg Pro Arg Trp Arg
545                 550                 555

<210> SEQ ID NO 12
<211> LENGTH: 369
<212> TYPE: DNA
<213> ORGANISM: Mus musculus
<220> FEATURE:
<221> NAME/KEY: CDS
<222> LOCATION: (1)..(366)
```

```
<400> SEQUENCE: 12 atg aag cct ttt cat act gcc ctc tcc ttc ctc att ctt aca act gct      48
Met Lys Pro Phe His Thr Ala Leu Ser Phe Leu Ile Leu Thr Thr Ala
1               5                   10                  15 ctt gga atc tgg gcc cag atc aca cat gca aca gag aca aaa gaa gtc      96
Leu Gly Ile Trp Ala Gln Ile Thr His Ala Thr Glu Thr Lys Glu Val
            20                  25                  30 cag agc agt ctg aag gca cag caa ggg ctt gaa att gaa atg ttt cac     144
Gln Ser Ser Leu Lys Ala Gln Gln Gly Leu Glu Ile Glu Met Phe His
        35                  40                  45 atg ggc ttt caa gac tct tca gat tgc tgc ctg tcc tat aac tca cgg     192
Met Gly Phe Gln Asp Ser Ser Asp Cys Cys Leu Ser Tyr Asn Ser Arg
50                  55                  60 att cag tgt tca aga ttt ata ggt tat ttt ccc acc agt ggt ggg tgt     240
Ile Gln Cys Ser Arg Phe Ile Gly Tyr Phe Pro Thr Ser Gly Gly Cys
65                  70                  75                  80 acc agg ccg ggc atc atc ttt atc agc aag agg ggg ttc cag gtc tgt     288
Thr Arg Pro Gly Ile Ile Phe Ile Ser Lys Arg Gly Phe Gln Val Cys
                85                  90                  95 gcc aac ccc agt gat cgg aga gtt cag aga tgc att gaa aga ttg gag     336
Ala Asn Pro Ser Asp Arg Arg Val Gln Arg Cys Ile Glu Arg Leu Glu
            100                 105                 110 caa aac tca caa cca cgg acc tac aaa caa taa                         369
Gln Asn Ser Gln Pro Arg Thr Tyr Lys Gln
        115                 120

<210> SEQ ID NO 13
<211> LENGTH: 122
<212> TYPE: PRT
<213> ORGANISM: Mus musculus

<400> SEQUENCE: 13

Met Lys Pro Phe His Thr Ala Leu Ser Phe Leu Ile Leu Thr Thr Ala
1               5                   10                  15

Leu Gly Ile Trp Ala Gln Ile Thr His Ala Thr Glu Thr Lys Glu Val
            20                  25                  30

Gln Ser Ser Leu Lys Ala Gln Gln Gly Leu Glu Ile Glu Met Phe His
        35                  40                  45

Met Gly Phe Gln Asp Ser Ser Asp Cys Cys Leu Ser Tyr Asn Ser Arg
50                  55                  60

Ile Gln Cys Ser Arg Phe Ile Gly Tyr Phe Pro Thr Ser Gly Gly Cys
65                  70                  75                  80

Thr Arg Pro Gly Ile Ile Phe Ile Ser Lys Arg Gly Phe Gln Val Cys
                85                  90                  95

Ala Asn Pro Ser Asp Arg Arg Val Gln Arg Cys Ile Glu Arg Leu Glu
            100                 105                 110

Gln Asn Ser Gln Pro Arg Thr Tyr Lys Gln
        115                 120

<210> SEQ ID NO 14
<211> LENGTH: 1223
<212> TYPE: DNA
<213> ORGANISM: Mus musculus
<220> FEATURE:
<221> NAME/KEY: CDS
<222> LOCATION: (84)..(1121)
```

<400> SEQUENCE: 14

```
gtgacccgga agggagcccc gtggtagagg tgaccggagc tgagcatttc agatctgctt      60
agtaaaccgg tgtatcgccc acc atg ttg gct gca agg ctt gtg tgt ctc cgg    113
                          Met Leu Ala Ala Arg Leu Val Cys Leu Arg
                          1               5                    10 aca cta cct tcc agg gtt ttc cag ccc act ttc atc acc aag gcc tct      161
Thr Leu Pro Ser Arg Val Phe Gln Pro Thr Phe Ile Thr Lys Ala Ser
                15                  20                  25 cca ctt gtg aag aat tcc atc aca aag aac caa tgg ctc gta aca ccc      209
Pro Leu Val Lys Asn Ser Ile Thr Lys Asn Gln Trp Leu Val Thr Pro
        30                  35                  40 agc agg gaa tat gct acc aag aca aga att agg act cac cgt ggg aaa      257
Ser Arg Glu Tyr Ala Thr Lys Thr Arg Ile Arg Thr His Arg Gly Lys
    45                  50                  55 act gga caa gaa ctg aaa gag gca gcc ttg gaa cca tca atg gaa aaa      305
Thr Gly Gln Glu Leu Lys Glu Ala Ala Leu Glu Pro Ser Met Glu Lys
60                  65                  70 atc ttt aaa atc gat caa atg gga agg tgg ttt gtt gct gga gga gca      353
Ile Phe Lys Ile Asp Gln Met Gly Arg Trp Phe Val Ala Gly Gly Ala
75                  80                  85                  90 gct gtt ggt ctt gga gcg ctc tgc tac tat ggc ttg gga atg tct aat      401
Ala Val Gly Leu Gly Ala Leu Cys Tyr Tyr Gly Leu Gly Met Ser Asn
                95                  100                 105 gag att gga gct atc gaa aag gct gta att tgg cct cag tat gta aag      449
Glu Ile Gly Ala Ile Glu Lys Ala Val Ile Trp Pro Gln Tyr Val Lys
            110                 115                 120 gat aga att cat tct act tac atg tac tta gca gga agg tat tgt tta      497
Asp Arg Ile His Ser Thr Tyr Met Tyr Leu Ala Gly Arg Tyr Cys Leu
        125                 130                 135 aca gct ttg tct gcc ttg gca gta gcc aga aca cct gct ctc atg aac      545
Thr Ala Leu Ser Ala Leu Ala Val Ala Arg Thr Pro Ala Leu Met Asn
    140                 145                 150 ttc atg atg aca ggc tct tgg gtg aca att ggt gcg acc ttt gca gcc      593
Phe Met Met Thr Gly Ser Trp Val Thr Ile Gly Ala Thr Phe Ala Ala
155                 160                 165                 170 atg att gga gct gga atg ctt gta cac tca ata tca tat gag cag agc      641
Met Ile Gly Ala Gly Met Leu Val His Ser Ile Ser Tyr Glu Gln Ser
                175                 180                 185 cca ggc cca aag cat ctg gct tgg atg ctg cat tct ggt gtg atg ggt      689
Pro Gly Pro Lys His Leu Ala Trp Met Leu His Ser Gly Val Met Gly
            190                 195                 200 gca gtt gtg gct cct ctg acg atc tta ggg ggg cct ctt ctc ctg aga      737
Ala Val Val Ala Pro Leu Thr Ile Leu Gly Gly Pro Leu Leu Leu Arg
        205                 210                 215 gcc gca tgg tac acc gct ggt att gtg gga ggc ctc tct act gtg gcc      785
Ala Ala Trp Tyr Thr Ala Gly Ile Val Gly Gly Leu Ser Thr Val Ala
    220                 225                 230 atg tgt gcg cct agt gag aag ttt ctg aac atg gga gca ccc ctg gga      833
Met Cys Ala Pro Ser Glu Lys Phe Leu Asn Met Gly Ala Pro Leu Gly
235                 240                 245                 250 gtg ggc ctg ggt ctt gtc ttt gcg tct tct ctg ggg tct atg ttt ctt      881
Val Gly Leu Gly Leu Val Phe Ala Ser Ser Leu Gly Ser Met Phe Leu
                255                 260                 265 ccc cct acc tct gtg gct ggt gcc act ctg tac tca gtg gca atg tat      929
Pro Pro Thr Ser Val Ala Gly Ala Thr Leu Tyr Ser Val Ala Met Tyr
            270                 275                 280 ggt gga tta gtt ctt ttc agc atg ttc ctt ctg tat gat act cag aaa      977
Gly Gly Leu Val Leu Phe Ser Met Phe Leu Leu Tyr Asp Thr Gln Lys
        285                 290                 295
```

```
gta atc aaa cgt gca gaa ata aca ccc atg tat gga gct caa aag tat      1025
Val Ile Lys Arg Ala Glu Ile Thr Pro Met Tyr Gly Ala Gln Lys Tyr
300                 305                 310 gat ccc atc aat tcg atg ttg aca atc tac atg gat aca tta aat ata      1073
Asp Pro Ile Asn Ser Met Leu Thr Ile Tyr Met Asp Thr Leu Asn Ile
315                 320                 325                 330 ttt atg cga gtt gca act atg cta gca act gga agc aac aga aag aaa      1121
Phe Met Arg Val Ala Thr Met Leu Ala Thr Gly Ser Asn Arg Lys Lys
                335                 340                 345 tgaagtaacc gcttgtgatg tctccgctca ctgatgtctt gcttgtttaa taggagcaga    1181
tagtcattac agtttgcatc agcagaattc ccgcgcggcc gc                      1223

<210> SEQ ID NO 15
<211> LENGTH: 346
<212> TYPE: PRT
<213> ORGANISM: Mus musculus

<400> SEQUENCE: 15

Met Leu Ala Ala Arg Leu Val Cys Leu Arg Thr Leu Pro Ser Arg Val
1               5                   10                  15

Phe Gln Pro Thr Phe Ile Thr Lys Ala Ser Pro Leu Val Lys Asn Ser
                20                  25                  30

Ile Thr Lys Asn Gln Trp Leu Val Thr Pro Ser Arg Glu Tyr Ala Thr
            35                  40                  45

Lys Thr Arg Ile Arg Thr His Arg Gly Lys Thr Gly Gln Glu Leu Lys
        50                  55                  60

Glu Ala Ala Leu Glu Pro Ser Met Glu Lys Ile Phe Lys Ile Asp Gln
65                  70                  75                  80

Met Gly Arg Trp Phe Val Ala Gly Gly Ala Ala Val Gly Leu Gly Ala
                85                  90                  95

Leu Cys Tyr Tyr Gly Leu Gly Met Ser Asn Glu Ile Gly Ala Ile Glu
            100                 105                 110

Lys Ala Val Ile Trp Pro Gln Tyr Val Lys Asp Arg Ile His Ser Thr
        115                 120                 125

Tyr Met Tyr Leu Ala Gly Arg Tyr Cys Leu Thr Ala Leu Ser Ala Leu
    130                 135                 140

Ala Val Ala Arg Thr Pro Ala Leu Met Asn Phe Met Thr Gly Ser
145                 150                 155                 160

Trp Val Thr Ile Gly Ala Thr Phe Ala Ala Met Ile Gly Ala Gly Met
                165                 170                 175

Leu Val His Ser Ile Ser Tyr Glu Gln Ser Pro Gly Pro Lys His Leu
            180                 185                 190

Ala Trp Met Leu His Ser Gly Val Met Gly Ala Val Ala Pro Leu
        195                 200                 205

Thr Ile Leu Gly Gly Pro Leu Leu Leu Arg Ala Ala Trp Tyr Thr Ala
    210                 215                 220

Gly Ile Val Gly Gly Leu Ser Thr Val Ala Met Cys Ala Pro Ser Glu
225                 230                 235                 240

Lys Phe Leu Asn Met Gly Ala Pro Leu Gly Val Gly Leu Gly Leu Val
                245                 250                 255

Phe Ala Ser Ser Leu Gly Ser Met Phe Leu Pro Pro Thr Ser Val Ala
            260                 265                 270

Gly Ala Thr Leu Tyr Ser Val Ala Met Tyr Gly Gly Leu Val Leu Phe
        275                 280                 285
```

```
Ser Met Phe Leu Leu Tyr Asp Thr Gln Lys Val Ile Lys Arg Ala Glu
    290                 295                 300
Ile Thr Pro Met Tyr Gly Ala Gln Lys Tyr Asp Pro Ile Asn Ser Met
305                 310                 315                 320
Leu Thr Ile Tyr Met Asp Thr Leu Asn Ile Phe Met Arg Val Ala Thr
                325                 330                 335
Met Leu Ala Thr Gly Ser Asn Arg Lys Lys
            340                 345
```

<210> SEQ ID NO 16
<211> LENGTH: 1038
<212> TYPE: DNA
<213> ORGANISM: Homo sapiens
<220> FEATURE:
<221> NAME/KEY: CDS
<222> LOCATION: (1)..(1035)

<400> SEQUENCE: 16

```
atg ttg gct gca agg ctg gtg tgt ctc cgg aca cta cct tct agg gtt      48
Met Leu Ala Ala Arg Leu Val Cys Leu Arg Thr Leu Pro Ser Arg Val
1               5                  10                  15 ttc cac cca gct ttc acc aag gcc tcc cct gtt gtg aag aat tcc atc      96
Phe His Pro Ala Phe Thr Lys Ala Ser Pro Val Val Lys Asn Ser Ile
            20                  25                  30 acg aag aat caa tgg ctg tta aca cct agc agg gaa tat gcc acc aaa     144
Thr Lys Asn Gln Trp Leu Leu Thr Pro Ser Arg Glu Tyr Ala Thr Lys
        35                  40                  45 aca aga att ggg atc cgg cgt ggg aga act ggc caa gaa ctc aaa gag     192
Thr Arg Ile Gly Ile Arg Arg Gly Arg Thr Gly Gln Glu Leu Lys Glu
    50                  55                  60 gca gca ttg gaa cca tcg atg gaa aaa ata ttt aaa att gat cag atg     240
Ala Ala Leu Glu Pro Ser Met Glu Lys Ile Phe Lys Ile Asp Gln Met
65                  70                  75                  80 gga aga tgg ttt gtt gct gga ggg gct gct gtt ggt ctt gga gca ttg     288
Gly Arg Trp Phe Val Ala Gly Gly Ala Ala Val Gly Leu Gly Ala Leu
                85                  90                  95 tgc tac tat ggc ttg gga ctg tct aat gag att gga gct att gaa aag     336
Cys Tyr Tyr Gly Leu Gly Leu Ser Asn Glu Ile Gly Ala Ile Glu Lys
            100                 105                 110 gct gta att tgg cct cag tat gtc aag gat aga att cat tcc acc tat     384
Ala Val Ile Trp Pro Gln Tyr Val Lys Asp Arg Ile His Ser Thr Tyr
        115                 120                 125 atg tac tta gca ggg agt att ggt tta aca gct ttg tct gcc ata gca     432
Met Tyr Leu Ala Gly Ser Ile Gly Leu Thr Ala Leu Ser Ala Ile Ala
    130                 135                 140 atc agc aga acg cct gtt ctc atg aac ttc atg atg aga ggc tct tgg     480
Ile Ser Arg Thr Pro Val Leu Met Asn Phe Met Met Arg Gly Ser Trp
145                 150                 155                 160 gtg aca att ggt gtg acc ttt gca gcc atg gtt gga gct gga atg ctg     528
Val Thr Ile Gly Val Thr Phe Ala Ala Met Val Gly Ala Gly Met Leu
                165                 170                 175 gta cga tca ata cca tat gac cag agc cca ggc cca aag cat ctt gct     576
Val Arg Ser Ile Pro Tyr Asp Gln Ser Pro Gly Pro Lys His Leu Ala
            180                 185                 190 tgg ttg cta cat tct ggt gtg atg ggt gca gtg gtg gct cct ctg aca     624
Trp Leu Leu His Ser Gly Val Met Gly Ala Val Val Ala Pro Leu Thr
        195                 200                 205 ata tta ggg ggt cct ctt ctc atc aga gct gca tgg tac aca gct ggc     672
Ile Leu Gly Gly Pro Leu Leu Ile Arg Ala Ala Trp Tyr Thr Ala Gly
    210                 215                 220
```

```
att gtg gga ggc ctc tcc act gtg gcc atg tgt gcg ccc agt gaa aag      720
Ile Val Gly Gly Leu Ser Thr Val Ala Met Cys Ala Pro Ser Glu Lys
225             230                 235                 240 ttt ctg aac atg ggt gca ccc ctg gga gtg ggc ctg ggt ctc gtc ttt      768
Phe Leu Asn Met Gly Ala Pro Leu Gly Val Gly Leu Gly Leu Val Phe
            245                 250                 255 gtg tcc tca ttg gga tct atg ttt ctt cca cct acc acc gtg gct ggt      816
Val Ser Ser Leu Gly Ser Met Phe Leu Pro Pro Thr Thr Val Ala Gly
        260                 265                 270 gcc act ctt tac tca gtg gca atg tac ggt gga tta gtt ctt ttc agc      864
Ala Thr Leu Tyr Ser Val Ala Met Tyr Gly Gly Leu Val Leu Phe Ser
    275                 280                 285 atg ttc ctt ctg tat gat acc cag aaa gta atc aag cgt gca gaa gta      912
Met Phe Leu Leu Tyr Asp Thr Gln Lys Val Ile Lys Arg Ala Glu Val
290                 295                 300 tca cca atg tat gga gtt caa aaa tat gat ccc att aac tcg atg ctg      960
Ser Pro Met Tyr Gly Val Gln Lys Tyr Asp Pro Ile Asn Ser Met Leu
305             310                 315                 320 agt atc tac atg gat aca tta aat ata ttt atg cga gtt gca act atg     1008
Ser Ile Tyr Met Asp Thr Leu Asn Ile Phe Met Arg Val Ala Thr Met
            325                 330                 335 ctg gca act gga ggc aac aga aag aaa tga                             1038
Leu Ala Thr Gly Gly Asn Arg Lys Lys
        340                 345

<210> SEQ ID NO 17
<211> LENGTH: 345
<212> TYPE: PRT
<213> ORGANISM: Homo sapiens

<400> SEQUENCE: 17

Met Leu Ala Ala Arg Leu Val Cys Leu Arg Thr Leu Pro Ser Arg Val
1               5                   10                  15

Phe His Pro Ala Phe Thr Lys Ala Ser Pro Val Val Lys Asn Ser Ile
            20                  25                  30

Thr Lys Asn Gln Trp Leu Leu Thr Pro Ser Arg Glu Tyr Ala Thr Lys
        35                  40                  45

Thr Arg Ile Gly Ile Arg Arg Gly Arg Thr Gly Gln Glu Leu Lys Glu
    50                  55                  60

Ala Ala Leu Glu Pro Ser Met Glu Lys Ile Phe Lys Ile Asp Gln Met
65                  70                  75                  80

Gly Arg Trp Phe Val Ala Gly Gly Ala Ala Val Gly Leu Gly Ala Leu
                85                  90                  95

Cys Tyr Tyr Gly Leu Gly Leu Ser Asn Glu Ile Gly Ala Ile Glu Lys
            100                 105                 110

Ala Val Ile Trp Pro Gln Tyr Val Lys Asp Arg Ile His Ser Thr Tyr
        115                 120                 125

Met Tyr Leu Ala Gly Ser Ile Gly Leu Thr Ala Leu Ser Ala Ile Ala
    130                 135                 140

Ile Ser Arg Thr Pro Val Leu Met Asn Phe Met Met Arg Gly Ser Trp
145                 150                 155                 160

Val Thr Ile Gly Val Thr Phe Ala Ala Met Val Gly Ala Gly Met Leu
                165                 170                 175

Val Arg Ser Ile Pro Tyr Asp Gln Ser Pro Gly Pro Lys His Leu Ala
            180                 185                 190

Trp Leu Leu His Ser Gly Val Met Gly Ala Val Val Ala Pro Leu Thr
        195                 200                 205
```

-continued

```
Ile Leu Gly Gly Pro Leu Leu Ile Arg Ala Ala Trp Tyr Thr Ala Gly
    210                 215                 220
Ile Val Gly Gly Leu Ser Thr Val Ala Met Cys Ala Pro Ser Glu Lys
225                 230                 235                 240
Phe Leu Asn Met Gly Ala Pro Leu Gly Val Gly Leu Gly Leu Val Phe
                245                 250                 255
Val Ser Ser Leu Gly Ser Met Phe Leu Pro Pro Thr Thr Val Ala Gly
            260                 265                 270
Ala Thr Leu Tyr Ser Val Ala Met Tyr Gly Gly Leu Val Leu Phe Ser
        275                 280                 285
Met Phe Leu Leu Tyr Asp Thr Gln Lys Val Ile Lys Arg Ala Glu Val
    290                 295                 300
Ser Pro Met Tyr Gly Val Gln Lys Tyr Asp Pro Ile Asn Ser Met Leu
305                 310                 315                 320
Ser Ile Tyr Met Asp Thr Leu Asn Ile Phe Met Arg Val Ala Thr Met
                325                 330                 335
Leu Ala Thr Gly Gly Asn Arg Lys Lys
            340                 345

<210> SEQ ID NO 18
<211> LENGTH: 447
<212> TYPE: DNA
<213> ORGANISM: Mus musculus
<220> FEATURE:
<221> NAME/KEY: CDS
<222> LOCATION: (1)..(444)

<400> SEQUENCE: 18 atg agc acc tcg tct gcg cgg cct gca gtc ctg gcc ctt gcc ggg ctg       48
Met Ser Thr Ser Ser Ala Arg Pro Ala Val Leu Ala Leu Ala Gly Leu
1               5                   10                  15 gct ctg ctc ctt ctg ctg tgc ctg ggt cca gat ggc ata agt gga aac       96
Ala Leu Leu Leu Leu Leu Cys Leu Gly Pro Asp Gly Ile Ser Gly Asn
            20                  25                  30 aaa ctc aag aag atg ctc cag aaa cga gaa gga cct gtc ccg tca aag      144
Lys Leu Lys Lys Met Leu Gln Lys Arg Glu Gly Pro Val Pro Ser Lys
        35                  40                  45 act aat gta gct gta gcc gag aac aca gca aag gaa ttc cta ggt ggc      192
Thr Asn Val Ala Val Ala Glu Asn Thr Ala Lys Glu Phe Leu Gly Gly
    50                  55                  60 ctg aag cgt gcc aaa cga cag ctg tgg gac cgt acg cgg cct gag gta      240
Leu Lys Arg Ala Lys Arg Gln Leu Trp Asp Arg Thr Arg Pro Glu Val
65                  70                  75                  80 cag cag tgg tac cag cag ttc ctc tac atg ggc ttt gat gag gct aaa      288
Gln Gln Trp Tyr Gln Gln Phe Leu Tyr Met Gly Phe Asp Glu Ala Lys
                85                  90                  95 ttt gaa gat gat gtc aac tat tgg cta aac aga aat cga aac ggc cat      336
Phe Glu Asp Asp Val Asn Tyr Trp Leu Asn Arg Asn Arg Asn Gly His
            100                 105                 110 gac tac tat ggt gac tac tac cag cgt cat tat gat gaa gat gcg gcc      384
Asp Tyr Tyr Gly Asp Tyr Tyr Gln Arg His Tyr Asp Glu Asp Ala Ala
        115                 120                 125 att ggt ccc cac agc cgg gaa agc ttc agg cat gga gcc agt gtg aac      432
Ile Gly Pro His Ser Arg Glu Ser Phe Arg His Gly Ala Ser Val Asn
    130                 135                 140 tat gat gac tat taa                                                  447
Tyr Asp Asp Tyr
145
```

<210> SEQ ID NO 19
<211> LENGTH: 148
<212> TYPE: PRT
<213> ORGANISM: Mus musculus

<400> SEQUENCE: 19

Met Ser Thr Ser Ser Ala Arg Pro Ala Val Leu Ala Leu Ala Gly Leu
1               5                   10                  15

Ala Leu Leu Leu Leu Leu Cys Leu Gly Pro Asp Gly Ile Ser Gly Asn
            20                  25                  30

Lys Leu Lys Lys Met Leu Gln Lys Arg Glu Gly Pro Val Pro Ser Lys
        35                  40                  45

Thr Asn Val Ala Val Ala Glu Asn Thr Ala Lys Glu Phe Leu Gly Gly
    50                  55                  60

Leu Lys Arg Ala Lys Arg Gln Leu Trp Asp Thr Arg Pro Glu Val
65                  70                  75                  80

Gln Gln Trp Tyr Gln Gln Phe Leu Tyr Met Gly Phe Asp Glu Ala Lys
                85                  90                  95

Phe Glu Asp Asp Val Asn Tyr Trp Leu Asn Arg Asn Arg Asn Gly His
            100                 105                 110

Asp Tyr Tyr Gly Asp Tyr Tyr Gln Arg His Tyr Asp Glu Asp Ala Ala
        115                 120                 125

Ile Gly Pro His Ser Arg Glu Ser Phe Arg His Gly Ala Ser Val Asn
    130                 135                 140

Tyr Asp Asp Tyr
145

<210> SEQ ID NO 20
<211> LENGTH: 447
<212> TYPE: DNA
<213> ORGANISM: Homo sapiens
<220> FEATURE:
<221> NAME/KEY: CDS
<222> LOCATION: (1)..(444)

<400> SEQUENCE: 20 atg gct gcc tcc ccc gcg cgg cct gct gtc ctg gcc ctg acc ggg ctg      48
Met Ala Ala Ser Pro Ala Arg Pro Ala Val Leu Ala Leu Thr Gly Leu
1               5                   10                  15 gcg ctg ctc ctg ctc ctg tgc tgg ggc cca ggt ggc ata agt gga aat      96
Ala Leu Leu Leu Leu Leu Cys Trp Gly Pro Gly Gly Ile Ser Gly Asn
            20                  25                  30 aaa ctc aag ctg atg ctt caa aaa cga gaa gca cct gtt cca act aag     144
Lys Leu Lys Leu Met Leu Gln Lys Arg Glu Ala Pro Val Pro Thr Lys
        35                  40                  45 act aaa gtg gcc gtt gat gag aat aaa gcc aaa gaa ttc ctt ggc agc     192
Thr Lys Val Ala Val Asp Glu Asn Lys Ala Lys Glu Phe Leu Gly Ser
    50                  55                  60 ctg aag cgc cag aag cgg cag ctg tgg gac cgg act cgg ccc gag gtg     240
Leu Lys Arg Gln Lys Arg Gln Leu Trp Asp Arg Thr Arg Pro Glu Val
65                  70                  75                  80 cag cag tgg tac cag cag ttt ctc tac atg ggc ttt gac gaa gcg aaa     288
Gln Gln Trp Tyr Gln Gln Phe Leu Tyr Met Gly Phe Asp Glu Ala Lys
                85                  90                  95 ttt gaa gat gac atc acc tat tgg ctt aac aga gat cga aat gga cat     336
Phe Glu Asp Asp Ile Thr Tyr Trp Leu Asn Arg Asp Arg Asn Gly His
            100                 105                 110 gaa tac tat ggc gat tac tac caa cgt cac tat gat gaa gac tct gca     384
Glu Tyr Tyr Gly Asp Tyr Tyr Gln Arg His Tyr Asp Glu Asp Ser Ala
        115                 120                 125

```
att ggt ccc cgg agc ccc tac ggc ttt agg cat gga gcc agc gtc aac     432
Ile Gly Pro Arg Ser Pro Tyr Gly Phe Arg His Gly Ala Ser Val Asn
    130                 135                 140 tac gat gac tac taa                                                 447
Tyr Asp Asp Tyr
145

<210> SEQ ID NO 21
<211> LENGTH: 148
<212> TYPE: PRT
<213> ORGANISM: Homo sapiens

<400> SEQUENCE: 21

Met Ala Ala Ser Pro Ala Arg Pro Ala Val Leu Ala Leu Thr Gly Leu
1               5                   10                  15

Ala Leu Leu Leu Leu Leu Cys Trp Gly Pro Gly Gly Ile Ser Gly Asn
                20                  25                  30

Lys Leu Lys Leu Met Leu Gln Lys Arg Glu Ala Pro Val Pro Thr Lys
            35                  40                  45

Thr Lys Val Ala Val Asp Glu Asn Lys Ala Lys Glu Phe Leu Gly Ser
        50                  55                  60

Leu Lys Arg Gln Lys Arg Gln Leu Trp Asp Arg Thr Arg Pro Glu Val
65                  70                  75                  80

Gln Gln Trp Tyr Gln Gln Phe Leu Tyr Met Gly Phe Asp Glu Ala Lys
                85                  90                  95

Phe Glu Asp Asp Ile Thr Tyr Trp Leu Asn Arg Asp Arg Asn Gly His
            100                 105                 110

Glu Tyr Tyr Gly Asp Tyr Tyr Gln Arg His Tyr Asp Glu Asp Ser Ala
        115                 120                 125

Ile Gly Pro Arg Ser Pro Tyr Gly Phe Arg His Gly Ala Ser Val Asn
    130                 135                 140

Tyr Asp Asp Tyr
145

<210> SEQ ID NO 22
<211> LENGTH: 3132
<212> TYPE: DNA
<213> ORGANISM: Mus musculus
<220> FEATURE:
<221> NAME/KEY: CDS
<222> LOCATION: (630)..(1358)

<400> SEQUENCE: 22
gggggtctgc atctccatcg aaagtgcgc tggccacatc ccttcggcct ccgggcagtg     60
ttctgtctcc cttagctcag gcagcgagaa acttcagctg tgaagtggtg gtggagagag   120
ccctgggagc agcgactgga cccggacacc aagaagagag tggacgcgcc cctcgactag   180
gaatcgctct cgcaggcgga gacccagcat ctcagcgcct gcggtcgcgc ttgcccggcc   240
gcgcgctttt gctaggcgcc gccagccccg aaggaccctc ggggtccgcg gacccttctg   300
cagccggcgg aatcctaaag ctgccaagag ctcccggcgg gtgtcggcaa acttttccg    360 agcccacgtg ctgaccaaac agcccggctc gcttccagag cctggcatgg agcgccgcgc   420
ctaggcacgc cgtgcagccc gagagacgcg agcgcacggt tcaccgtgga gggagagatg   480
ctcatcgagc caaattgatc attgcagccc caggggcagtg acatctgtct ctgagtcctc   540
cctaggagcg cgacccgcac tgtctccttc caggagcccg tcatttcctc gacttttgag   600
```

-continued

| | | |
|---|---|---|
| aggtgtctct ccccagcccg accgtccag atg cgt ttt tgc ctc ttc tca ttt<br>                                                                   Met Arg Phe Cys Leu Phe Ser Phe<br>                                                                    1               5 | 653 |

```
aggtgtctct ccccagcccg accgtccag atg cgt ttt tgc ctc ttc tca ttt       653
                                Met Arg Phe Cys Leu Phe Ser Phe
                                  1               5 gcc ctc atc att ctg aac tgt atg gat tac agc cag tgc caa ggc aac       701
Ala Leu Ile Ile Leu Asn Cys Met Asp Tyr Ser Gln Cys Gln Gly Asn
     10               15                  20 cga tgg aga cgc aat aag cga gct agt tat gta tca aat ccc att tgc       749
Arg Trp Arg Arg Asn Lys Arg Ala Ser Tyr Val Ser Asn Pro Ile Cys
 25              30                  35                  40 aag ggt tgt ttg tct tgt tcg aag gac aat ggt tgc agc cga tgt caa       797
Lys Gly Cys Leu Ser Cys Ser Lys Asp Asn Gly Cys Ser Arg Cys Gln
                 45                  50                  55 cag aag ttg ttc ttt ttc ctt cga aga gaa gga atg cgt cag tat gga       845
Gln Lys Leu Phe Phe Phe Leu Arg Arg Glu Gly Met Arg Gln Tyr Gly
             60                  65                  70 gag tgc ctg cat tcc tgc cca tca ggg tat tat gga cac cga gcc cca       893
Glu Cys Leu His Ser Cys Pro Ser Gly Tyr Tyr Gly His Arg Ala Pro
         75                  80                  85 gat atg aac aga tgt gca cga tgc aga ata gaa aac tgt gat tct tgc       941
Asp Met Asn Arg Cys Ala Arg Cys Arg Ile Glu Asn Cys Asp Ser Cys
     90                  95                 100 ttt agc aaa gac ttt tgt acg aag tgc aaa gta ggc ttt tat ttg cat       989
Phe Ser Lys Asp Phe Cys Thr Lys Cys Lys Val Gly Phe Tyr Leu His
105                 110                 115                 120 aga ggc cgc tgc ttt gat gaa tgt cca gat ggt ttt gca ccg tta gat      1037
Arg Gly Arg Cys Phe Asp Glu Cys Pro Asp Gly Phe Ala Pro Leu Asp
                125                 130                 135 gag act atg gaa tgt gta gaa ggt tgt gaa gtt ggt cat tgg agc gaa      1085
Glu Thr Met Glu Cys Val Glu Gly Cys Glu Val Gly His Trp Ser Glu
            140                 145                 150 tgg gga acg tgt agc aga aac aac cgc acg tgt gga ttt aaa tgg ggt      1133
Trp Gly Thr Cys Ser Arg Asn Asn Arg Thr Cys Gly Phe Lys Trp Gly
        155                 160                 165 ctg gaa acc aga aca cgg cag att gtt aaa aag cca gca aaa gac aca      1181
Leu Glu Thr Arg Thr Arg Gln Ile Val Lys Lys Pro Ala Lys Asp Thr
    170                 175                 180 ata cca tgt ccg acc att gcg gag tcc agg aga tgc aag atg gcc atg      1229
Ile Pro Cys Pro Thr Ile Ala Glu Ser Arg Arg Cys Lys Met Ala Met
185                 190                 195                 200 agg cac tgt cca gga gga aag aga aca cca aag gca aaa gag aag aga      1277
Arg His Cys Pro Gly Gly Lys Arg Thr Pro Lys Ala Lys Glu Lys Arg
                205                 210                 215 aac aag aag aag agg cgg aag ctg att gag aga gcc caa gag cag cac      1325
Asn Lys Lys Lys Arg Arg Lys Leu Ile Glu Arg Ala Gln Glu Gln His
                220                 225                 230 agc gtc ttc ctc gct aca gac aga gtg aac caa taaaatacaa gaaatagctg    1378
Ser Val Phe Leu Ala Thr Asp Arg Val Asn Gln
            235                 240 gggcattttg aggttttctg ttttgtttat gttgttgttt tgcaaaagtg cacaaagcta    1438
ctctccagtc cacactggtg gacagcattc tgatcctct gaccagtatc cattttcagt     1498
aatgctgcag agggaggtgc ccaagcatgg actcagcgtt atttatgctt tgattggaat    1558
ctggggcctg tgatggcagg agcttgttga gctgagtcag cgggagctga tgcatctgta    1618
ctcttgtgat gagcacagtg tgtcataaga acctgtccct ggcacggtgg acccacagga    1678
ggcacaaggc tgtagatcac caccagagaa tgcacctgtg cctattttga tggatggcaa    1738
tgctaagcaa gcaagcactg ttcacttgtg actttcattt ctcacactgt gcactgtcaa    1798
agacaaatgt gcatggaaaa atgtttagtg tcacctcatg gcgttctcag catcagtgac    1858
```

```
cttcaaacgg tcctacaatg agactgtgtt ctagctaggg gtatgctgtg gaaattcctg    1918
ctacatttca tcttagtgct aacatgtaca gattctgctg cgctacattc aaagctcatt    1978
actgtatatt tatgctttct ctgtgtaaca agttatacct gataagatgt cactttgttt    2038
ctagtgattc ttaaccatgg tctggtacat ggctattcta gttttggaaa ttaacaagtg    2098
ttttgttgcc tcttgttttc ttttgttcct atcattttg gcgggggttg ggtgggcttg     2158
attctaaccg taagtatagg ataagctagt tttgtatata gagtcaaatg actgatgtca    2218
gaggatcagt gctgatagaa cttccccagt tcatgtcacg atacacacag agagaaagca    2278
gcatgaggca tcttgccatc agaagccaaa tttcttttga gtcccaaaat tgatgactta    2338
tgaaatatag ctgaaaacaa gatttgggtg tagttacttg tatttattat acaatttcca    2398
attacatttt ttttcaaact caaaataacc catgactttg agtgataggt cacttggcaa    2458
tgttcttgaa ttactgggga agctgttgtc actaagataa tgagagagaa aatagaatgg    2518
cttcgcccaa gtgagagcca catcttacat ttctctgttg aatcggaatc aactatatta    2578
gaacagaagc ctgatagaag ctttctagtt aacacacaca aggccatggt ttcaaaaaca    2638
tctttgtccc cttaggtcag tttgtcctta gattatgaat tggcaggttc taattgcatt    2698
atttccctgg ctgatccagg aaaaagttag aacaaaataa gttgcatagt tttgaggaaa    2758
catccaaagc aaggcgaagc cttttccttgc cttgcattgg caaaactacc tctttagcat    2818
ttatgttgat tcagaaacat cttgctgata tgtgtagatg ttttaagctt cattgtgaaa    2878
atattgatgc aagataagcc atatatgaat gttgtattca actttagggc ttgaaattaa    2938
tcctaaagtg ttcacctctc tccatgtcta tttacactct gttcctattt actaagaggg    2998
taggggtctc cttaatatca tacttcattg ttaataagtc aatgcttgtt atgtttcttg    3058
gctgttgttt ttgtgcatta aaaactcaaa attggaaaaa aaaaaaaaa aaaaaaaaa     3118 aaaaaaaaaa aaaa                                                      3132
```

<210> SEQ ID NO 23
<211> LENGTH: 243
<212> TYPE: PRT
<213> ORGANISM: Mus musculus

<400> SEQUENCE: 23

```
Met Arg Phe Cys Leu Phe Ser Phe Ala Leu Ile Ile Leu Asn Cys Met
1               5                   10                  15

Asp Tyr Ser Gln Cys Gln Gly Asn Arg Trp Arg Asn Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Leu Arg
    50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro Leu Asp Glu Thr Met Glu Cys Val Glu Gly
    130                 135                 140
```

```
Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
            165                 170                 175

Val Lys Lys Pro Ala Lys Asp Thr Ile Pro Cys Pro Thr Ile Ala Glu
        180                 185                 190

Ser Arg Arg Cys Lys Met Ala Met Arg His Cys Pro Gly Gly Lys Arg
            195                 200                 205

Thr Pro Lys Ala Lys Glu Lys Arg Asn Lys Lys Arg Arg Lys Leu
        210                 215                 220

Ile Glu Arg Ala Gln Glu Gln His Ser Val Phe Leu Ala Thr Asp Arg
225                 230                 235                 240

Val Asn Gln

<210> SEQ ID NO 24
<211> LENGTH: 843
<212> TYPE: DNA
<213> ORGANISM: Mus musculus
<220> FEATURE:
<221> NAME/KEY: CDS
<222> LOCATION: (132)..(506)

<400> SEQUENCE: 24
ggccattatg gccgggggct tcgccgtcc gggagctgac cggccgtgtt cctctctcgt      60
cttcctctgc gccccgcgtc cccgccctcg cgaccccggc tctcctggac tcggcgccgc    120
caacctgggc g atg ccc cgc tac gag ttg gct ttg att ctg aaa gcc atg    170
            Met Pro Arg Tyr Glu Leu Ala Leu Ile Leu Lys Ala Met
            1               5                   10 cgg cgg cca gag acc gct gct gct ttg aaa cgt aca ata gaa tcc ctg    218
Arg Arg Pro Glu Thr Ala Ala Ala Leu Lys Arg Thr Ile Glu Ser Leu
    15                  20                  25 atg gac cga gga gcc ata gtg agg aac ttg gaa agc ctg ggt gag cgt    266
Met Asp Arg Gly Ala Ile Val Arg Asn Leu Glu Ser Leu Gly Glu Arg
30                  35                  40                  45 gcg ctc ccc tac agg atc tcg agt cac agc cag cag cac agc cga gga    314
Ala Leu Pro Tyr Arg Ile Ser Ser His Ser Gln Gln His Ser Arg Gly
                50                  55                  60 ggg tat ttc ctg gtg gat ttt tat gct ccg aca agt gct gtg gag aac    362
Gly Tyr Phe Leu Val Asp Phe Tyr Ala Pro Thr Ser Ala Val Glu Asn
            65                  70                  75 ata ctg gaa cac ttg gcg cga gac att gac gtg gtt aga cca aat att    410
Ile Leu Glu His Leu Ala Arg Asp Ile Asp Val Val Arg Pro Asn Ile
        80                  85                  90 gtg aaa cac cct ctg acc cag gaa gta aaa gag tgt gac ggc ata gtc    458
Val Lys His Pro Leu Thr Gln Glu Val Lys Glu Cys Asp Gly Ile Val
    95                  100                 105 cca gtc cca ctt gaa gaa aaa ctg tat tca aca aag agg agg aag aag    506
Pro Val Pro Leu Glu Glu Lys Leu Tyr Ser Thr Lys Arg Arg Lys Lys
110                 115                 120                 125 tgagaagatt caccagattc tggccttata tttaatccta agggcactat gggtgctgct    566
aggttgttgt ctaggatact ttagcccatg accattttgc tgcaggaggt agaaactgct    626
ggccgagacc tgccctgatg tctctgctga gatttcatcc cacttgtggg gtttgtcggg    686
agtgggggtg ttcacagtac cactgtagcg tttccaagag caaaatgttt gtcattcaca    746
cttggttgtc ttgcaagcct atatggaaca ctggagcag agtaataaac atgactttat    806
caacactgga aaaaaaaaaa aaaaaaaaa aaaaaaa                               843
```

```
<210> SEQ ID NO 25
<211> LENGTH: 125
<212> TYPE: PRT
<213> ORGANISM: Mus musculus

<400> SEQUENCE: 25

Met Pro Arg Tyr Glu Leu Ala Leu Ile Leu Lys Ala Met Arg Arg Pro
1               5                   10                  15

Glu Thr Ala Ala Ala Leu Lys Arg Thr Ile Glu Ser Leu Met Asp Arg
            20                  25                  30

Gly Ala Ile Val Arg Asn Leu Glu Ser Leu Gly Glu Arg Ala Leu Pro
        35                  40                  45

Tyr Arg Ile Ser Ser His Ser Gln Gln His Ser Arg Gly Gly Tyr Phe
    50                  55                  60

Leu Val Asp Phe Tyr Ala Pro Thr Ser Ala Val Glu Asn Ile Leu Glu
65                  70                  75                  80

His Leu Ala Arg Asp Ile Asp Val Val Arg Pro Asn Ile Val Lys His
                85                  90                  95

Pro Leu Thr Gln Glu Val Lys Glu Cys Asp Gly Ile Val Pro Val Pro
            100                 105                 110

Leu Glu Glu Lys Leu Tyr Ser Thr Lys Arg Arg Lys Lys
        115                 120                 125

<210> SEQ ID NO 26
<211> LENGTH: 2490
<212> TYPE: DNA
<213> ORGANISM: Mus musculus
<220> FEATURE:
<221> NAME/KEY: CDS
<222> LOCATION: (1)..(2487)

<400> SEQUENCE: 26 atg aag ccg ccc ggc agc atc tcc cgg cgg ccg acc ctg acg ggt tgc      48
Met Lys Pro Pro Gly Ser Ile Ser Arg Arg Pro Thr Leu Thr Gly Cys
1               5                   10                  15 agc ctt ccc ggc gcc tcc tgc ggc ccc ggc cgc tgc ccc gcc ggc ccg      96
Ser Leu Pro Gly Ala Ser Cys Gly Pro Gly Arg Cys Pro Ala Gly Pro
            20                  25                  30 gtg ccg gcc cgc gcg ccg ccc tgc cgc ctg ctc ctc gtc ctt ctc ctg     144
Val Pro Ala Arg Ala Pro Pro Cys Arg Leu Leu Leu Val Leu Leu Leu
        35                  40                  45 cta cct gcg ctc gcc acc tca tcc cgg ccc cgt gcc cgg ggg gcc gct     192
Leu Pro Ala Leu Ala Thr Ser Ser Arg Pro Arg Ala Arg Gly Ala Ala
    50                  55                  60 gcg ccc agc gct ccg cac tgg aat gaa act gca gaa aaa acc ctg gga     240
Ala Pro Ser Ala Pro His Trp Asn Glu Thr Ala Glu Lys Thr Leu Gly
65                  70                  75                  80 gtc ctg gca gat gaa gac aac aca ttg caa caa aat agc agc agc aga     288
Val Leu Ala Asp Glu Asp Asn Thr Leu Gln Gln Asn Ser Ser Ser Arg
                85                  90                  95 aat acc agc tac agc agt gca gtg caa aaa gaa atc aca ctg cct tca     336
Asn Thr Ser Tyr Ser Ser Ala Val Gln Lys Glu Ile Thr Leu Pro Ser
            100                 105                 110 aga ctg gtg tat tac atc aac cag gac tca gaa agc ccc tat cat gtt     384
Arg Leu Val Tyr Tyr Ile Asn Gln Asp Ser Glu Ser Pro Tyr His Val
        115                 120                 125 ctt gac aca aag gcc aga cac caa cag aaa cac aat aag gct gtg cat     432
Leu Asp Thr Lys Ala Arg His Gln Gln Lys His Asn Lys Ala Val His
    130                 135                 140
```

```
ctg gcc cag gca agc ttc cag atc gaa gct ttc ggc tcc aag ttc att      480
Leu Ala Gln Ala Ser Phe Gln Ile Glu Ala Phe Gly Ser Lys Phe Ile
145                 150                 155                 160 ctt gac ctc aca ctg aac aat ggt ttg cta tct tct gac tac gtg gag      528
Leu Asp Leu Thr Leu Asn Asn Gly Leu Leu Ser Ser Asp Tyr Val Glu
                165                 170                 175 atc cac tat gaa gac ggg aag cag atg tac tct aag ggt gga gag cac      576
Ile His Tyr Glu Asp Gly Lys Gln Met Tyr Ser Lys Gly Gly Glu His
            180                 185                 190 tgt tac tac cac gga agc atc aga ggc gtc aag gat tcc agg gtg gct      624
Cys Tyr Tyr His Gly Ser Ile Arg Gly Val Lys Asp Ser Arg Val Ala
        195                 200                 205 cta tcg acc tgc aat gga ctc cat ggc atg ttt gag gat gac acc ttt      672
Leu Ser Thr Cys Asn Gly Leu His Gly Met Phe Glu Asp Asp Thr Phe
    210                 215                 220 gtg tat atg ata gag cct ctg gaa ctg act gat gat gag aaa agc aca      720
Val Tyr Met Ile Glu Pro Leu Glu Leu Thr Asp Asp Glu Lys Ser Thr
225                 230                 235                 240 ggc cga ccg cac ata atc cag aaa acc ttg gca gga cag tat tct aag      768
Gly Arg Pro His Ile Ile Gln Lys Thr Leu Ala Gly Gln Tyr Ser Lys
                245                 250                 255 cag atg aag aat ctc agc aca gat ggc agt gac cag tgg cct ttg cta      816
Gln Met Lys Asn Leu Ser Thr Asp Gly Ser Asp Gln Trp Pro Leu Leu
            260                 265                 270 cct gaa tta caa tgg ctg aga aga agg aaa aga gcg gtc aat cca tct      864
Pro Glu Leu Gln Trp Leu Arg Arg Arg Lys Arg Ala Val Asn Pro Ser
        275                 280                 285 cgt ggt gtg ttt gaa gaa atg aag tat ttg gag ctt atg att gtt aat      912
Arg Gly Val Phe Glu Glu Met Lys Tyr Leu Glu Leu Met Ile Val Asn
    290                 295                 300 gat cac aag acg tat aag aag cac cgc tct tct cac gcg cat acc aac      960
Asp His Lys Thr Tyr Lys Lys His Arg Ser Ser His Ala His Thr Asn
305                 310                 315                 320 aac ttc gca aag tct gtg gtc aac ctt gta gat tct att tac aag gaa     1008
Asn Phe Ala Lys Ser Val Val Asn Leu Val Asp Ser Ile Tyr Lys Glu
                325                 330                 335 cag ctc aac acc agg gtt gtc ctg gtg gct gtc gag acc tgg acc gag     1056
Gln Leu Asn Thr Arg Val Val Leu Val Ala Val Glu Thr Trp Thr Glu
            340                 345                 350 aag gat cac att gac atc acc atc aac ccc gtg cag atg cta cat gac     1104
Lys Asp His Ile Asp Ile Thr Ile Asn Pro Val Gln Met Leu His Asp
        355                 360                 365 ttc tcc aag tac cgg cag cga atc aaa cag cac gct gac gcg gtc cac     1152
Phe Ser Lys Tyr Arg Gln Arg Ile Lys Gln His Ala Asp Ala Val His
    370                 375                 380 ctc atc tcg cgc gtg aca ttc cat tat aag aga agc agt ctg agt tac     1200
Leu Ile Ser Arg Val Thr Phe His Tyr Lys Arg Ser Ser Leu Ser Tyr
385                 390                 395                 400 ttt gga ggc gtg tgt tct cga ata aga ggg gtt ggt gtg aat gag tat     1248
Phe Gly Gly Val Cys Ser Arg Ile Arg Gly Val Gly Val Asn Glu Tyr
                405                 410                 415 ggt ctt cca atg gcg gtg gca caa gta tta tca cag agc ctg gct caa     1296
Gly Leu Pro Met Ala Val Ala Gln Val Leu Ser Gln Ser Leu Ala Gln
            420                 425                 430 aac ctt gga atc cag tgg gaa cct tcg agc agg aag cca aaa tgt gaa     1344
Asn Leu Gly Ile Gln Trp Glu Pro Ser Ser Arg Lys Pro Lys Cys Glu
        435                 440                 445 tgc ata gag tcc tgg ggc ggc tgc atc atg gaa gaa aca ggg gtg tcc     1392
Cys Ile Glu Ser Trp Gly Gly Cys Ile Met Glu Glu Thr Gly Val Ser
    450                 455                 460
```

```
cac tct cga aag ttc tca aag tgc agc att ttg gag tac aga gac ttt      1440
His Ser Arg Lys Phe Ser Lys Cys Ser Ile Leu Glu Tyr Arg Asp Phe
465                 470                 475                 480 tta cag aga ggt ggc gga gca tgt ctt ttc aat agg cca act aag ctg      1488
Leu Gln Arg Gly Gly Gly Ala Cys Leu Phe Asn Arg Pro Thr Lys Leu
                    485                 490                 495 ttt gag ccc acg gaa tgt gga aat gga tat gtg gag gcc ggg gag gaa      1536
Phe Glu Pro Thr Glu Cys Gly Asn Gly Tyr Val Glu Ala Gly Glu Glu
                500                 505                 510 tgc gac tgt ggt ttc cat gtg gaa tgc tat gga gtt tgc tgt aag aag      1584
Cys Asp Cys Gly Phe His Val Glu Cys Tyr Gly Val Cys Cys Lys Lys
            515                 520                 525 tgt tcg ctc tcc aat ggg gcc cac tgc agt gac ggc ccc tgc tgt aac      1632
Cys Ser Leu Ser Asn Gly Ala His Cys Ser Asp Gly Pro Cys Cys Asn
530                 535                 540 aac acc tca tgt ctt ttt cag tca cga ggg tat gaa tgt cgg gat gcc      1680
Asn Thr Ser Cys Leu Phe Gln Ser Arg Gly Tyr Glu Cys Arg Asp Ala
545                 550                 555                 560 gta aac agc tgt gat atc acc gag tac tgc act gga gac tct ggc cag      1728
Val Asn Ser Cys Asp Ile Thr Glu Tyr Cys Thr Gly Asp Ser Gly Gln
                565                 570                 575 tgc cca ccg aac ctc cat aaa caa gat ggc tat agc tgc aat caa aat      1776
Cys Pro Pro Asn Leu His Lys Gln Asp Gly Tyr Ser Cys Asn Gln Asn
                580                 585                 590 cag ggt cgc tgc tac aat ggc gag tgc aag aca agg gac aat caa tgc      1824
Gln Gly Arg Cys Tyr Asn Gly Glu Cys Lys Thr Arg Asp Asn Gln Cys
            595                 600                 605 cag tac atc tgg ggg aca aag gct gcg ggg tca gac aag ttc tgc tat      1872
Gln Tyr Ile Trp Gly Thr Lys Ala Ala Gly Ser Asp Lys Phe Cys Tyr
610                 615                 620 gaa aag ctg aac acg gaa ggc acc gag aag ggc aat tgt gga aag gat      1920
Glu Lys Leu Asn Thr Glu Gly Thr Glu Lys Gly Asn Cys Gly Lys Asp
625                 630                 635                 640 gga gac cgg tgg atc ccg tgc agc aag cat gat gtg ttc tgt gga ttt      1968
Gly Asp Arg Trp Ile Pro Cys Ser Lys His Asp Val Phe Cys Gly Phe
                645                 650                 655 ctg ctt tgc acc aat ctt acc cga gct cca cgt atc ggt caa ctt caa      2016
Leu Leu Cys Thr Asn Leu Thr Arg Ala Pro Arg Ile Gly Gln Leu Gln
                660                 665                 670 gga gag atc atc ccg act tcc ttc tat cat caa ggc cga gtg att gac      2064
Gly Glu Ile Ile Pro Thr Ser Phe Tyr His Gln Gly Arg Val Ile Asp
            675                 680                 685 tgc agt ggt gct cat gta gtt tta gac gat gat aca gac gtg ggt tac      2112
Cys Ser Gly Ala His Val Val Leu Asp Asp Asp Thr Asp Val Gly Tyr
690                 695                 700 gtt gaa gat ggg act ccg tgt ggc ccc tcc atg atg tgc tta gat cgg      2160
Val Glu Asp Gly Thr Pro Cys Gly Pro Ser Met Met Cys Leu Asp Arg
705                 710                 715                 720 aag tgc cta cag att caa gcc ctg aat atg agc agc tgc cca ctt gac      2208
Lys Cys Leu Gln Ile Gln Ala Leu Asn Met Ser Ser Cys Pro Leu Asp
                725                 730                 735 tca agg ggt aaa gtc tgc tcc ggc cac ggg gtg tgt agc aac gaa gcc      2256
Ser Arg Gly Lys Val Cys Ser Gly His Gly Val Cys Ser Asn Glu Ala
                740                 745                 750 acc tgc atc tgt gat ttc act tgg gca ggc aca gac tgc agc atc cgg      2304
Thr Cys Ile Cys Asp Phe Thr Trp Ala Gly Thr Asp Cys Ser Ile Arg
            755                 760                 765 gat cca gtt cgg aac ccc aac ccc cct aag gat gaa ggc cct aag ggt      2352
Asp Pro Val Arg Asn Pro Asn Pro Pro Lys Asp Glu Gly Pro Lys Gly
770                 775                 780
```

-continued

```
cct agc gcc acc aat ctc ata ata ggc tcc atc gct ggt gcc atc ctg    2400
Pro Ser Ala Thr Asn Leu Ile Ile Gly Ser Ile Ala Gly Ala Ile Leu
785                 790                 795                 800 gta gca gct att gtc ctt ggg ggc aca ggc tgg gga ttt aaa aac gtc    2448
Val Ala Ala Ile Val Leu Gly Gly Thr Gly Trp Gly Phe Lys Asn Val
            805                 810                 815 aag aag agg aga ttc gat ccc act cag caa ggc ccc atc tga            2490
Lys Lys Arg Arg Phe Asp Pro Thr Gln Gln Gly Pro Ile
820                 825
```

<210> SEQ ID NO 27
<211> LENGTH: 829
<212> TYPE: PRT
<213> ORGANISM: Mus musculus

<400> SEQUENCE: 27

```
Met Lys Pro Pro Gly Ser Ile Ser Arg Arg Pro Thr Leu Thr Gly Cys
1               5                   10                  15

Ser Leu Pro Gly Ala Ser Cys Gly Pro Gly Arg Cys Pro Ala Gly Pro
                20                  25                  30

Val Pro Ala Arg Ala Pro Pro Cys Arg Leu Leu Val Leu Leu Leu
            35                  40                  45

Leu Pro Ala Leu Ala Thr Ser Ser Arg Pro Arg Ala Arg Gly Ala Ala
50                  55                  60

Ala Pro Ser Ala Pro His Trp Asn Glu Thr Ala Glu Lys Thr Leu Gly
65                  70                  75                  80

Val Leu Ala Asp Glu Asp Asn Thr Leu Gln Gln Asn Ser Ser Ser Arg
                85                  90                  95

Asn Thr Ser Tyr Ser Ser Ala Val Gln Lys Glu Ile Thr Leu Pro Ser
            100                 105                 110

Arg Leu Val Tyr Tyr Ile Asn Gln Asp Ser Glu Ser Pro Tyr His Val
        115                 120                 125

Leu Asp Thr Lys Ala Arg His Gln Gln Lys His Asn Lys Ala Val His
130                 135                 140

Leu Ala Gln Ala Ser Phe Gln Ile Glu Ala Phe Gly Ser Lys Phe Ile
145                 150                 155                 160

Leu Asp Leu Thr Leu Asn Asn Gly Leu Leu Ser Ser Asp Tyr Val Glu
                165                 170                 175

Ile His Tyr Glu Asp Gly Lys Gln Met Tyr Ser Lys Gly Gly Glu His
            180                 185                 190

Cys Tyr Tyr His Gly Ser Ile Arg Gly Val Lys Asp Ser Arg Val Ala
        195                 200                 205

Leu Ser Thr Cys Asn Gly Leu His Gly Met Phe Glu Asp Asp Thr Phe
210                 215                 220

Val Tyr Met Ile Glu Pro Leu Glu Leu Thr Asp Asp Glu Lys Ser Thr
225                 230                 235                 240

Gly Arg Pro His Ile Ile Gln Lys Thr Leu Ala Gly Gln Tyr Ser Lys
                245                 250                 255

Gln Met Lys Asn Leu Ser Thr Asp Gly Ser Asp Gln Trp Pro Leu Leu
            260                 265                 270

Pro Glu Leu Gln Trp Leu Arg Arg Arg Lys Arg Ala Val Asn Pro Ser
        275                 280                 285

Arg Gly Val Phe Glu Glu Met Lys Tyr Leu Glu Leu Met Ile Val Asn
290                 295                 300

Asp His Lys Thr Tyr Lys Lys His Arg Ser Ser His Ala His Thr Asn
305                 310                 315                 320
```

-continued

```
Asn Phe Ala Lys Ser Val Val Asn Leu Val Asp Ser Ile Tyr Lys Glu
                325                 330                 335

Gln Leu Asn Thr Arg Val Val Leu Val Ala Val Glu Thr Trp Thr Glu
            340                 345                 350

Lys Asp His Ile Asp Ile Thr Ile Asn Pro Val Gln Met Leu His Asp
        355                 360                 365

Phe Ser Lys Tyr Arg Gln Arg Ile Lys Gln His Ala Asp Ala Val His
    370                 375                 380

Leu Ile Ser Arg Val Thr Phe His Tyr Lys Arg Ser Ser Leu Ser Tyr
385                 390                 395                 400

Phe Gly Gly Val Cys Ser Arg Ile Arg Gly Val Gly Val Asn Glu Tyr
                405                 410                 415

Gly Leu Pro Met Ala Val Ala Gln Val Leu Ser Gln Ser Leu Ala Gln
            420                 425                 430

Asn Leu Gly Ile Gln Trp Glu Pro Ser Ser Arg Lys Pro Lys Cys Glu
        435                 440                 445

Cys Ile Glu Ser Trp Gly Gly Cys Ile Met Glu Glu Thr Gly Val Ser
    450                 455                 460

His Ser Arg Lys Phe Ser Lys Cys Ser Ile Leu Glu Tyr Arg Asp Phe
465                 470                 475                 480

Leu Gln Arg Gly Gly Gly Ala Cys Leu Phe Asn Arg Pro Thr Lys Leu
                485                 490                 495

Phe Glu Pro Thr Glu Cys Gly Asn Gly Tyr Val Glu Ala Gly Glu Glu
            500                 505                 510

Cys Asp Cys Gly Phe His Val Glu Cys Tyr Gly Val Cys Cys Lys Lys
        515                 520                 525

Cys Ser Leu Ser Asn Gly Ala His Cys Ser Asp Gly Pro Cys Cys Asn
    530                 535                 540

Asn Thr Ser Cys Leu Phe Gln Ser Arg Gly Tyr Glu Cys Arg Asp Ala
545                 550                 555                 560

Val Asn Ser Cys Asp Ile Thr Glu Tyr Cys Thr Gly Asp Ser Gly Gln
                565                 570                 575

Cys Pro Pro Asn Leu His Lys Gln Asp Gly Tyr Ser Cys Asn Gln Asn
            580                 585                 590

Gln Gly Arg Cys Tyr Asn Gly Glu Cys Lys Thr Arg Asp Asn Gln Cys
        595                 600                 605

Gln Tyr Ile Trp Gly Thr Lys Ala Ala Gly Ser Asp Lys Phe Cys Tyr
    610                 615                 620

Glu Lys Leu Asn Thr Glu Gly Thr Glu Lys Gly Asn Cys Gly Lys Asp
625                 630                 635                 640

Gly Asp Arg Trp Ile Pro Cys Ser Lys His Asp Val Phe Cys Gly Phe
                645                 650                 655

Leu Leu Cys Thr Asn Leu Thr Arg Ala Pro Arg Ile Gly Gln Leu Gln
            660                 665                 670

Gly Glu Ile Ile Pro Thr Ser Phe Tyr His Gln Gly Arg Val Ile Asp
        675                 680                 685

Cys Ser Gly Ala His Val Val Leu Asp Asp Thr Asp Val Gly Tyr
    690                 695                 700

Val Glu Asp Gly Thr Pro Cys Gly Pro Ser Met Met Cys Leu Asp Arg
705                 710                 715                 720

Lys Cys Leu Gln Ile Gln Ala Leu Asn Met Ser Ser Cys Pro Leu Asp
                725                 730                 735
```

```
Ser Arg Gly Lys Val Cys Ser Gly His Gly Val Cys Ser Asn Glu Ala
            740                 745                 750

Thr Cys Ile Cys Asp Phe Thr Trp Ala Gly Thr Asp Cys Ser Ile Arg
            755                 760                 765

Asp Pro Val Arg Asn Pro Asn Pro Pro Lys Asp Glu Gly Pro Lys Gly
            770                 775                 780

Pro Ser Ala Thr Asn Leu Ile Ile Gly Ser Ile Ala Gly Ala Ile Leu
785                 790                 795                 800

Val Ala Ala Ile Val Leu Gly Gly Thr Gly Trp Gly Phe Lys Asn Val
                805                 810                 815

Lys Lys Arg Arg Phe Asp Pro Thr Gln Gln Gly Pro Ile
            820                 825
```

<210> SEQ ID NO 28
<211> LENGTH: 2499
<212> TYPE: DNA
<213> ORGANISM: Homo sapiens
<220> FEATURE:
<221> NAME/KEY: CDS
<222> LOCATION: (1)..(2496)

<400> SEQUENCE: 28

```
atg aag ccg ccc ggc agc agc tcg cgg cag ccg ccc ctg gcg ggc tgc      48
Met Lys Pro Pro Gly Ser Ser Ser Arg Gln Pro Pro Leu Ala Gly Cys
1               5                   10                  15 agc ctt gcc ggc gct tcc tgc ggc ccc caa cgc ggc ccc gcc ggc tcg      96
Ser Leu Ala Gly Ala Ser Cys Gly Pro Gln Arg Gly Pro Ala Gly Ser
                20                  25                  30 gtg cct gcc agc gcc ccg gcc cgc acg ccg ccc tgc cgc ctg ctt ctc     144
Val Pro Ala Ser Ala Pro Ala Arg Thr Pro Pro Cys Arg Leu Leu Leu
            35                  40                  45 gtc ctt ctc ctg ctg cct ccg ctc gcc gcc tcg tcc cgg ccc cgc gcc     192
Val Leu Leu Leu Leu Pro Pro Leu Ala Ala Ser Ser Arg Pro Arg Ala
50                  55                  60 tgg ggg gct gct gcg ccc agc gct ccg cat tgg aat gaa act gca gaa     240
Trp Gly Ala Ala Ala Pro Ser Ala Pro His Trp Asn Glu Thr Ala Glu
65                  70                  75                  80 aaa aat ttg gga gtc ctg gca gat gaa gac aat aca ttg caa cag aat     288
Lys Asn Leu Gly Val Leu Ala Asp Glu Asp Asn Thr Leu Gln Gln Asn
                85                  90                  95 agc agc agt aat atc agt tac agc aat gca atg cag aaa gaa atc aca     336
Ser Ser Ser Asn Ile Ser Tyr Ser Asn Ala Met Gln Lys Glu Ile Thr
            100                 105                 110 ctg cct tca aga ctc ata tat tac atc aac caa gac tcg gaa agc cct     384
Leu Pro Ser Arg Leu Ile Tyr Tyr Ile Asn Gln Asp Ser Glu Ser Pro
        115                 120                 125 tat cac gtt ctt gac aca aag gca aga cac cag caa aaa cat aat aag     432
Tyr His Val Leu Asp Thr Lys Ala Arg His Gln Gln Lys His Asn Lys
    130                 135                 140 gct gtc cat ctg gcc cag gca agc ttc cag att gaa gcc ttc ggc tcc     480
Ala Val His Leu Ala Gln Ala Ser Phe Gln Ile Glu Ala Phe Gly Ser
145                 150                 155                 160 aaa ttc att ctt gac ctc ata ctg aac aat ggt ttg ttg tct tct gat     528
Lys Phe Ile Leu Asp Leu Ile Leu Asn Asn Gly Leu Leu Ser Ser Asp
                165                 170                 175 tat gtg gag att cac tac gaa aat ggg aaa cca cag tac tct aag ggt     576
Tyr Val Glu Ile His Tyr Glu Asn Gly Lys Pro Gln Tyr Ser Lys Gly
            180                 185                 190
```

-continued

| | | |
|---|---|---|
| gga gag cac tgt tac tac cat gga agc atc aga ggc gtc aaa gac tcc<br>Gly Glu His Cys Tyr Tyr His Gly Ser Ile Arg Gly Val Lys Asp Ser<br>          195                 200               205 | 624 | |
| aag gtg gct ctg tca acc tgc aat gga ctt cat ggc atg ttt gaa gat<br>Lys Val Ala Leu Ser Thr Cys Asn Gly Leu His Gly Met Phe Glu Asp<br>210                 215                 220 | 672 | |
| gat acc ttc gtg tat atg ata gag cca cta gag ctg gtt cat gat gag<br>Asp Thr Phe Val Tyr Met Ile Glu Pro Leu Glu Leu Val His Asp Glu<br>225                 230                 235               240 | 720 | |
| aaa agc aca ggt cga cca cat ata atc cag aaa acc ttg gca gga cag<br>Lys Ser Thr Gly Arg Pro His Ile Ile Gln Lys Thr Leu Ala Gly Gln<br>          245                 250               255 | 768 | |
| tat tct aag caa atg aag aat ctc act atg gaa aga ggt gac cag tgg<br>Tyr Ser Lys Gln Met Lys Asn Leu Thr Met Glu Arg Gly Asp Gln Trp<br>          260                 265               270 | 816 | |
| ccc ttt ctc tct gaa tta cag tgg ttg aaa aga agg aag aga gca gtg<br>Pro Phe Leu Ser Glu Leu Gln Trp Leu Lys Arg Arg Lys Arg Ala Val<br>          275                 280               285 | 864 | |
| aat cca tca cgt ggt ata ttt gaa gaa atg aaa tat ttg gaa ctt atg<br>Asn Pro Ser Arg Gly Ile Phe Glu Glu Met Lys Tyr Leu Glu Leu Met<br>290                 295                 300 | 912 | |
| att gtt aat gat cac aaa acg tat aag aag cat cgc tct tct cat gca<br>Ile Val Asn Asp His Lys Thr Tyr Lys Lys His Arg Ser Ser His Ala<br>305                 310                 315               320 | 960 | |
| cat acc aac aac ttt gca aag tcc gtg gtc aac ctt gtg gat tct att<br>His Thr Asn Asn Phe Ala Lys Ser Val Val Asn Leu Val Asp Ser Ile<br>                         325               330               335 | 1008 | |
| tac aag gag cag ctc aac acc agg gtt gtc ctg gtg gct gta gag acc<br>Tyr Lys Glu Gln Leu Asn Thr Arg Val Val Leu Val Ala Val Glu Thr<br>          340                 345               350 | 1056 | |
| tgg act gag aag gat cag att gac atc acc acc aac cct gtg cag atg<br>Trp Thr Glu Lys Asp Gln Ile Asp Ile Thr Thr Asn Pro Val Gln Met<br>          355                 360               365 | 1104 | |
| ctc cat gag ttc tca aaa tac cgg cag cgc att aag cag cat gct gat<br>Leu His Glu Phe Ser Lys Tyr Arg Gln Arg Ile Lys Gln His Ala Asp<br>370                 375                 380 | 1152 | |
| gct gtg cac ctc atc tcg cgg gtg aca ttt cac tat aag aga agc agt<br>Ala Val His Leu Ile Ser Arg Val Thr Phe His Tyr Lys Arg Ser Ser<br>385                 390                 395               400 | 1200 | |
| ctg agt tac ttt gga ggt gtc tgt tct cgc aca aga gga gtt ggt gtg<br>Leu Ser Tyr Phe Gly Gly Val Cys Ser Arg Thr Arg Gly Val Gly Val<br>          405                 410               415 | 1248 | |
| aat gag tat ggt ctt cca atg gca gtg gca caa gta tta tcg cag agc<br>Asn Glu Tyr Gly Leu Pro Met Ala Val Ala Gln Val Leu Ser Gln Ser<br>          420                 425               430 | 1296 | |
| ctg gct caa aac ctt gga atc caa tgg gaa cct tct agc aga aag cca<br>Leu Ala Gln Asn Leu Gly Ile Gln Trp Glu Pro Ser Ser Arg Lys Pro<br>          435                 440               445 | 1344 | |
| aaa tgt gac tgc aca gaa tcc tgg ggt ggc tgc atc atg gag gaa aca<br>Lys Cys Asp Cys Thr Glu Ser Trp Gly Gly Cys Ile Met Glu Glu Thr<br>450                 455                 460 | 1392 | |
| ggg gtg tcc cat tct cga aaa ttt tca aag tgc agc att ttg gag tat<br>Gly Val Ser His Ser Arg Lys Phe Ser Lys Cys Ser Ile Leu Glu Tyr<br>465                 470                 475               480 | 1440 | |
| aga gac ttt tta cag aga gga ggt gga gcc tgc ctt ttc aac agg cca<br>Arg Asp Phe Leu Gln Arg Gly Gly Gly Ala Cys Leu Phe Asn Arg Pro<br>          485                 490               495 | 1488 | |
| aca aag cta ttt gag ccc acg gaa tgt gga aat gga tac gtg gaa gct<br>Thr Lys Leu Phe Glu Pro Thr Glu Cys Gly Asn Gly Tyr Val Glu Ala<br>          500                 505               510 | 1536 | |

|  |  |
|---|---|
| ggg gag gag tgt gat tgt ggt ttt cat gtg aaa tgc tat gga tta tgc<br>Gly Glu Glu Cys Asp Cys Gly Phe His Val Glu Cys Tyr Gly Leu Cys<br>        515                    520                  525 | 1584 |
| tgt aag aaa tgt tcc ctc tcc aac ggg gct cac tgc agc gac ggg ccc<br>Cys Lys Lys Cys Ser Leu Ser Asn Gly Ala His Cys Ser Asp Gly Pro<br>530                    535                    540 | 1632 |
| tgc tgt aac aat acc tca tgt ctt ttt cag cca cga ggg tat gaa tgc<br>Cys Cys Asn Asn Thr Ser Cys Leu Phe Gln Pro Arg Gly Tyr Glu Cys<br>545                    550                    555                    560 | 1680 |
| cgg gat gct gtg aac gag tgt gat att act gaa tat tgt act gga gac<br>Arg Asp Ala Val Asn Glu Cys Asp Ile Thr Glu Tyr Cys Thr Gly Asp<br>        565                    570                  575 | 1728 |
| tct ggt cag tgc cca cca aat ctt cat aag caa gac gga tat gca tgc<br>Ser Gly Gln Cys Pro Pro Asn Leu His Lys Gln Asp Gly Tyr Ala Cys<br>                580                    585                    590 | 1776 |
| aat caa aat cag ggc cgc tgc tac aat ggc gag tgc aag acc aga gac<br>Asn Gln Asn Gln Gly Arg Cys Tyr Asn Gly Glu Cys Lys Thr Arg Asp<br>595                    600                    605 | 1824 |
| aac cag tgt cag tac atc tgg gga aca aag gct gca ggg tct gac aag<br>Asn Gln Cys Gln Tyr Ile Trp Gly Thr Lys Ala Ala Gly Ser Asp Lys<br>610                    615                    620 | 1872 |
| ttc tgc tat gaa aag ctg aat aca gaa ggc act gag aag gga aac tgc<br>Phe Cys Tyr Glu Lys Leu Asn Thr Glu Gly Thr Glu Lys Gly Asn Cys<br>625                    630                    635                    640 | 1920 |
| ggg aag gat gga gac cgg tgg att cag tgc agc aaa cat gat gtg ttc<br>Gly Lys Asp Gly Asp Arg Trp Ile Gln Cys Ser Lys His Asp Val Phe<br>                645                    650                  655 | 1968 |
| tgt gga ttc tta ctc tgt acc aat ctt act cga gct cca cgt att ggt<br>Cys Gly Phe Leu Leu Cys Thr Asn Leu Thr Arg Ala Pro Arg Ile Gly<br>              660                    665                  670 | 2016 |
| caa ctt cag ggt gag atc att cca act tcc ttc tac cat caa ggc cgg<br>Gln Leu Gln Gly Glu Ile Ile Pro Thr Ser Phe Tyr His Gln Gly Arg<br>      675                    680                    685 | 2064 |
| gtg att gac tgc agt ggt gcc cat gta gtt tta gat gat gat acg gat<br>Val Ile Asp Cys Ser Gly Ala His Val Val Leu Asp Asp Asp Thr Asp<br>690                    695                    700 | 2112 |
| gtg ggc tat gta gaa gat gga acg cca tgt ggc ccg tct atg atg tgt<br>Val Gly Tyr Val Glu Asp Gly Thr Pro Cys Gly Pro Ser Met Met Cys<br>705                    710                    715                    720 | 2160 |
| tta gat cgg aag tgc cta caa att caa gcc cta aat atg agc agc tgt<br>Leu Asp Arg Lys Cys Leu Gln Ile Gln Ala Leu Asn Met Ser Ser Cys<br>                725                    730                  735 | 2208 |
| cca ctc gat tcc aag ggt aaa gtc tgt tcg ggc cat ggg gtg tgt agt<br>Pro Leu Asp Ser Lys Gly Lys Val Cys Ser Gly His Gly Val Cys Ser<br>                740                    745                  750 | 2256 |
| aat gaa gcc acc tgc att tgt gat ttc acc tgg gca ggg aca gat tgc<br>Asn Glu Ala Thr Cys Ile Cys Asp Phe Thr Trp Ala Gly Thr Asp Cys<br>755                    760                    765 | 2304 |
| agt atc cgg gat cca gtt agg aac ctt cac ccc ccc aag gat gaa gga<br>Ser Ile Arg Asp Pro Val Arg Asn Leu His Pro Pro Lys Asp Glu Gly<br>770                    775                    780 | 2352 |
| ccc aag ggt cct agt gcc acc aat ctc ata ata ggc tcc atc gct ggt<br>Pro Lys Gly Pro Ser Ala Thr Asn Leu Ile Ile Gly Ser Ile Ala Gly<br>785                    790                    795                    800 | 2400 |
| gcc atc ctg gta gca gct att gtc ctt ggg ggc aca ggc tgg gga ttt<br>Ala Ile Leu Val Ala Ala Ile Val Leu Gly Gly Thr Gly Trp Gly Phe<br>                805                    810                  815 | 2448 |

```
aaa aat gtc aag aag aga agg ttc gat cct act cag caa ggc ccc atc    2496
Lys Asn Val Lys Lys Arg Arg Phe Asp Pro Thr Gln Gln Gly Pro Ile
            820             825                 830 tga                                                                2499
```

<210> SEQ ID NO 29
<211> LENGTH: 832
<212> TYPE: PRT
<213> ORGANISM: Homo sapiens

<400> SEQUENCE: 29

```
Met Lys Pro Pro Gly Ser Ser Arg Gln Pro Pro Leu Ala Gly Cys
1               5                   10                  15

Ser Leu Ala Gly Ala Ser Cys Gly Pro Gln Arg Gly Pro Ala Gly Ser
                20                  25                  30

Val Pro Ala Ser Ala Pro Ala Arg Thr Pro Pro Cys Arg Leu Leu Leu
            35                  40                  45

Val Leu Leu Leu Leu Pro Pro Leu Ala Ala Ser Ser Arg Pro Arg Ala
50                  55                  60

Trp Gly Ala Ala Ala Pro Ser Ala Pro His Trp Asn Glu Thr Ala Glu
65                  70                  75                  80

Lys Asn Leu Gly Val Leu Ala Asp Glu Asp Asn Thr Leu Gln Gln Asn
                85                  90                  95

Ser Ser Ser Asn Ile Ser Tyr Ser Asn Ala Met Gln Lys Glu Ile Thr
            100                 105                 110

Leu Pro Ser Arg Leu Ile Tyr Tyr Ile Asn Gln Asp Ser Glu Ser Pro
        115                 120                 125

Tyr His Val Leu Asp Thr Lys Ala Arg His Gln Gln Lys His Asn Lys
130                 135                 140

Ala Val His Leu Ala Gln Ala Ser Phe Gln Ile Glu Ala Phe Gly Ser
145                 150                 155                 160

Lys Phe Ile Leu Asp Leu Ile Leu Asn Asn Gly Leu Leu Ser Ser Asp
                165                 170                 175

Tyr Val Glu Ile His Tyr Glu Asn Gly Lys Pro Gln Tyr Ser Lys Gly
            180                 185                 190

Gly Glu His Cys Tyr Tyr His Gly Ser Ile Arg Gly Val Lys Asp Ser
        195                 200                 205

Lys Val Ala Leu Ser Thr Cys Asn Gly Leu His Gly Met Phe Glu Asp
210                 215                 220

Asp Thr Phe Val Tyr Met Ile Glu Pro Leu Glu Leu Val His Asp Glu
225                 230                 235                 240

Lys Ser Thr Gly Arg Pro His Ile Ile Gln Lys Thr Leu Ala Gly Gln
                245                 250                 255

Tyr Ser Lys Gln Met Lys Asn Leu Thr Met Glu Arg Gly Asp Gln Trp
            260                 265                 270

Pro Phe Leu Ser Glu Leu Gln Trp Leu Lys Arg Arg Lys Arg Ala Val
        275                 280                 285

Asn Pro Ser Arg Gly Ile Phe Glu Glu Met Lys Tyr Leu Glu Leu Met
290                 295                 300

Ile Val Asn Asp His Lys Thr Tyr Lys Lys His Arg Ser Ser His Ala
305                 310                 315                 320

His Thr Asn Asn Phe Ala Lys Ser Val Val Asn Leu Val Asp Ser Ile
                325                 330                 335

Tyr Lys Glu Gln Leu Asn Thr Arg Val Val Leu Val Ala Val Glu Thr
            340                 345                 350
```

-continued

```
Trp Thr Glu Lys Asp Gln Ile Asp Ile Thr Thr Asn Pro Val Gln Met
            355                 360                 365
Leu His Glu Phe Ser Lys Tyr Arg Gln Arg Ile Lys Gln His Ala Asp
        370                 375                 380
Ala Val His Leu Ile Ser Arg Val Thr Phe His Tyr Lys Arg Ser Ser
385                 390                 395                 400
Leu Ser Tyr Phe Gly Gly Val Cys Ser Arg Thr Arg Gly Val Gly Val
                405                 410                 415
Asn Glu Tyr Gly Leu Pro Met Ala Val Ala Gln Val Leu Ser Gln Ser
            420                 425                 430
Leu Ala Gln Asn Leu Gly Ile Gln Trp Glu Pro Ser Ser Arg Lys Pro
        435                 440                 445
Lys Cys Asp Cys Thr Glu Ser Trp Gly Gly Cys Ile Met Glu Glu Thr
    450                 455                 460
Gly Val Ser His Ser Arg Lys Phe Ser Lys Cys Ser Ile Leu Glu Tyr
465                 470                 475                 480
Arg Asp Phe Leu Gln Arg Gly Gly Ala Cys Leu Phe Asn Arg Pro
                485                 490                 495
Thr Lys Leu Phe Glu Pro Thr Glu Cys Gly Asn Gly Tyr Val Glu Ala
            500                 505                 510
Gly Glu Glu Cys Asp Cys Gly Phe His Val Glu Cys Tyr Gly Leu Cys
        515                 520                 525
Cys Lys Lys Cys Ser Leu Ser Asn Gly Ala His Cys Ser Asp Gly Pro
    530                 535                 540
Cys Cys Asn Asn Thr Ser Cys Leu Phe Gln Pro Arg Gly Tyr Glu Cys
545                 550                 555                 560
Arg Asp Ala Val Asn Glu Cys Asp Ile Thr Glu Tyr Cys Thr Gly Asp
                565                 570                 575
Ser Gly Gln Cys Pro Pro Asn Leu His Lys Gln Asp Gly Tyr Ala Cys
            580                 585                 590
Asn Gln Asn Gln Gly Arg Cys Tyr Asn Gly Glu Cys Lys Thr Arg Asp
        595                 600                 605
Asn Gln Cys Gln Tyr Ile Trp Gly Thr Lys Ala Ala Gly Ser Asp Lys
    610                 615                 620
Phe Cys Tyr Glu Lys Leu Asn Thr Glu Gly Thr Glu Lys Gly Asn Cys
625                 630                 635                 640
Gly Lys Asp Gly Asp Arg Trp Ile Gln Cys Ser Lys His Asp Val Phe
                645                 650                 655
Cys Gly Phe Leu Leu Cys Thr Asn Leu Thr Arg Ala Pro Arg Ile Gly
            660                 665                 670
Gln Leu Gln Gly Glu Ile Ile Pro Thr Ser Phe Tyr His Gln Gly Arg
        675                 680                 685
Val Ile Asp Cys Ser Gly Ala His Val Val Leu Asp Asp Thr Asp
    690                 695                 700
Val Gly Tyr Val Glu Asp Gly Thr Pro Cys Gly Pro Ser Met Met Cys
705                 710                 715                 720
Leu Asp Arg Lys Cys Leu Gln Ile Gln Ala Leu Asn Met Ser Ser Cys
                725                 730                 735
Pro Leu Asp Ser Lys Gly Lys Val Cys Ser Gly His Gly Val Cys Ser
            740                 745                 750
Asn Glu Ala Thr Cys Ile Cys Asp Phe Thr Trp Ala Gly Thr Asp Cys
        755                 760                 765
```

-continued

```
Ser Ile Arg Asp Pro Val Arg Asn Leu His Pro Pro Lys Asp Glu Gly
        770                 775                 780

Pro Lys Gly Pro Ser Ala Thr Asn Leu Ile Ile Gly Ser Ile Ala Gly
785                 790                 795                 800

Ala Ile Leu Val Ala Ala Ile Val Leu Gly Gly Thr Gly Trp Gly Phe
                    805                 810                 815

Lys Asn Val Lys Lys Arg Arg Phe Asp Pro Thr Gln Gln Gly Pro Ile
                820                 825                 830
```

<210> SEQ ID NO 30
<211> LENGTH: 37
<212> TYPE: DNA
<213> ORGANISM: Artificial Sequence
<220> FEATURE:
<223> OTHER INFORMATION: primer

<400> SEQUENCE: 30
ccggtcgacc accatggaac tccgacccg aggctgg          37

<210> SEQ ID NO 31
<211> LENGTH: 32
<212> TYPE: DNA
<213> ORGANISM: Artificial Sequence
<220> FEATURE:
<223> OTHER INFORMATION: primer

<400> SEQUENCE: 31
ccgaattctt accgccacct gggcctggct gc              32

<210> SEQ ID NO 32
<211> LENGTH: 35
<212> TYPE: DNA
<213> ORGANISM: Artificial Sequence
<220> FEATURE:
<223> OTHER INFORMATION: primer

<400> SEQUENCE: 32
ccgctcgagc caccatgaag cctttcata ctgcc            35

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
tccgaattct tattgtttgt aggtccgtgg                 30

<210> SEQ ID NO 34
<211> LENGTH: 36
<212> TYPE: DNA
<213> ORGANISM: Artificial Sequence
<220> FEATURE:
<223> OTHER INFORMATION: primer

<400> SEQUENCE: 34
ccgctcgagc caccatgttg gctgcaaggc tggtgt          36

<210> SEQ ID NO 35
<211> LENGTH: 31
<212> TYPE: DNA
<213> ORGANISM: Artificial Sequence
<220> FEATURE:
<223> OTHER INFORMATION: primer

```
<400> SEQUENCE: 35
ccggatatct catttctttc tgttgcctcc a                                31

<210> SEQ ID NO 36
<211> LENGTH: 34
<212> TYPE: DNA
<213> ORGANISM: Artificial Sequence
<220> FEATURE:
<223> OTHER INFORMATION: primer

<400> SEQUENCE: 36
ccgctcgagc caccatgagc acctcgtctg cgcg                             34

<210> SEQ ID NO 37
<211> LENGTH: 29
<212> TYPE: DNA
<213> ORGANISM: Artificial Sequence
<220> FEATURE:
<223> OTHER INFORMATION: primer

<400> SEQUENCE: 37
tccgttaact taatagtcat catagttca                                   29

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
agctcattac tgtatattta                                             20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
gctatatttc ataagtcatc                                             20

<210> SEQ ID NO 40
<211> LENGTH: 26
<212> TYPE: DNA
<213> ORGANISM: Artificial Sequence
<220> FEATURE:
<223> OTHER INFORMATION: primer

<400> SEQUENCE: 40
ctcgggaagc gcgccattgt gttggt                                      26

<210> SEQ ID NO 41
<211> LENGTH: 34
<212> TYPE: DNA
<213> ORGANISM: Artificial Sequence
<220> FEATURE:
<223> OTHER INFORMATION: primer

<400> SEQUENCE: 41
ccgctcgagc caccatgcgt ttttgcctct tctc                             34
```

<210> SEQ ID NO 42
<211> LENGTH: 28
<212> TYPE: DNA
<213> ORGANISM: Artificial Sequence
<220> FEATURE:
<223> OTHER INFORMATION: primer

<400> SEQUENCE: 42
cggaattctt attggttcac tctgtctg                                28

<210> SEQ ID NO 43
<211> LENGTH: 33
<212> TYPE: DNA
<213> ORGANISM: Artificial Sequence
<220> FEATURE:
<223> OTHER INFORMATION: primer

<400> SEQUENCE: 43
acgcgtcgac ccaccatgcc ccgctacgag ttg                           33

<210> SEQ ID NO 44
<211> LENGTH: 29
<212> TYPE: DNA
<213> ORGANISM: Artificial Sequence
<220> FEATURE:
<223> OTHER INFORMATION: primer

<400> SEQUENCE: 44
attgaattct cacttcttcc tcctctttg                                29

<210> SEQ ID NO 45
<211> LENGTH: 35
<212> TYPE: DNA
<213> ORGANISM: Artificial Sequence
<220> FEATURE:
<223> OTHER INFORMATION: primer

<400> SEQUENCE: 45
ccgctcgagc caccatgaag ccgcccggca gcatc                         35

<210> SEQ ID NO 46
<211> LENGTH: 29
<212> TYPE: DNA
<213> ORGANISM: Artificial Sequence
<220> FEATURE:
<223> OTHER INFORMATION: primer

<400> SEQUENCE: 46
cggaattctc agatggggcc ttgctgagt                                29

<210> SEQ ID NO 47
<211> LENGTH: 1254
<212> TYPE: DNA
<213> ORGANISM: Homo sapiens
<220> FEATURE:
<221> NAME/KEY: CDS
<222> LOCATION: (18)..(746)

<400> SEQUENCE: 47
ccgctcgagc cgcccag atg cag ttt cgc ctt ttc tcc ttt gcc ctc atc         50
                   Met Gln Phe Arg Leu Phe Ser Phe Ala Leu Ile
                    1               5                  10 att ctg aac tgc atg gat tac agc cac tgc caa ggc aac cga tgg aga        98
Ile Leu Asn Cys Met Asp Tyr Ser His Cys Gln Gly Asn Arg Trp Arg
        15                  20                  25

-continued

| | |
|---|---|
| cgc agt aag cga gct agt tat gta tca aat ccc att tgc aag ggt tgt<br>Arg Ser Lys Arg Ala Ser Tyr Val Ser Asn Pro Ile Cys Lys Gly Cys<br>30                       35                     40 | 146 |
| ttg tct tgt tca aag gac aat ggg tgt agc cga tgt caa cag aag ttg<br>Leu Ser Cys Ser Lys Asp Asn Gly Cys Ser Arg Cys Gln Gln Lys Leu<br>45                       50                     55 | 194 |
| ttc ttc ttc ctt cga aga gaa ggg atg cgc cag tat gga gag tgc ctg<br>Phe Phe Phe Leu Arg Arg Glu Gly Met Arg Gln Tyr Gly Glu Cys Leu<br>60                       65                     70                     75 | 242 |
| cat tcc tgc cca tcc ggg tac tat gga cac cga gcc cca gat atg aac<br>His Ser Cys Pro Ser Gly Tyr Tyr Gly His Arg Ala Pro Asp Met Asn<br>                     80                     85                     90 | 290 |
| aga tgt gca aga tgc aga ata gaa aac tgt gat tct tgc ttt agc aaa<br>Arg Cys Ala Arg Cys Arg Ile Glu Asn Cys Asp Ser Cys Phe Ser Lys<br>                     95                    100                  105 | 338 |
| gac ttt tgt acc aag tgc aaa gta ggc ttt tat ttg cat aga ggc cgt<br>Asp Phe Cys Thr Lys Cys Lys Val Gly Phe Tyr Leu His Arg Gly Arg<br>           110                    115                  120 | 386 |
| tgc ttt gat gaa tgt cca gat ggt ttt gca cca tta gaa gaa acc atg<br>Cys Phe Asp Glu Cys Pro Asp Gly Phe Ala Pro Leu Glu Glu Thr Met<br>125                       130                    135 | 434 |
| gaa tgt gtg gaa gga tgt gaa gtt ggt cat tgg agc gaa tgg gga act<br>Glu Cys Val Glu Gly Cys Glu Val Gly His Trp Ser Glu Trp Gly Thr<br>140                       145                    150                  155 | 482 |
| tgt agc aga aat aat cgc aca tgt gga ttt aaa tgg ggt ctg gaa acc<br>Cys Ser Arg Asn Asn Arg Thr Cys Gly Phe Lys Trp Gly Leu Glu Thr<br>                     160                    165                  170 | 530 |
| aga aca cgg caa att gtt aaa aag cca gtg aaa gac aca ata ctg tgt<br>Arg Thr Arg Gln Ile Val Lys Lys Pro Val Lys Asp Thr Ile Leu Cys<br>                     175                    180                  185 | 578 |
| cca acc att gct gaa tcc agg aga tgc aag atg aca atg agg cat tgt<br>Pro Thr Ile Ala Glu Ser Arg Arg Cys Lys Met Thr Met Arg His Cys<br>           190                    195                  200 | 626 |
| cca gga ggg aag aga aca cca aag gcg aag gag aag agg aac aag aaa<br>Pro Gly Gly Lys Arg Thr Pro Lys Ala Lys Glu Lys Arg Asn Lys Lys<br>205                       210                    215 | 674 |
| aag aaa agg aag ctg ata gaa agg gcc cag gag caa cac agc gtc ttc<br>Lys Lys Arg Lys Leu Ile Glu Arg Ala Gln Glu Gln His Ser Val Phe<br>220                       225                    230                  235 | 722 |
| cta gct aca gac aga gct aac caa taaaacaaga gatccggtag attttaggg<br>Leu Ala Thr Asp Arg Ala Asn Gln<br>                     240 | 776 |
| gttttgttt ttgcaaatgt gcacaaagct actctccact cctgcacact ggtgtgcagc | 836 |
| ctttgtgctg ctctgcccag tatctgttcc cagtaacatg gtgaaaggaa gcaccaccag | 896 |
| catggcccct gtgttattta tgctttgatt tgaatctgga gactgtgaag gcaggagtaa | 956 |
| gtgcacagcc cgtgacttgg ctcagtgtgt gctgagagaa tccgtccccg gcaccatgga | 1016 |
| catgctagag gtgtgaggct gcagaacacc gctggaggac ggacttgtgc ctatttatgt | 1076 |
| gaaagaagat gcttggcagg caatgcgcta ctcactcgtg acctttattt ctcacattgt | 1136 |
| gcattttcaa ggatatgttt gtgtggatat ctgcttagtg ttaccacatg gtattctcag | 1196 |
| catgttacct tcacactgtt gtgcgatgaa actgctttta gctgaggata tgctctgg | 1254 |

<210> SEQ ID NO 48
<211> LENGTH: 243
<212> TYPE: PRT
<213> ORGANISM: Homo sapiens

```
<400> SEQUENCE: 48

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Phe Leu Arg
    50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
                100                 105                 110

Cys Lys Val Gly Phe Tyr Leu His Arg Gly Arg Cys Phe Asp Glu Cys
            115                 120                 125

Pro Asp Gly Phe Ala Pro Leu Glu Glu Thr Met Glu Cys Val Glu Gly
    130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Leu Cys Pro Thr Ile Ala Glu
            180                 185                 190

Ser Arg Arg Cys Lys Met Thr Met Arg His Cys Pro Gly Gly Lys Arg
            195                 200                 205

Thr Pro Lys Ala Lys Glu Lys Arg Asn Lys Lys Lys Arg Lys Leu
    210                 215                 220

Ile Glu Arg Ala Gln Glu Gln His Ser Val Phe Leu Ala Thr Asp Arg
225                 230                 235                 240

Ala Asn Gln

<210> SEQ ID NO 49
<211> LENGTH: 29
<212> TYPE: DNA
<213> ORGANISM: Artificial Sequence
<220> FEATURE:
<223> OTHER INFORMATION: primer

<400> SEQUENCE: 49
ccgctcgagc cgcccagatg cagtttcgc                                              29
```

POLYPEPTIDE HAVING AN ACTIVITY TO SUPPORT PROLIFERATION OR SURVIVAL OF HEMATOPOIETIC STEM OR PROGENITOR CELLS

This application is a U.S. National Phase Application pursuant to 35 U.S.C. 371 of International Application No. PCT/JP03/05383, which was filed Apr. 25, 2003, claiming benefit of priority of U.S. application Ser. No. 60/376,001, filed April 26, 2002. The entire disclosure of each of the foregoing applications is incorporated herein by reference in its entirety.

BACKGROUND OF THE INVENTION

1. Field of the Invention

The present invention relates to a polypeptide having an activity to support proliferation or survival of hematopoietic stem cells or hematopoietic progenitor cells, a DNA coding the polypeptide, and a pharmaceutical composition comprising the polypeptide as active ingredient.

2. Description of the Related Art

Fully differentiated mature hematopoietic cells have limited short lives. Homeostasis of the blood is maintained due to supply of the mature blood cells caused by continuous differentiation of hematopoietic progenitor cells. The hematopoietic progenitor cells are giving rise from more undifferentiated hematopoietic stem cells. The hematopoietic stem cells have potential of differentiating into all of the differentiation lineages (totipotency) and have potential of self-renew with retaining the totipotency so as to supply the hematopoietic cells through life. That is, the hematopoietic stem cells are known to generate totipotent stem cells by the self-renew and to differentiate in parts to a variety of the mature blood cells through the hematopoietic progenitor cells.

This differentiation of the blood cells is regulated by a variety of cytokines. Erythropoietin is known to promote the differentiation of the erythrocytic lineages. G-CSF and thrombopoietin are also known to promote the differentiation of the neutrophils, and the megakaryocytes and the platelet productive cells, respectively. However, a factor required for the self-renew of the hematopoietic stem cell with retaining the totipotency has not been clear. Although SCF/MGF (Williams, D. E., *Cell*, 63: 167-174, 1990; Zsebo, K. M., *Cell*, 63: 213-224, 1990), SCGF (WO98/08869), and the like are reported as growth factors for the hematopoietic stem cells, none of them have potency to sufficiently retain the totipotency of the hematopoietic stem cells. Although attempts to culture the hematopoietic stem cells in the presence of combinations of known cytokines, a system for efficient amplification of the hematopoietic stem cells was not realized (Miller, C. L., *Proc. Natl. Acad. Sci. USA*, 94: 13648-13653, 1997; Yagi, M., *Proc. Natl. Acad. Sci. USA*, 96: 8126-8131, 1999; Shih, C. C., *Blood*, 94: 5 1623-1636, 1999).

On the other hand, attempts to allow the hematopoietic stem cells to survive or proliferate without differentiation by using stromal cells which supply an environment suitable for survival or proliferation of the hematopoietic stem cells were reported (Moore K. A., *Blood*, 89: 12, 4337-4347, 1997). In addition, WO99/03980 discloses a stromal cell line capable of supporting proliferation or survival of hematopoietic stem cells and hematopoietic progenitor cells, which are established from an AGM (Aorta-Gonad-Mesonephros) region of a fetal mouse.

It is postulated that there should be more peptides that efficiently facilitate hematopoietic stem cell and progenitor cell amplification by themselves or in combination with stromal cells or stimulating factors such as cytokines, in addition to known factors affecting hematopoietic cells.

SUMMARY OF THE INVENTION

Since the proliferation or survival of hematopoietic stem cells or hematopoietic progenitor cells in vitro can be supported by co-culture of stromal cells and hematopoietic stem cells and hematopoietic progenitor cells, the stromal cells are expected to produce factors supporting the proliferation or survival of hematopoietic stem cells or hematopoietic progenitor cells. An object of the present invention is to provide a factor supporting the proliferation or survival of hematopoietic stem cells or hematopoietic progenitor cells, which is derived from the stromal cells.

The inventor of the present invention has assumed that the mouse stromal cells produce factors supporting the proliferation or survival of hematopoietic stem cells or hematopoietic progenitor cells, as mentioned above. Attention is given that there are two kinds of stromal cells. One has a ability to support the proliferation or survival of hematopoietic stem cells or hematopoietic progenitor cells (hereafter sometimes referred to as "activity to support hematopoietic stem cells"). The other does not have the activity to support hematopoietic stem cells. The inventor of the present invention has assumed that this difference in the ability is due to the fact that expression of genes encoding the factors is increased in the supporting stromal cells and that the expression is low in non-supporting stromal cells. Thus the inventor thinks it can be found the factors supporting the proliferation or survival of hematopoietic stem cells or hematopoietic progenitor cells among the genes expressed higher in the supporting cells compared to in the non-supporting cells. In this context, the inventor has identified genes of which expressions are high in AGM-s3-A9 cell line which has the activity to support hematopoietic stem cells, and low or undetected in AGM-s3-A7 cell line which does not have the activity to support hematopoietic stem cells, and has determined the activities to support hematopoietic stem cells, of cells in which these gene groups are highly expressed. As a result, the present invention has been completed.

That is, the present invention provides the following.

(1) A DNA coding for a polypeptide of the following (A) or (B):

(A) a polypeptide which comprises an amino acid sequence selected from the group consisting of SEQ ID NO: 19, SEQ ID NO: 23 and SEQ ID NO: 25; or (B) a polypeptide which comprises an amino acid sequence including deletion, substitution or insertion of one or several amino acids in the amino acid sequence as defined in (A), and which has an activity to support proliferation or survival of hematopoietic stem cells or hematopoietic progenitor cells.

(2) The DNA according to (1), which is a DNA of the following (a) or (b):

(a) a DNA which comprises a nucleotide sequence selected from the group consisting of the nucleotide sequence of nucleotides 1 to 444 of SEQ ID NO: 18, the nucleotide sequence of nucleotides 630 to 1358 of SEQ ID NO: 22, nucleotides 132 to 506 of SEQ ID NO: 24, and the nucleotide sequence of nucleotides 18 to 746 of SEQ ID NO: 47; or (b) a DNA which is hybridizable with a DNA comprising the nucleotide sequence as defined in (a) or a prove prepared from said DNA, under the stringent condition, and which has an activity to support proliferation or survival of hematopoietic stem cells or hematopoietic progenitor cells.

(3) The DNA according to (2), the stringent condition is 6×SSC, 5× Denhardt, 0.5% SDS and 68° C. (SSC: 3 M NaCl, 0.3 M sodium citrate; 50× Denhardt: 1% BSA, 1% polyvinyl pyrrolidone, 1% Ficoll 400), or 6×SSC, 5× Denhardt, 0.5% SDS, 50% formamide and 42° C.

(4) A expression vector which comprises the DNA of any one of (1) to (3) in such a manner that the DNA can be expressed.

(5) A cell into which the DNA of any one of (1) to (3) is introduced in such a manner that the DNA can be expressed.

(6). A polypeptide which is an expression product of the DNA of any one of (1) to (3), the polypeptide having an activity to support proliferation or survival of hematopoietic stem cells or hematopoietic progenitor cells.

(7) The polypeptide according to (6), which comprises an amino acid sequence selected from the group consisting of SEQ ID NO: 19, SEQ ID NO: 23, SEQ ID NO: 25 and SEQ ID NO: 48, or an amino acid sequence including deletion, substitution or insertion of one or several amino acids in the amino acid sequence.

(8) The polypeptide according to (6) or (7), which is modified with one or more modifying agents selected from the group consisting of polyethylene glycol (PEG), dextran, poly (N-vinyl-pyrrolidone), polypropylene glycol homopoymer, copolymer of polypropylene oxide/ethylene oxide, polyoxyethylated polyol and polyvinyl alcohol.

(9) An monoclonal antibody which binds to the polypeptide of any one of (6) to (8).

(10) A method for supporting proliferation or survival of hematopoietic stem cells or hematopoietic progenitor cells, comprising the step of co-culturing stromal cells in which a DNA coding for a polypeptide of the following (A) or (B) is expressed, with hematopoietic stem cells or progenitor cells, (A) a polypeptide which comprises an amino acid sequence selected from the group consisting of SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and SEQ ID NO: 48; or (B) a polypeptide which comprises an amino acid sequence including deletion, substitution or insertion of one or several amino acids in the amino acid sequence as defined in (A), and which has an activity to support proliferation or survival of hematopoietic stem cells or hematopoietic progenitor cells.

(11) The method according to (10), wherein the DNA is a DNA of the following (a) or (b):

(a) a DNA which comprises a nucleotide sequence selected from the group consisting of the nucleotide sequence of nucleotides 1 to 1671 of SEQ ID NO: 8, the nucleotide sequence of nucleotides 1 to 1674 of SEQ ID NO: 10, the nucleotide sequence of nucleotides 1 to 366 of SEQ ID NO: 12, the nucleotide sequence of nucleotides 84 to 1121 of SEQ ID NO: 14, the nucleotide sequence of nucleotides 1 to 1035 of SEQ ID NO: 16, the nucleotide sequence of nucleotides 1 to 444 of SEQ ID NO: 18, the nucleotide sequence of nucleotides 1 to 444 of SEQ ID NO: 20, the nucleotide sequence of nucleotides 630 to 1358 of SEQ ID NO: 22, the nucleotide sequence of nucleotides 132 to 506 of SEQ ID NO: 24, the nucleotide sequence of nucleotides 1 to 2487 of SEQ ID NO: 26, and the nucleotide sequence of nucleotides 1 to 2496 of SEQ ID NO: 28, and nucleotides 18 to 746 of SEQ ID NO: 47; or (b) a DNA which is hybridizable with a DNA comprising the nucleotide sequence as defined in (a) or a prove prepared from said DNA, under the stringent condition, and which has an activity to support proliferation or survival of hematopoietic stem cells or hematopoietic progenitor cells.

(12) A method for supporting proliferation or survival of hematopoietic stem cells or hematopoietic progenitor cells, comprising the step of culturing hematopoietic stem cells or progenitor cells in the presence of a polypeptide of the following (A) or (B), said polypeptide having an activity to support proliferation or survival of hematopoietic stem cells or hematopoietic progenitor cells when the hematopoietic stem cells or hematopoietic progenitor cells are cultured in the presence of the polypeptide, (A) a polypeptide which comprises an amino acid sequence selected from the group consisting of SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and SEQ ID NO: 48; or (B) a polypeptide which comprises an amino acid sequence including deletion, substitution or insertion of one or several amino acids in the amino acid sequence as defined in (A), and which has an activity to support proliferation or survival of hematopoietic stem cells or hematopoietic progenitor cells.

(13) A pharmaceutical composition having an effect to support proliferation or survival of hematopoietic stem cells or hematopoietic progenitor cells, which comprises an effective amount of a polypeptide of the following (A) or (B), said polypeptide having an activity to support proliferation or survival of hematopoietic stem cells or hematopoietic progenitor cells when hematopoietic stem cells or hematopoietic progenitor cells are cultured in the presence of the polypeptide, (A) a polypeptide which comprises an amino acid sequence selected from the group consisting of SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and SEQ ID NO: 48; or (B) a polypeptide which comprises an amino acid sequence including deletion, substitution or insertion of one or several amino acids in the amino acid sequence as defined in (A), and which has an activity to support proliferation or survival of hematopoietic stem cells or hematopoietic progenitor cells.

Terms used in this specification are defined as follows.

A hematopoietic stem cell is defined as a cell having totipotency, that is, ability to differentiate into all the cell lineages of the blood cells, and having a potency of self-renew with retaining the totipotency. A hematopoietic progenitor cell is defined as a cell which can differentiate a single cell lineage of the blood cell or plural cell lineages but cannot differentiate into all of the cell lineages. A stromal cell is defined as a cell which can be co-cultured together with the hematopoietic stem cells to construct a hematopoietic environment simulating in vivo hematopoietic environment in vitro. Cells derived from any origin can be used as long as the cells can be co-cultured with the hematopoietic cells in vitro.

Erythrocyte progenitor cells hardly survive and proliferate in in vitro culture environments and rapidly disappear. If the survival and proliferation of the erythrocyte progenitor cells are observed, continuous production of the erythrocyte progenitor cells is predicted to occur due to the survival and proliferation of the more immature hematopoietic stem cells or the hematopoietic progenitor cells. Therefore, in an assessment system of human hematopoietic stem cells, proliferation of hematopoietic stem cells or immature hematopoietic progenitor cells can be determined by using the survival and proliferation of the erythrocyte progenitor cells (BFU-E, CFU-E, and CFU-E mix) as an index.

DETAILED DESCRIPTION OF THE INVENTION

Figure 1:
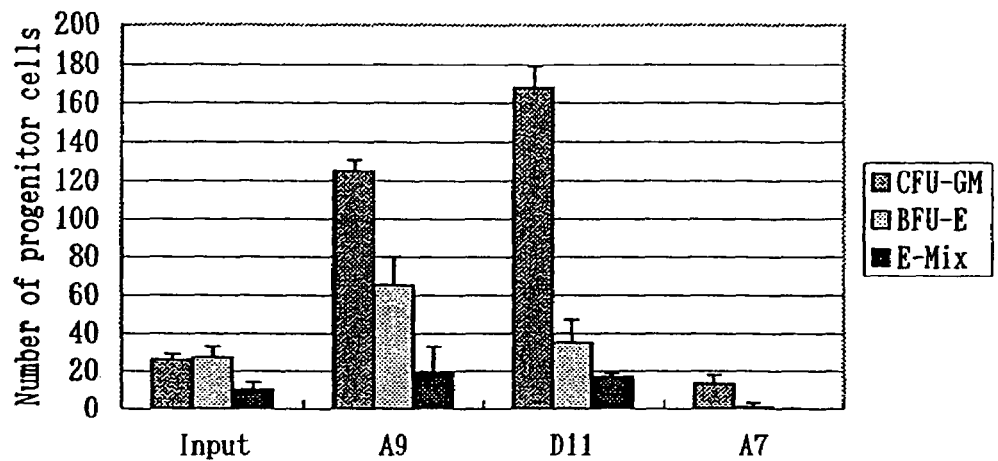
FIG. 1 shows proliferation statuses of hematopoietic stem cells and hematopoietic progenitor cells determined by a clonogenic assay after co-culture of CD34-positive hematopoietic stem cells with AGM-s3 subclone A9, A7, or D11 cells for two weeks.

Hereafter, the present invention will be described in detail below.

The following genes are those identified as genes of which expressions are high in AGM-s3-A9 cell line which has the activity to support hematopoietic stem cells, and low or undetected in AGM-s3-A7 cell line which does not have the activity to support hematopoietic stem cells, and determined to have the activities to support hematopoietic stem cells, of cells in which these gene groups are highly expressed.

Gene SCR-2

The gene is the same gene as a mouse gene, *Mus musculus* glypican-1 (GPC-1) of a GenBank accession number AF185613.

The nucleotide sequence of the gene from mouse and the amino acid sequence deduced from the nucleotide sequence are shown in SEQ ID NO: 8. Only the amino acid sequence is shown in SEQ ID NO: 9.

The human amino acid sequence of GPC-1 is recorded in GenBank under an accession number P35052, and the human nucleotide sequence of GPC-1 is recorded in GenBank database under an accession number AX020122. It is predicted that the similar activity is detected in the human gene.

The nucleotide sequence of the gene from human and the amino acid sequence deduced from the nucleotide sequence are shown in SEQ ID NO: 10. Only the amino acid sequence is shown in SEQ ID NO: 11.

Glypican is a major hepran sulfate proteoglycan existing on a cell surface, and have a characteristic structure such as cysteine rich globular domain, short glycosaminoglycan binding domain, glycosylphosphatidyl-inositol membrane binding domain. Six family genes from glypican-1 to glypican-6 have been found (J Biol Chem 1999 Sep. 17; 274 (38): 26968-77, Glypican-6, a new member of the glypican family of cell surface heparan sulfate proteoglycans. Veugelers M, De Cat B, Ceulemans H, Bruystens A M, Coomans C, Durr J, Vermeesch J, Marynen P, David G).

With respect to biological activities of GPC-1, there are a number of reports: To regulate growth stimulating activity of heparin binding growth factors (fibroblast growth factor 2 (FGF2), heparin-binding EGF-like growth factor (HB-EGF)) to promote proliferation of cancer cells showing autocrine proliferation by stimulation by the growth factors (J Clin Invest 1998 Nov. 1; 102(9): 1662-73, The cell-surface heparan sulfate proteoglycan glypican-1 regulates growth factor action in pancreatic carcinoma cells and is overexpressed in human pancreatic cancer., Kleeff J, Ishiwata T, Kumbasar A, Friess H, Buchler M W, Lander A D, Korc M).

To bind HGF (hepatocyte groth factor) to promote reactivity with cytokines, of antigen-specific B cells. To participate in association of a cell with an adhesive molecule to involve in invasion of the cell (J Biol Chem 1998 Aug. 28; 273 (35): 22825-32, Heparan sulfate proteoglycans as adhesive and anti-invasive molecules. Syndecans and glypican have distinct functions., Liu W, Litwack E D, Stanley M J, Langford J K, Lander A D, Sanderson R D). These findings show that GPC-1 involves in activity expression of various cell-stimulating factors. Also, there is a report that expression of the glypican family gene in bone marrow is confirmed (Biochem J 1999 Nov. 1; 343 Pt 3:663-8, Expression of proteoglycan core proteins in human bone marrow stroma., Schofield K P, Gallagher J T, David G). However, in these reports, it is not described about effects of GPC-1 on hematopoietic stem cells or hematopoietic progenitor cells.

Gene SCR-3

The gene is the same gene as mouse genes, *Mus musculus* chemokine MMRP2 mRNA of a GenBank accession number U15209, *Mus musculus* C10-like chemokine mRNA of U19482 and mouse macrophage inflammatory protein-1gamma mRNA of U49513.

The nuclotide sequence of the gene from mouse and the amino acid sequence deduced from the nucleotide sequence are shown in SEQ ID NO: 12. Only the amino acid sequence is shown in SEQ ID NO: 13.

Gene SCR-4

The nuclotide sequence of the gene from mouse and the amino acid sequence deduced from the nucleotide sequence are shown in SEQ ID NO: 14. Only the amino acid sequence is shown in SEQ ID NO: 15.

It has been found that the sequence has a high homology to *Homo sapiens* clone 25077 mRNA of a GenBank accession number AF131820, and that it is considered to be a mouse ortholog. This sequence is described in WO 00/66784.

The nuclotide sequence of the gene from human and the amino acid sequence deduced from the nucleotide sequence are shown in SEQ ID NO: 16. Only the amino acid sequence is shown in SEQ ID NO: 17.

Gene SCR-5

The nuclotide sequence of the gene from mouse and the amino acid sequence deduced from the nucleotide sequence are shown in SEQ ID NO: 18. Only the amino acid sequence is shown in SEQ ID NO: 19.

It has been found that the sequence has a high homology with *Homo sapiens* esophageal cancer related gene 4 portein (ECRG4) mRNA of a GenBank accession number AF325503, and that it is considered to be a mouse ortholog of AF325503.

The nuclotide sequence of the gene from human and the amino acid sequence deduced from the nucleotide sequence are shown in SEQ ID NO: 20. Only the amino acid sequence is shown in SEQ ID NO: 21.

Gene SCR-6

The nuclotide sequence of the gene from mouse and the amino acid sequence deduced from the nucleotide sequence are shown in SEQ ID NO: 22. Only the amino acid sequence is shown in SEQ ID NO: 23.

The nuclotide sequence of the gene from human and the amino acid sequence deduced from the nucleotide sequence are shown in SEQ ID NO: 47. Only the amino acid sequence is shown in SEQ ID NO: 48.

Gene SCR-7

The nuclotide sequence of the gene from mouse and the amino acid sequence deduced from the nucleotide sequence are shown in SEQ ID NO: 24. Only the amino acid sequence is shown in SEQ ID NO: 25.

Gene SCR-8

The gene is the same gene as *Mus musculus* mRNA for ADAM23 of a GenBank accession number AB009673.

The nuclotide sequence of the gene from mouse and the amino acid sequence deduced from the nucleotide sequence are shown in SEQ ID NO: 26. Only the amino acid sequence is shown in SEQ ID NO: 27.

The sequence has a high homology with a sequence described by JP 11155574-A and the sequence described by JP 11155574-A is considered to be a human ortholog.

The nuclotide sequence of the gene from human and the amino acid sequence deduced from the nucleotide sequence are shown in SEQ ID NO: 28. Only the amino acid sequence is shown in SEQ ID NO: 29.

Polypeptides which are products of these genes have an activity to support proliferation or survival of hematopoietic stem cells or hematopoietic progenitor cells. The expression that a polypeptide has an activity to support proliferation or survival of hematopoietic stem cells or hematopoietic progenitor cells means that proliferation or survival of hematopoietic stem cells or hematopoietic progenitor cells is supported in the presence of the polypeptide or in the presence of stroma cells expressing the polypeptide.

Therefore, the present invention provides use of the polypeptides and DNAs encoding the polypeptides and novel polypeptides among the polypeptides and DNAs encoding the novel polypeptides.

A stem cell proliferation-supporting factor which is a polypeptide encoded by the DNA can be produced by introducing the DNA into a suitable host to prepare a transformant cell, and allowing the DNA to be expressed in the transformant cell.

The DNA may encode the above described factors which have amino acid sequences including substitution, deletion or insertion of one or several amino acids, as long as the activity of the stem cell proliferation-supporting factor to be encoded is not lost. DNAs encoding substantially equivalent polypeptides to this stem cell proliferation-supporting factor can be obtained by modifying the nucleotide sequences so as to include substitution, deletion, insertion, addition, or inversion of amino acid residues in a specific region using site-directed mutagenesis.

The DNAs including the above described mutation can be expressed in appropriate cells and the activity to support hematopoietic stem cells, of the expressed products can be examined, so that the DNAs encoding the polypeptide having functions which are substantially equivalent to this stem cell proliferation-supporting factor are obtained. In addition, the DNAs encoding substantially equivalently active protein as this stem cell proliferation-supporting factor can be obtained by isolating DNAs which hybridize with DNAs including, for example, the nucleotide sequence (ORF portion) as described in SEQ ID NO: 8, 10, 12, 14, 16, 18, 20, 22, 24, 26, 28, or 47 from the cells having the DNA, or probes prepared from these DNAs under the stringent condition; and which encode proteins possessing the activity to support hematopoietic stem cells. The length of the probe is usually 30 to 1000 nucleotides. The stringent condition is, for example, one in which DNAs having homology (determinable with homology search in the compare function of DNASIS version 3.7 (Hitachi Software Engineering)) at not less than 70%, preferably at not less than 80%, are hybridized each other and DNAs having less homology than those are not hybridized each other. The above described stringent condition may be 6×SSC, 5× Denhardt, 0.5% SDS, 68° C. (SSC; 3 M NaCl, 0.3 M sodium citrate) (50× Denhardt; 1% BSA, 1% polyvinyl pyrrolidone, 1% Ficoll 400) or 6×SSC, 5× Deanhardt, 0.5% SDS, 50% Formamide, 42° C., or the like.

Microorganisms such as *Escherichia coli* and yeast, culture cells derived from animals or plants, and the like are used for host cells for expressing the DNA. Preferably, culture cells derived from mammals are used as the host cells. In the case that prokaryotic cells are used as the host cells, the expression is preferably performed in a condition in which a signal peptide region is replaced with a leader sequence suitable for the prokaryotic cells such as P-lactamase (bla), alkaline phosphatase (phoA), and outer membrane protein A (ompA) and the like, or in a form in which a methionine residue is added to the N-terminal site of the mature protein.

The introduction of the DNA to the host cell can be carried out by, for example, incorporating the DNA into a vector suitable for the host in an expressible form, and introducing the resultant recombinant vector to the host cell.

Examples of the culture cells derived from mammals include CHO cell, 293 cell, COS7 cell, and the like. Gene expression regulatory sequence such as a promoter to express the DNA may be originated from the gene itself, or may be derived from other genes such as cytomegalovirus promoter and elongation factor 1 promoter and the like.

Examples of a vector for animal culture cells include plasmid vectors, retrovirus vectors, adenovirus vectors (Neering, S. J., *Blood,* 88: 1147, 1996), herpes virus vectors (Dilloo, D., *Blood,* 89: 119, 1997), HIV vectors, and the like.

In order to introduce the recombinant vector into culture cells, the conventional methods which are usually employed for transformation of culture cells such as calcium phosphate transfection, the liposome method, the DEAE dextran method, the electroporation method and the microinjection method are employed.

The polypeptides of the present invention also comprise polypeptides having amino acid sequences in which one or several amino acids are substituted, deleted or inserted in the amino acid sequence represented in SEQ ID NO: 9, 11, 13, 15, 17, 19, 21, 23, 25, 27 or 29, and having activity to support hematopoietic stem cells in addition to the polypeptides having the amino acid sequence represented in SEQ ID NO: 9, 11, 13, 15, 17, 19, 21, 23, 25, 27, 29, or 48. That is, even if mouse and human stem cell proliferation-supporting factors are modified by substitution, deletion, insertion or the like, polypeptides holding essential functions as a stem cell proliferation-supporting factor can be considered to be substantially equivalent to the stem cell proliferation-supporting factor.

These modified stem cell proliferation-supporting factors can be obtained by treating DNA encoding the stem cell proliferation-supporting factor or host cells including the above mentioned DNA with a mutagen, or by mutating the above mentioned DNA so as to substitute, delete, or insert an amino acid at a specific site using site-directed mutagenesis. The residual of the activity to support the hematopoietic stem cells in the obtained mutant polypeptide is confirmed by transferring hematopoietic stem cells cultured in the presence of the mutant polypeptides into irradiated mice, and monitoring peripheral hematological cellularity over time, as in the examples described below.

As for the amino acid deletion, the polypeptide may be a fragment which lacks an amino acid sequence at the N-terminal end and/or the C-terminal end. The fragment lacking the amino acid sequence at the N-terminal end and/or the C-terminal end can be obtained by a usual method, and the hematopoietic stem cell-supporting activity of the fragment can be determined by a similar way to that described with respect to the mutated polypeptide as a signal sequence or a transmembrane region in the amino acid sequence, a fragment having the hematopoietic stem cell-supporting activity is predicted by using it as an index. For example, a protein encoded by human SCR-8 is a transmembrane protein of type I passing through the membrane once, and it is therefore predicted that even if it made to be a soluble protein lacking the transmembrane region, it has the activity to support to proliferation or survival of hematopoietic stem cells or hematopoietic progenitor cells. The transmembrane region can be predicted with a known program based on the amino acid sequence. For example, if it is predicted with a program called PSORT II (available through the Internet at the http site, psort.nibb.ac.jp/index.html), the transmembrane region is amino acids at positions 790 to 806 in SEQ ID NO: 29, and it is predicted that even if a fragment up to position 789, the fragment has activity to support proliferation or survival of hematopoietic stem cells or hematopoietic progenitor cells.

Since the nucleotide sequences of the above described DNAs have been clarified by the present invention, the DNAs can be also obtained by isolating the corresponding DNAs from mouse or human cDNA or chromosome DNA libraries using PCR in which the oligonucleotides prepared based on these nucleotide sequences are used as primers or using hybridization in which the oligonucleotides prepared based on these nucleotide sequences are used as probes.

In order to complete the present invention, the DNAs of the present invention have been isolated from cDNA library of AGM-s3-A9 cells which are a mouse stromal cell line having the activity to support the hematopoietic stem cells, using SBH (Sequencing By Hybridization) method (Drmanac, S., *Nat. Biotechnol.,* 16. 54, 1998; Drmanac, R., *Methods. Enzymol.,* 303, 165, 1999) as described below. The mouse stromal cell lines having the activity to support the hematopoietic stem cells can be obtained using the method disclosed in WO99/03980 or from Cell Bank of Institute of Physical and Chemical Research (RIKEN) or ATCC.

An outline of SBH method will be described below. Probes having eight or nine nucleotides whose sequences are different from each other are prepared. When the nucleotide sequences corresponding to those of the probe exist in a targeted gene, the probes can hybridize with the gene. The hybridization can be easily detected with utilization of radio isotope- or fluorescence-labeled probes. Each clone in the library is picked up, and blotted on a membrane. Then, the repeated hybridizations are performed with the each of above described probes, so that one can identify the combination of probes that hybridize to each clone. Since the combination of hybridized probes depends on genes, the combination of probes which hybridize to an identical gene is the same. That is, the same gene can be identified as one group (cluster) according to the the combination of the hybridized probes. The number of clones of each gene in the cDNA library can be determined by classifying each clone in the library based on patterns of the hybridized probes and counting the classified clones. Thus, frequency of expression of each gene in the library can be determined.

cDNA libraries are prepared from cells having an activity to support the hematopoietic stem cells and from cells not having the activity. Clustering is performed for the cDNA libraries. Statuses of expressed genes among cells are compared, so that the genes highly expressed with specificity to the supporting cells are selected. The expression statuses of these genes in each of above described cells are further examined by Northern blot analysis, so that genes which are highly expressed in the cells having the activity to support the hematopoietic stem cells are obtained.

The above mentioned genes are the genes which are highly expressed with specificity to the supporting cells and which are obtained through the above described process. Full-length genes have been cloned from the cDNA library derived from AGM-s3-A9 cell.

Further, in order to determine an ability of gene products to support hematopoiesis, a gene fragment including gene ORF was transferred into stromal cells using a retrovirus vector, and the change in the activity to support the hematopoietic stem cells of the stromal cells was determined. Specifically, after the stromal cells into which the gene was not introduced or into which a control vector was introduced and those into which the gene was introduced were each co-cultured with the mouse hematopoietic stem cells, the hematopoietic cells were transplanted into irradiated mice. The engraftment of the co-cultured hematopoietic cells in recipient mice were examined. As a result, the mice into which the hematopoietic stem cells co-cultured with the gene-introduced cells were transplanted, showed increased chimerism after the transplantation compared with co-culture with the cells into which the gene was not introduced. This result shows that in the gene-expressed stromal cells, an activity to support the proliferation or survival of the hematopoietic stem cells or the hematopoietic progenitor cells is increased or imparted. As a result, it has become evident that expression of the above described genes has a function to increase the above described activity in the stromal cells or impart the activity to the stromal cells. Therefore, it is revealed that products of the genes affect hematopoietic stem cells or hematopoietic progenitor cells to show an activity to support the survival or the proliferation thereof, or affect stromal cells to show an activity to increase an activity to support the hematopoietic stem cells therein or impart the activity thereto.

The polypeptides of the present invention can be used as a medicine to proliferate or support human hematopoietic stem cells or human hematopoietic progenitor cells when they affect hematopoietic stem cells or hematopoietic progenitor cells to show an activity to support survival or proliferation thereof, in other words, the polypeptides have an activity to support survival or proliferation of hematopoietic stem cells or hematopoietic progenitor cells if the hematopoietic stem cells or the hematopoietic progenitor cells are cultured in the presence of the polypeptides. The pharmaceutical composition can be used for supporting proliferation or survival of human hematopoietic stem cells or human hematopoietic progenitor cells in vitro. For hematopoietic stem cell transplantation therapies such as peripheral blood stem cell transplantation and cord blood stem cell transplantation, a sufficient amount of the hematopoietic stem cells sometimes cannot be collected and the transplantation may not be performed. Even if the enough amount of the stem cells can not be collected, the enough amount of the hematopoietic stem cells can be obtained and transplanted by amplification of the hematopoietic stem cells in vitro using this polypeptides. That is, the hematopoietic stem cells can be amplified without differentiation by culturing the hematopoietic stem cells in culture medium including these polypeptides. It may be considered the hematopoietic stem cells are able to be amplified more efficiently with addition of a variety of cytokines to the medium.

When the hematopoietic stem cells or the hematopoietic progenitor cells are cultured in the medium including the polypeptides of the present invention, the hematopoietic stem cells or the hematopoietic progenitor cells used may be isolated one of these cell types alone or may be both of the cell types. In addition, the cells may include at least the hematopoietic stem cells or the hematopoietic progenitor cells, and include other hematopoietic cells. Further, it can be used a fraction containing hematopoietic stem cells or progenitor cells fractionated from the cell population that contain the hematopoietic stem cells or progenitor cells.

Examples of sources of the hematopoietic stem cells and the hematopoietic progenitor cells in the method of the present invention include a fetal liver, bone marrow, fetal bone marrow, peripheral blood, the peripheral blood from persons whose stem cells are mobilized by administration of cytokines and/or antitumor drugs, cord blood, and the like of mammals such as human and mouse and the like. Any sources may be used as long as the tissue includes the hematopoietic stem cells.

A culture method using petri dishes and flasks for culture may be employed to culture the hematopoietic stem cells or the hematopoietic progenitor cells. The cultivation of the hematopoietic stem cells and/or progenitor cells may be improved by mechanically controlling medium composition, pH, and the like, and using a bioreactor capable of high density cultivation (Schwartz, Proc. Natl. Acad. Sci. U.S.A., 88: 6760, 1991; Koller, M. R., Bio/Technology, 11: 358, 1993; Koller, M. R., Blood, 82: 378, 1993; Palsson, B. O., Bio/Technology, 11: 368, 1993).

The stromal cells in which DNAs encoding the polypeptide of the present invention can be obtained as described with respect to the expression of the DNAs.

The co-culture of the stromal cells and the hematopoietic cells can be performed simply after the collection of the bone marrow cells without further separation. Furthermore, co-culture can be performed by separating components such as stromal cells, hematopoietic cells and other cell populations from collected bone marrow and combining them with the hematopoietic cells and stromal cells which are not from the individual from which the bone marrow is cllected. Furthermore, after stromal cells are cultured to grow to the stromal cells, hematopoietic cells can be added to perform co-culture with the hematopoietic stem cells. At this time, cell stimulating factors can added to the culture system of stromal cells to more effectively support proliferation and survival. Concrete examples of the cell stimulating factor include a growth factor which is typically a cytokine such as SCF (stem cell factor), IL-3 (interleukin 3), GM-CSF (granulocyte/macrophage colony-stimulating factor), IL-6 (interleukin 6), TPO (thrombopoietin), G-CSF (granulocyte colony-stimulating factor), TGF-b (transforming growth factor-b), MIP-la (Davatelis, G., J. Exp. Med. 167: 1939, 1988); a differentiation and proliferation control factor such as hematopoietic hormones such as EPO (erythropoietin), chemokine, Wnt gene product, and notch ligand; and a development control factor.

In addition, when the polypeptide of the present invention affects hematopoietic stem cells or hematopoietic progenitor cells to show an activity to support survival or proliferation thereof, in other words, the polypeptide has an activity to support survival or proliferation of hematopoietic stem cells or hematopoietic progenitor cells if the hematopoietic stem cells or the hematopoietic progenitor cells are cultured in the presence of the polypeptide, the proliferation and the survival of the hematopoietic stem cells or the hematopoietic progenitor cells can be retained by allowing the recombinant polypeptide of the present invention alone or in combination with the cell stimulating factors to affect hematopoietic stem cells or hematopoietic progenitor cells, without stromal cells. Examples of the cell stimulating factors used in this case are above described cell stimulating factors and the like.

Medium used for the culture is not specially restricted as long as the proliferation or the survival of the hematopoietic stem cells or the hematopoietic progenitor cells is not harmed. Preferable media are, for example, MEM-α medium (GIBCO BRL), SF-02 medium (Sanko Junyaku), Opti-MEM medium (GIBCO BRL), IMDM medium (GIBCO BRL), and PRMI1640 medium (GIBCO BRL). A culture temperature is usually ranging from 25 to 39° C., and preferably ranging from 33 to 39° C. Examples of additives to the medium are fetal bovine serum, human serum, horse serum, insulin, transferrin, lactoferrin, ethanolamine, sodium selenite, monothiolglycerol, 2-mercaptoethanol, bovine serum albumin, sodium pyruvate, polyethylene glycol, a variety of vitamins, and a variety of amino acids. A concentration of $CO_2$ is usually ranging from four to six percent, and preferably five percent.

Since the hematopoietic stem cells can differentiate into all the hematopoietic cell lineages, the hematopoietic stem cells can be amplified and differentiated into a specific cell type in vitro, and then the specific cells can be transplanted. For example, when erythrocytes are necessary, after the cultivation of the patient's stem cells to amplify them, the hematopoietic cells whose main component is the erythrocyte can be artificially produced using an erythrocyte differentiation induction-promoting factor such as EPO.

The hematopoietic stem cells or the hematopoietic progenitor cells cultured using the polypeptides of the present invention can be used as a graft for blood cell transplantation replacing the conventional bone marrow transplantation or cord blood transplantation. Transplantation of the hematopoietic stem cells is superior to the conventional blood cell transplantation therapy, since the engraftment can last semipermanently.

The transplantation of the hematopoietic stem cells can be employed as therapy for a variety of diseases in addition to combination therapy with total body X-ray irradiation therapy or advanced chemotherapy for leukemia. For example, when therapy accompanied with myelosuppression as an adverse reaction, such as chemotherapy, radiation therapy, and the like is performed for the patient with solid cancer, the patient can get benefit of early recovery and stronger chemotherapy than the conventional one can be performed to improve the therapeutic effect of the chemotherapy by collecting the bone marrow before the therapy, allowing the hematopoietic stem cells or the hematopoietic progenitor cells to be amplified in vitro and returning the amplified cells to the patient after the therapy. In addition, by allowing the hematopoietic stem cells or the hematopoietic progenitor cells obtained according to the present invention to be differentiated into a variety of hematopoietic cells and transplanting these cells into a patient with hypoplasia of a given hematopoietic cells, the patient's deficient status can be improved. In addition, this therapy can improve dyshemopoietic anemia to develop anemia such as aplastic anemia caused by bone marrow hypoplasia. Furthermore, examples of diseases in which the transplantation of the hematopoietic stem cells according to the present invention is effective include immunodeficiency syndrome such as chronic granulomatous disease, duplicated immunodeficiency syndrome, agammaglobulinemia, Wiskott-Aldrich syndrome, acquired immunodeficiency syndrome (AIDS), and the like, thalassemia, hemolytic anemia due to an enzyme defect, congenital anemia such as sicklemia, Gaucher's disease, lysosomal storage disease such as mucopolysaccharidosis, adrenoleukodegeneracy, a variety of cancers and tumors, and the like.

Transplantation of the hematopoietic stem cells may be performed in the same manner as the conventional bone marrow transplantation or cord blood transplantation other than the differences of the cells used.

The source of the hematopoietic stem cells which may be used for the above described hematopoietic stem cell transplantation is not restricted to the bone marrow, and the above described fetal liver, the fetal bone marrow, the peripheral blood, the peripheral blood with stem cells mobilized by administration of cytokines and/or antitumor drugs, the cord blood, and the like may be used.

The graft may be a composition including buffer solution and the like in addition to the hematopoietic stem cells and the hematopoietic progenitor cells produced by the method according to the present invention.

The hematopoietic stem cells or the hematopoietic progenitor cells produced according to the present invention may be used for ex vivo gene therapy. Because of the low frequency of recombination of target genes to the chromosome because the stem cells are in the resting state, differentiation of the stem cells during the culture period, and the like, the gene therapy to the hematopoietic stem cells has been hard to be established. However, the present invention can amplify the stem cells without differentiation, so that efficacy of gene transfer is expected to be remarkably improved. In this gene therapy, a foreign gene (a gene for therapy) is transferred into the hematopoietic stem cells or the hematopoietic progenitor cells, and then the obtained gene-transferred cells are used. The foreign gene to be transferred is appropriately selected according to disease. Examples of diseases in which the target cells of the gene therapy are the hematopoietic cells include immunodeficiency syndrome such as chronic granulomatous disease, duplicated immunodeficiency syndrome, agammaglobulinemia, Wiskott-Aldrich syndrome, acquired immunodeficiency syndrome (AIDS), and the like, thalassemia, hemolytic anemia due to an enzyme defect, congenital anemia such as sicklemia, Gaucher's disease, lysosomal storage disease such as mucopolysaccharidosis, adrenoleukodegeneracy, a variety of cancers and tumors, and the like.

A usual method used for transfer of a gene into animal cells is employed for the transfer of the gene for the therapy into the hematopoietic stem cells or the hematopoietic progenitor cells. Examples include a method using a vector for animal cells derived from virus utilized for a gene therapy such as retrovirus vectors such as Moloney mouse leukemia virus, adenovirus vectors, adeno-associated virus (AAV) vectors, herpes simplex virus vectors, and HIV vectors (with respect to a vector for gene therapy, see Verma, I. M., Nature, 389: 239, 1997); calcium phosphate transfection, DEAE-dextran transfection, electroporation, the liposome method, the lipofection method, the microinjection method, and the like. Among them, the method using the retrovirus vector, the adeno-associated virus vector, or the HIV vector is preferable, since permanent expression of a gene is expected due to insertion into the chromosome DNA of a target cell.

For example, the adeno-associated virus (AAV) vector can be prepared as follows. First, a vector plasmid in which a gene for therapy is inserted into ITR (inverted terminal repeat) at both ends of wild-type adeno-associated virus DNA and a helper plasmid for supplementing virus proteins are transfected into 293 cell line. Next, adenovirus as helper virus is infected, so that virus particles including the AAV vector are produced. Alternatively, instead of adenovirus, a plasmid which expresses adenovirus gene having helper function may be transfected. The hematopoietic stem cells or the hematopoietic progenitor cells are infected with the obtained virus particles. Preferably, appropriate promoter, enhancer, insulator and the like are inserted into the upstream region of the target gene in the vector DNA, so that the expression of the gene is regulated. When a marker gene such as a drug resistant gene is used in addition to the gene for therapy, cells into which the gene for therapy are transferred are easily selected. The gene for therapy may be a sense gene or an antisense gene.

A composition for gene therapy may include a buffer solution and a novel active ingredient and the like in addition to the hematopoietic stem cells or the hematopoietic progenitor cells by the method according to the present invention.

A vector for gene therapy can be produced by incorporating the DNA of the present invention in an expression vector using a usual method. This vector for gene therapy is useful to treat diseases which need survival and proliferation of the human hematopoietic stem cells. That is, the vector for gene therapy is transferred into the hematopoietic stem cells and the cells are cultured in vitro, so that the hematopoietic stem cells or the hematopoietic progenitor cells can proliferate dominatingly. The proliferation of hematopoietic stem cells in vivo can be caused by returning these hematopoietic stem cells thus treated. The proliferation of hematopoietic stem cells in vivo can significantly promoted by introducing this vector for gene therapy into the body. Alternatively, the bone marrow cells derived from a patient are cultured as it is and this vector for gene therapy is transferred thereto, so that the hematopoietic stem cells or the hematopoietic progenitor cells can be proliferated in a culture system. Alternatively, this vector for gene therapy is transferred into the stromal cells and mesenchaymal stem cells obtained by isolating and culturing stromal cells from the bone marrow, so that the activity to support the hematopoietic stem cells can be added or increased.

As shown in Examples, since it is possible that by introducing the DNA of the present invention into the stromal cells without the activity to support the hematopoietic stem cells, this activity can be imparted, stromal cells having the activity to support the hematopoietic stem cells can be prepared by gene transfer to stromal cells derived from human or mouse. The stromal cells expressing the DNA of the present invention and the hematopoietic stem cells or the hematopoietic progenitor cells are co-cultured, so that the hematopoietic stem cells or the hematopoietic progenitor cells can survive and proliferate so as to be useful for a variety treatment.

Since the hematopoietic stem cells or the hematopoietic progenitor cells can survive and proliferate by expression of the DNA of the present invention in the stromal cell, an activity to support the hematopoietic stem cells of the stromal cells can be determined using the expression of the DNA of the present invention as an index. The expression of the DNA of the present invention in the stromal cells can be confirmed using an antibody against a polypeptide encoded by the DNA of the present invention. Also, PCR primers can be prepared based on nucleotide sequences, and RNA is prepared from the stromal cells of interest, and RT-PCR is performed, so that the expression of the DNA of the present invention can be confirmed. The antibody will be described below.

The pharmaceutical composition of the present invention can be administered to human. The pharmaceutical composition having an activity to proliferate or to support the human hematopoietic stem cells or the hematopoietic progenitor cells can be produced by mixing medically acceptable diluent, stabilizer, carrier, and/or other additives with the polypeptides of the present invention. At this time, in order to increase the stability of the protein in vivo, the polypeptides of the present invention may be modified by a modifying agent. Examples of the modifying agent include polyethylene glycol (PEG), dextran, poly(N-vinyl-pyrrolidone), polypropylene glycol homopolymer, polypropylene oxide/ethylene oxide copolymer, polyoxyethylated polyol, polyvinyl alcohol, and the like. The modification of the protein with PEG can be performed by, for example, a method in which activated ester derivatives of PEG is reacted with the protein, a method in which aldehyde derivatives at the terminal portion of PEG is reacted with the protein in the presence of a reducing agent, and the like. Japanese Patent Application Laid-Open No. 10-510980 discloses such protein modification in detail.

When the pharmaceutical composition of the present invention is administered to human, recovery from hematological suppression due to an adverse drug reaction of carcinostatics; early recovery of hematopoietic cells at bone marrow transplantation, peripheral blood stem cell transplantation, or cord blood transplantation; and recovery of hematopoietic function at pancytopenia such as aplastic anemia (AA) and myelodysplastic syndrome (MDS) are expected.

The antibodies of the present invention react specifically to the above described polypeptides of the present invention. The antibodies of the present invention may be monoclonal antibodies or polyclonal antibodies as long as they react specifically to the above described polypeptides.

The antibodies of the present invention can be prepared according to usual methods. For example, the antibodies can be prepared either in vivo method in which animals are additionally immunized by an antigen together with adjuvant once or several times at an interval of several weeks or in vitro method in which immune cells are isolated and sensitized in an appropriate culture system. Examples of immune cells which can produce the antibodies of the present invention include splenic cells, tonsillar cells, lymph gland cells, and the like.

The whole polypeptide according to the present invention is not necessarily used as an antigen. A part of this polypeptide may be used as an antigen. When the antigen is a short peptide, particularly, a peptide made of about 20 amino acid residues, it may be used by binding it to a carrier protein having high antigenicity such as keyhole lympet hemocyanin or bovine serum albumin using chemical modification and the like. Alternatively, the antigen may be used by covalently binding it to peptide having branching skeleton such as lysine core MAP peptide instead of the carrier protein (Posnett et al., *J. Biol. Chem.*, 263, 1719-1725, 1988; Lu et al., *Mol. Immunol.*, 28, 623-630, 1991; Briand et al., *J. Immunol. Methods*, 156, 255-265, 1992).

Examples of adjuvant include Freund's complete adjuvant, Freund's incomplete adjuvant, aluminum hydroxide gel, and the like. Antigen-given animals are, for example, mouse, rat, rabbit, sheep, goat, chicken, bovine, horse, guinea pig, hamster, and the like. The blood is collected from these animals and the serum is separated. Then, immunoglobulin is purified from the serum using an ammonium sulfate precipitation method, anion exchange chromatography, protein A chromatography, or protein G chromatography to obtain polyclonal antibodies.

With respect to chicken, antibodies can be purified from an egg. Monoclonal antibodies can be prepared by purification from supernatant of culture of hybridoma cells which are made by fusion of the immune cells sensitized in vitro, or immune cells from the above described animals with parent cells capable of cultivation, or ascites from animals which received intraperitoneal administration of hybridoma cells. Examples of parent cells include X63, NS-1, P3U1, X63.653, SP2/0, Y3, SK0-007, GM1500, UC729-6, HM2.0, NP4-1 cell lines, and the like. Preparation may be performed by cultivating the immortalized antibody-forming cells obtained by sensitization in vitro, or infection of a proper virus such as EB virus to the immune cells of the above described animals.

In addition to these cell engineering methods, the antibodies can be obtained using gene engineering methods. For example, the antibody gene obtained from the in vitro sensitized cells or immune cells derived from the above described animals is amplified by PCR (polymerase chain reaction) and isolated, and the amplified genes are transferred into microorganisms such as *E. coli* to produce the antibodies. Alternatively, the antibodies may be expressed on surfaces of phages as fused proteins.

By measuring polypeptides in vivo using the antibodies of the present invention, the relationship between the polypeptides and pathological status of a variety of diseases can be clarified. Moreover, the antibodies can be used for diagnosis and treatment of diseases, and efficient affinity purification of the polypeptides.

The present invention provides polypeptides having an activity to support survival or proliferation of hematopoietic stem cells or hematopoietic progenitor cells by effecting thereon, or an activity to impart an activity to support the hematopoietic stem cells to stromal cells by effecting thereon, and also provides DNAs encoding thereof. The polypeptides of the present invention can efficiently maintain the proliferation or the survival of the hematopoietic stem cells or the hematopoietic progenitor cells.

BEST MODE FOR CARRYING OUT THE INVENTION

Hereafter, the present invention will be described in detail by reference to examples.

EXAMPLE 1

Preparation of Fragment of Gene which is Specifically Expressed in Hematopoietic Stem Cell-Supporting Cells (I) Preparation of Stromal Cell Line Derived from Mouse AGM (1) Isolation of AGM Region from Fetal Mouse C3H/HeNSLc mice of both genders (purchased from Japan SLC INC.) were kept under a SPF (specific pathogen-free) environment. One or two female mice and one male mouse were placed in the same cage over a night. In the next morning, the female mice in which the existence of a vaginal plug was observed were transferred to other cages and kept. The day when the existence of the vaginal plug was observed was defined to be the 0.5th day of pregnancy. On the 10.5th day of the pregnancy, after mouse was sacrificed by cervical dislocation, fetuses were extirpated. Isolation of AGM regions was performed according to the method by Godin et al. (Godin, I., Proc. Natl. Acad. Sci. U.S.A., 92: 773-777, 1995) and the method by Medvinsky et al. (Medvinsky, A. L., Blood, 87: 557-565, 1996). The fetuses were placed in a culture dishes to which PBS(-) (phosphate buffered saline) (produced by Nissui Seiyaku) was added in a volume just sufficient to cover the fetuses. After the AGM regions were carefully excised so as not to include other regions under a stereoscopic microscope, they were put in another 24-well culture dish (Nunc).

(2) Establishment of Cell Lines Derived from AGM

One drop of MEM medium (Sigma) containing 10% FCS (Hyclone) was added to the AGM regions in the 24-well culture dish (Nunc), and AGM regions were cultured in an incubator overnight. The culture was performed in the MEM medium (Sigma) containing 10% FCS (Hyclone) at 37° C., in an atmosphere of 5% $CO_2$, and at a humidity of 100%. When the cells of the AGM regions adhered to the culture dish due to overnight cultivation, two milliliters of MEM medium containing 10% FCS was further added. Stromal cells began to appear around the AGM region tissue fragment after the continuous cultivation. After one-week cultivation, adhesive cells were separated by trypsin treatment (0.05% trypsin in PBS containing 0.53 mM EDTA (Gibco BRL) at 37° C. for three to five minutes). The stromal cells were then washed twice with the medium, and seeded on 6-well culture dish (Nunc). On the next day, the cells which did not adhere to the culture dish and the medium were removed, and then, fresh medium was added. Two weeks after transfer to the 6-well culture dish, cells were γ-ray-irradiated at 900 Rad to eliminate endogenous hematopoietic cells. An attempt of the direct cell cloning by limiting dilution from this culture system was made, but no cell proliferation was observed and the cloning ended in failure. Then, after the number of seeded cells in one well was increased and cells were adapted so as to be able to proliferate from a small number of cells, the cells were cloned by limiting dilution.

Specifically, the AGM was extirpated and cultured in the same manner as described above. The culture system two weeks after the γ-ray radiation was trypsinized (0.05% trypsin in PBS containing 0.53 mM EDTA at 37° C. for three to five minutes) to suspend the cells, and the cells were seeded in a 24-well culture dish at 50 to 100 cells/well. After the culture was continued for three weeks, the cells were seeded in a 96-well culture dish (Nunc) by means of limiting dilution, at 0.3 cells/well. The cells which were grown from the well in which only one cell was seeded were allowed to enlarge culture. As a result, the cells were successfully cloned to obtain fibroblast-like cells and cobble stone-like cells.

A CD34-positive cell fraction derived from the human cord blood was co-cultured with the fibroblast-like cells for two weeks to examine the presence of colony-forming cells during the culture. Colony-forming cells could not be found in the co-culture system with the fibroblast-like cells. Then, the similar examination was performed for seven cell clones showing the cobble-stone-like form. Three clones having an activity to support proliferation of human hematopoietic stem cells were obtained and were named AGM-s1, AGM-s2, and AGM-s3.

(II) Preparation of Hematopoietic Stem Cells from Mouse Bone Marrow

Bone marrow was collected from a femur of C57BL/6-Ly5.1 pep (eight- to ten-week age, and male) (the gift from Professor K. Nakauchi, University of Tsukuba), and suspended in PBS. After the mouse bone marrow mononuclear cells were concentrated by specific gravity centrifugation according to the usual method (S. Kouzu, Fundamental techniques for immunology, YODOSHA, 1995), the cells were suspended in staining buffer (PBS containing 5% FCS and 0.05% $NaN_3$), and a hematopoietic stem cell fraction was obtained as follows (Osawa, M. et al., Science 273: 242-245, 1996).

An FITC-conjugated anti-CD34 antibody, a phycoerythrin-conjugated anti-Sca-1 antibody, an allophycocyanin anti-c-Kit antibody (all purchased from Pharmingen) and six biotylated anti-differentiation antigen antibodies (CD45R, CD4, CD8, Gr-1, Terll9, and CD11c, all purchased from Pharmingen) as molecular markers (Lin), were added to a suspension of the bone marrow mononuclear cells and incubated for 20 min on ice to cause reaction. After the cells were washed twice with staining buffer, CD34-negative, Sca-1-positive, c-Kit-positive, and Lin-negative cells were isolated on a cell sorter (FACS Vantage, Becton Dickinson).

(III) Subcloning of Mouse Stromal Cell Line and Determination of Activity to Support Hematopoietic Stem Cells of a Variety of Cell Lines (1) Subcloning of Mouse Stromal Cell Line 1) Isolation of AGM-s3 Subclone Stromal cell line AGM-s3 derived from AGM, which was subcultured in MEMA medium (GIBCO BRL) including inactivated 10% FCS (bovine fetal serum, Hyclone), was suspended in PBS containing 5% FCS (PBS-FCS). Clone sorting was performed in a 96-well culture dish (Falcon) at one cell/well using a cell sorter (FACS Vantage; Becton Dickinson). Among cells in the 96 wells, cultures of the cells which grew were expanded, so that thirteen kinds of AGM-s3 subclones were obtained. The activity to support the hematopoietic cells of these AGM-s3 subclones were examined.

2) Isolation of Human Cord Blood CD34-Positive Stem Cell

The human cord blood was collected at normal delivery according to the criteria approved by Ethics committee of Kirin Beer Iyaku Tansaku Kenkyusho. The cord blood was collected using a heparin-added syringe so as not to coagulate. The heparin treated cord blood was overlaid on Lymphoprep (NYCOMED PHARMA), and mononuclear cells were separated by specific gravity centrifugation (at 400G, at room temperature, and for 30 minutes). Erythrocytes contaminated in the mononuclear cell fraction were lyzed by treatment with an ammonium chloride buffer solution (0.83% $NH_4Cl$-Tris HCl, 20 mM, pH 6.8) at room temperature for two minutes. After the mononuclear cells were washed with PBS-FCS, ten milligrams of human IgG was added thereto and the mixture was allowed to stand on ice for ten minutes. Then, the cells were further washed with PBS-FCS. Biotinylated antibodies against the antigens specific to the human differentiated blood cells, that is, the antibodies against CD2, CD11c (purified from ATCC hybridoma), CD19 (Pharmingen), CD15, and CD41 (Leinco Technologies Inc.), and Glycophorin A (Cosmo Bio) were added thereto, and the mixture was allowed to stand on ice for 20 min. After washing with PBS-FCS, the cells were suspended in one milliliter of PBS containing 5% FCS, 10 mM EDTA, and 0.05% $NaN_3$ (PBS-FCS-EDTA-$NaN_3$). Streptavidin-bound magnetic beads (BioMag. Per Septive Diagnostics) were added thereto, and the mixture was allowed to stand on ice for 40 min. The differentiated blood cells which expressed differentiation antigens were removed using a magnetic separator (Dynal MPC-1 Dynal). An FITC-labeled anti-CD34 antibody (Immunotech S. A., Marseilles, France) was added to the remaining differentiated blood cell antigen-negative cell fraction. After incubation on ice for 20 min., a CD34-positive fraction was recovered using a cell sorter. This cell population was defined as a hematopoietic stem cell population derived from the human cord blood.

3) Co-culture of the Human Hematopoietic Stem Cells and AGM-s3 Subclone

After 13 kinds of AGM-s3 subclones and stromal cell line MS-5 derived from the mouse bone marrow were each seeded in a 24-well culture dish (Falcon) at $1\times10^4$ cells/well, and cells were cultured in one milliliter of MEMα medium containing 10% FCS and allowed to grow until the cells covered all over the bottom surfaces of the wells. CD34-positive hematopoietic stem cells derived from the human cord blood were placed on the above described stromal cells at 500 cells/well, and co-cultured in one milliliter of MEMα medium containing 10% FCS. One week after the start of the co-culture, one milliliter of the same medium was further added. Two weeks after the start of the co-culture, the stromal cells and the human blood cells were trypsinized (0.05% trypsin in PBS containing 0.5 mM EDTA (GIBCO BRL) at 37° C.; standing for two to five min.) to simultaneously separate them from the culture dish. An activity to support the hematopoietic stem cells was determined with a clonogenic assay.

4) Assessment of Proliferation Statuses of the Hematopoietic Stem Cells and Hematopoietic Progenitor Cells by Clonogenic Assay The cells which proliferated in the above described co-culture system were appropriately diluted, and subjected to one milliliter of methylcellulose culture system to be analyzed. The analysis using the methylcellulose culture system was performed using a 6-well culture dish (Falcon) in MethoCult H4230 (Stem Cell Technologies Inc.) to which 10 ng/ml of human SCF, human IL-3, human IL-6, human G-CSF, and human TPO, and 2 IU/ml of EPO were added. All of a variety of the above described hematopoietic factors were recombinants and pure. After two-week culture, developed colonies were observed under a microscope to count numbers of CFU-GM (granulocyte-macrophage colony-forming unit), BFU-E (erythroid burst forming unit), and CFU-E mix (erythrocyte mixed colony-forming unit).

FIG. 1 shows the result of two-week co-culture of the CD34-positive hematopoietic stem cells and the AGM-s3 subclone A9, A7, or D11. As a result of the co-culture, A9 and D11 subclones among 13 kinds of AGM-s3 subclones supported proliferation of all three series of CFU-GM, BFU-E, and CFU-E mix. Especially, although BFU-E and CFU-E mix, that is, the progenitor cells of erythrocytes were hardly to be supported in usual, their proliferations were observed in the co-culture system with A9 or D11 cells. The results showed that proliferation or maintenance of the hematopoietic stem cells or the hematopoietic progenitor cells occurred in the co-culture with A9 or D11 cells and the progenitor cells of the erythrocyte were continuously supplied. In contrast, although cellular morphology of A7 was similar to that of A9, A7 did not support CFU-GM, BFU-E, and CFU-E mix.

Figure 2:
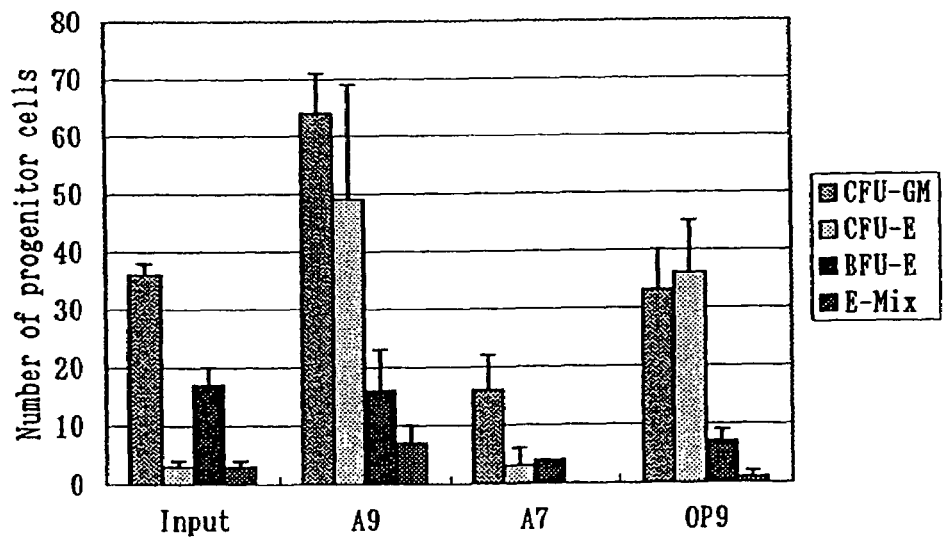
FIG. 2 shows proliferation statuses of hematopoietic stem cells and hematopoietic progenitor cells determined by a clonogenic assay after co-culture of CD34-positive hematopoietic stem cells with AGM-s3 subclone A9, A7, or OP9 cells for two weeks.

5) Comparison of an Activity to Support the Human Hematopoietic Stem Cells Between A9 and a Stromal Cell Line OP9 Derived from Mouse Fetus Comparison of an activity to support the CD34-positive hematopoietic stem cells derived from the human cord blood between AGM-s3 subclones A9 and A7, and a stromal cell line OP9 derived from mouse fetus (RCB1124, the Cell Development Bank of RIKEN) were performed with CFU-GM, BFU-E, CFU-E and CFU-E mix as indexes, using the above described determination system. FIG. 2 shows the result of the two-week co-culture. In the A7 cell culture system, CFU-GM, BFU-E, and CFU-E were significantly decreased and CFU-E mix was completely disappeared. In contrast, with OP9 cells, a variety of blood cell progenitor cells including CFU-E mix were supported, although the supporting ability was less than that of A9 cells. Therefore, it has been found that OP9 cells possess the activity to support the hematopoietic stem cells.

(2) Assessment of Activity to Support the Hematopoietic Stem Cells in a Variety of Cell Lines The above described stromal cell lines (AGM-s3-A9, AGM-s3-A7, and AGM-s3-G1), 3T3Swiss (ATCC), OP9, and NIH3T3 (ATCC) were seeded in a 24-well culture dish (Falcon) at $5\times10^4$ cells/well. The cell lines were cultured in MEMa medium (GIBCO BRL) containing inactivated 10% FCS (bovine fetal serum, Hyclone) for one day and allowed to proliferate until the cells covered all over the bottom surfaces of the wells. Then, the medium was replaced to one milliliter of fresh medium, thirty cells of the mouse hematopoietic stem cells (derived from C57BL/6-Ly5.1) obtained in the above (II) were placed on this cell layer, and co-culture was started.

On seventh day of the cultivation, the cells were trypsinized (0.05% trypsin in PBS containing 0.5 mM EDTA (GIBCO BRL) at 37° C. for two to five minutes) to separate and recover all the cells on the culture dish. The recovered whole cells of each cell line and 200,000 cells of whole bone marrow cells (derived from C57BL/6-Ly5.2 mouse, Charles River) were transplanted into C57BL/6-Ly5.2 mice (eight weeks age and male, Charles River) irradiated with X-ray at 8.5 Gy through the tail vein. After the transplantation, peripheral blood was collected from orbit at intervals, and the ratio in number of cells derived from the C57BL/6-Ly5.1 prep mouse was determined with FACS. The peripheral blood was analyzed according to the usual method (S. Kouzu, Fundamental techniques for immunology, YODOSHA, 1995). Three hundreds and fifty μL of distilled water was added to 50 μL of the peripheral blood, and the mixture was allowed to stand for 30 seconds so as to lyze the erythrocytes. Then, PBS at twice concentrations was added and the mixture was centrifuged to recover white blood cells. After the cells were washed once using the staining buffer (PBS containing 5% FCS and 0.05% NaN$_3$), anti-CD16 antibody, anti-Ly5.1 (CD45.1) antibody labeled with FITC, anti-Gr-1 and anti-CD11c antibodies labeled with phycoerythrin, and anti-CD45R (B220) and anti-CD90 (Thy1) antibodies labeled with allophycocyanin (all of these were purchased from Pharmingen) were added. After these cells were allowed to stand for reaction in the ice bath for 30 minites, they were washed with the staining buffer and FACS analysis was performed.

Change in the number of cells capable of reconstitution during the hematopoietic stem cell culture was determined by calculating the proportions of Ly5.1-positive cells in the Gr-1- or CD11c-positive cells (myeloid cells) and Ly5.1-positive cells in the CD90- or CD45R-positive cells (lymphoid cells) in the peripheral blood at intervals after transplantation.

Figure 3:
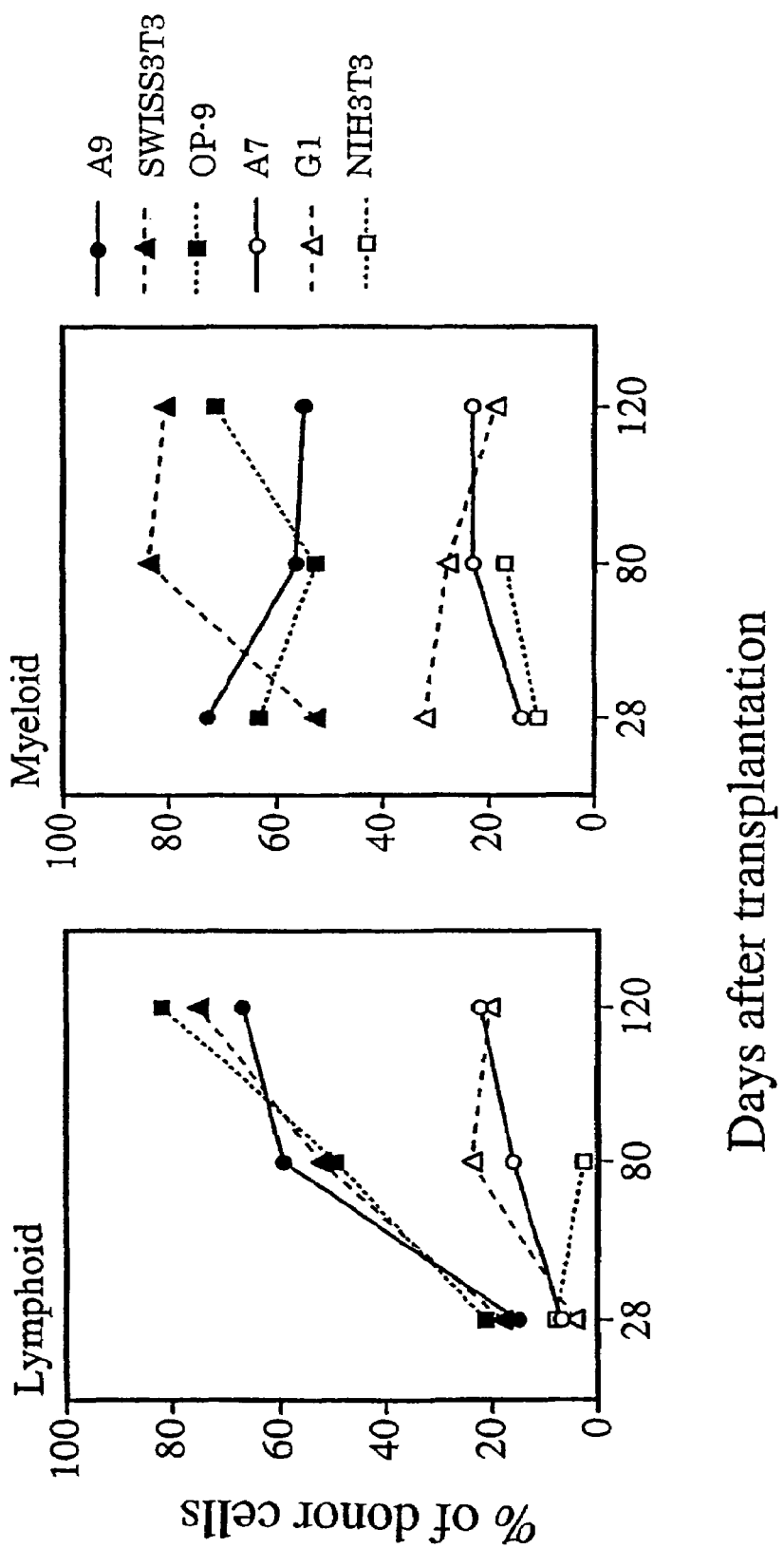
FIG. 3 shows time course of donor derived lymphoid lineage cells or myeloid lineage cells reconstitution in irradiated recipient mice that received the hematopoietic stem cells co-cultured with stromal cells.

FIG. 3 shows the results. When the cells were co-cultured with AGM-s3-A9 cells, OP9 cells, or 3T3Swiss cells, high chimerism of donor cells were maintained after the transplantation. Therefore, these stromal cells were considered to have a high activity to support the hematopoietic stem cells. In contrast, when the cells were co-cultured with AGM-s3-A7 cells, AGM-s3-G1 cells, or NIH3T3 cells, high chimerism derived from the transplanted cells was not observed. Therefore, these stromal cells were low in an activity to support the hematopoietic stem cells or the hematopoietic progenitor cells.

(IV) Identification of Sequences of Genes which Specifically Express in Hematopoietic Stem Cell-Supporting Cells AGM-s3-A9 cells, AGM-s3-A7 cells and OP9 cells were each dissolved in 20 mL of ISOGEN (Nippon gene, Japan) and total RNAs were prepared according to the attachment. Messenger RNAs were prepared from one milligram of the total RNAs according to the protocol of the mRNA purification kit (Amersham Pharmacia, U.S.A.). cDNAs were synthesized from the mRNAs and cDNA libraries (hereinafter, also called as AGM-s3-A9 cDNA, AGM-s3-A7 cDNA and OP9 cDNA, respectively) were constructed using pSPORT1 (GIBCO Lifetech, U.S.A.). A clone harboring a cDNA fragment which highly expresses specifically to AGM-s3-A9 cells or OP9 cells compared with AGM-s3-A7 cells was obtained from the libraries with SBH method (Hyseq, U.S.A.). A nucleotide sequence of the obtained clone was determined using ABI377 DNA sequencer (Perkin Elmer, U.S.A.).

As a result, it has been found that expression of genes comprising nucleotide sequences shown in SEQ ID NO:1, SEQ ID NO:2, SEQ ID NO:3, SEQ ID NO:4, SEQ ID NO:5, SEQ ID NO:6, and SEQ ID NO:7, or parts thereof in AGM-s3-A9 or OP9 cells is higher than that in AGM-s3-A7 cells. These genes were named as SCR-2, SCR-3, SCR-4, SCR-5, SCR-6, SCR-7 and SCR-8, respectively.

EXAMPLE 2

Cloning of SCR-2 and Activity Determination

By searching GenBank database for the nucleotide sequence shown in SEQ ID NO: 1 with BLAST, it has been found that SCR-2 is the same gene as a mouse gene, *Mus musculus* glypican-1 (GPC-1) of an accession number AF185613. The nuclotide sequence of ORF (Open Reading Frame) of SCR-2 and the amino acid sequence deduced from the nucleotide sequence are shown in SEQ ID NO: 8. Only the amino acid sequence is shown in SEQ ID NO: 9.

The human nucleotide sequence of GPC-1 is recorded in GenBank database under an accession number AX020122. The nucleotide sequence of ORF of AX020122 and the amino acid sequence deduced from the nucleotide sequence are shown in SEQ ID NO: 10. Only the amino acid sequence is shown in SEQ ID NO: 11.

Determination of the activity to support the hematopoietic stem cells or hematopoietic progenitor cells was performed as follows.

(1) Construction of Retrovirus Vector for Expression of Mouse SCR-2

Based on the nucleotide sequence of SCR-2 ORF, SCR-2Fsall and SCR-2Reco primers having the following nucleotide sequences were prepared, and PCR was performed using OP9 cDNA as a template.

```
SCR-2Fsal                        (SEQ ID NO: 30)
CCGGTCGACCACCatggaactccggacccgaggctgg SCR-2Reco                        (SEQ ID NO: 31)
CCGAATTCttaccgccacctgggcctggctgc
```

An amplified fragment was digested with restriction enzymes EcoRI and SalI. After electrophoresis, a DNA fragment was purified using JETSORB (Genomed, Germany). The purified DNA fragment was ligated with pMX-IRES-GFP vector digested with EcoRI and XhoI (gift form Professor T. Kitamura, TOKYO UNIV. INST. OF MEDICAL SCIENCE, Japan). The pMX-IRES-GFP vector is a plasmid obtained by inserting sequences encoding IRES (Internal Ribosome Entry Site) and GFP (Green Fluorescence Protein) into the retrovirus vector pMX. IRES enables ribosome to access to the middle of the mRNA. Therefore, two genes can be expressed from one mRNA by ligation of upward and downward genes separated by IRES in one transcription unit during the construction of an expression vector. With respect to the above-described plasmid, SCR-2 cDNA was inserted in the upward site and GFP (Green Fluorescence Protein) was inserted in the downward site. Thus, the expression of SCR-2 could be monitored by detecting the expression status of GFP using FACS.

The obtained recombinant vector was introduced into *E. coli* DH5α, and was seeded on LB agar medium containing 100 μg/ml of ampicillin, so that independent colonies were formed. After the isolated colony was cultured in 100 mL of LB medium containing 100 μg/ml of ampicillin, plasmid was purified using QIAGENtip100 (QIAGEN, U.S.A.). The sequence of the inserted gene was determined using a conventional method, so that the sequence was confirmed to be identical to the nucleotide sequence of SCR-2 ORF.

(2) Preparation of Stromal Cells Highly Expressing SCR-2

BOSC23 cells were seeded on a collagen type I-coated 60-mm dish (Asahi technoglass) at $2 \times 10^6$ cells/dish, and cultured in DMEM medium (GIBCO BRL) containing 10% FCS at 37° C., under an atmosphere of 5% $CO_2$, and at a humidity of 100%. Twelve to 18 hours after the start of the culture, the medium was replaced by two milliliters of OPTI MEM medium (GIBCO BRL).

About 3 μg of plasmid obtained by inserting SCR-2 into the above described pMX-IRES-GFP was added to 18 μl of LIPOFECTAMINE Reagent (GIBCO BRL) diluted with 100 µl of OPTI MEM medium, and the mixture was allowed to stand at room temperature for 30 min. The prepared DNA solution was added to the prepared BOSC23 cell culture solution. After about five hours, two milliliters of DMEM medium containing 20% FCS (GIBCO BRL) was added.

After about 24 hours, the medium was replaced by 4 ml of DMEM containing 10% FCS. Further, after about 48 hours, the culture medium was harvested. After the culture medium was filtrated through 0.45-µm filter, the filtrate was centrifuged at 1,200 g for 16 hours and the supernatant was removed to obtain the virus precipitation.

AGM-s3-A7 or AGM-s3-A9 cells were cultured in one milliliter of MEMa medium containing 10% FCS (GIBCO BRL) on a 24-well culture dish (FALCON) at $1 \times 10^4$ cells/well. After 12 to 18 hours, the virus precipitation was suspended in one milliliter of MEMa medium containing 10% FCS, and the stromal cell culture medium was replaced by the virus suspension. Next, POLYBRENE (Sigma, SEQUA-BRENE) was added to be 10 µg/ml. After the culture dish was centrifuged at 700 g for 45 minutes, the cells were cultured at 37° C., under an atmosphere of 5% $CO_2$, and at a humidity of 100%. After 48 hours, the medium was replaced by one milliliter of MEMa medium containing 10% FCS. After 24 hours, the cells were subcultured on a 6-well culture dish (FALCON) and cultured in three milliliters of MEMa medium containing 10% FCS. Forty-eight hours after the subculturing, GFP expression in the stromal cells was detected using a cell sorter (FACSVantage, Becton Dickinson) to indirectly confirm that not less than 80% of cells expressed SCR-2.

Also, the same procedures were repeated by using pMX-IRES-GFP vector instead of the plasmid obtained by inserting SCR-2 into pMX-IRES-GFP to prepare stromal cells into which a control vector was introduced.

(3) Co-Culture of Human Hematopoietic Stem Cells and Stromal Cells Highly Expressing SCR-2, and Determination of Proliferation Statuses of Hematopoietic Stem Cells and Hematopoietic Progenitor Cells by Clonogenic Assay In the same manner as described in (III) (1) 3) to 4) of Example 1, AGM-s3-A9 or AGM-s3-A7 cells in which SCR-2 was highly expressed through retrovirus, AGM-s3-A9 or AGM-s3-A7 cells into which a control vector was introduced, or AGM-s3-A9 or AGM-s3-A7 cells were co-cultured with CD34-positive hematopoietic stem cells derived from human cord blood, and proliferation statuses of hematopoietic stem cells and hematopoietic progenitor cells are determined.

Figure 4:
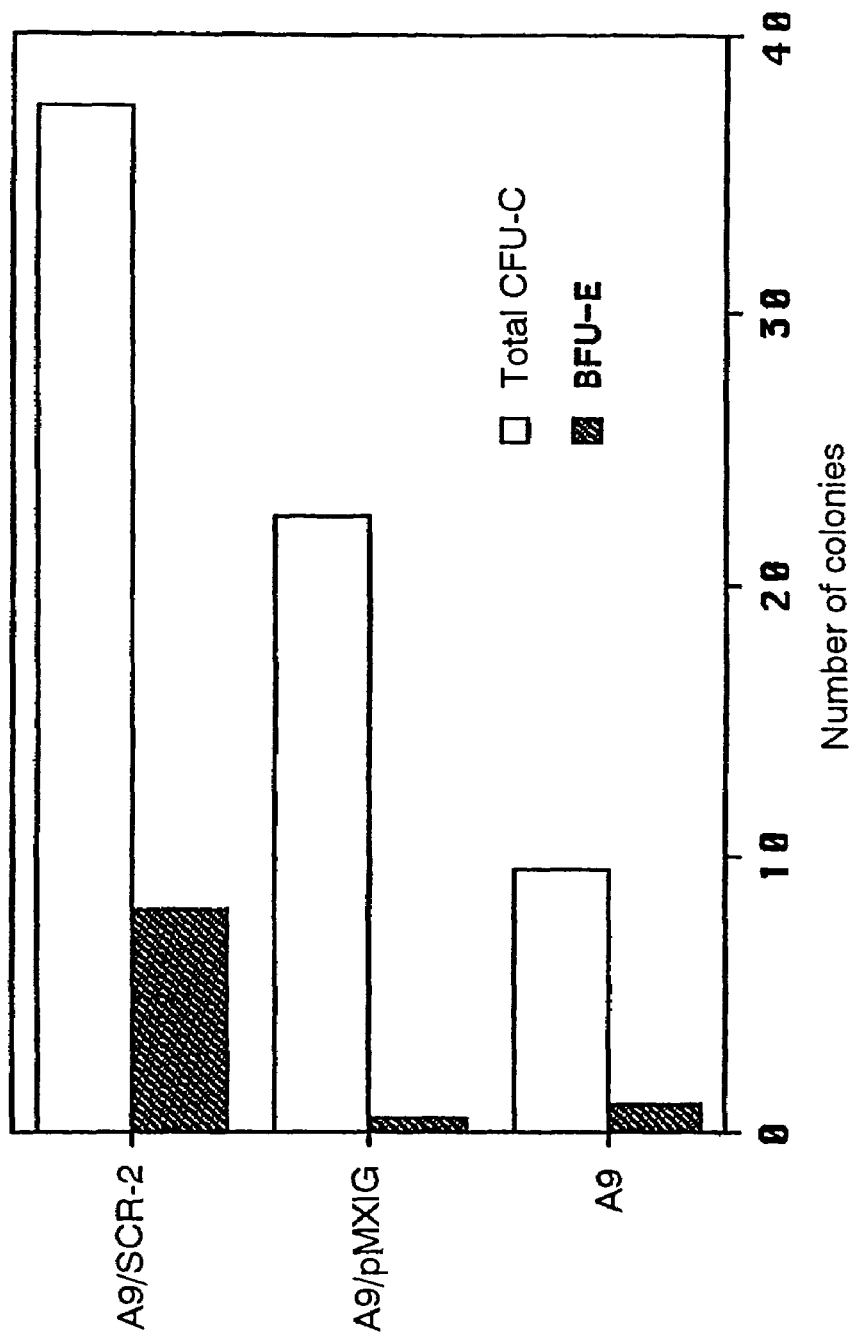
FIG. 4 shows proliferation statuses of hematopoietic stem cells and hematopoietic progenitor cells determined by a clonogenic assay after co-culture of CD34-positive hematopoietic stem cells with AGM-S3-A9 cells in which a gene SCR-2 is highly expressed (A9/SCR-2), AGM-S3-A9 cells into which a control vector is introduced (A9/pMXIG) or AGM-S3-A9 cells (A9) for two weeks.
Figure 5:
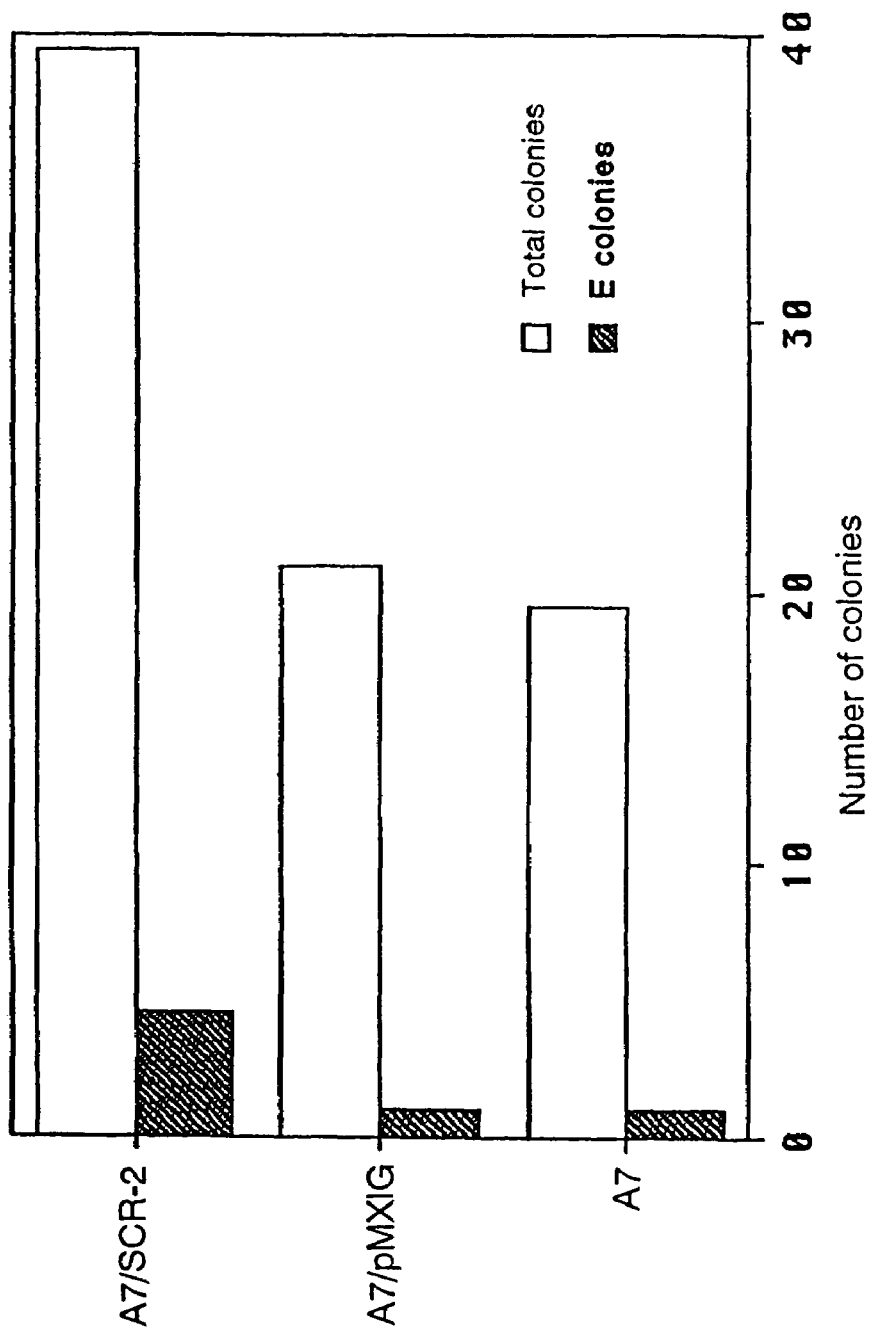
FIG. 5 shows proliferation statuses of hematopoietic stem cells and hematopoietic progenitor cells determined by a clonogenic assay after co-culture of CD34-positive hematopoietic stem cells with AGM-S3-A7 cells in which a gene SCR-2 is highly expressed (A7/SCR-2), AGM-S3-A7 cells into which a control vector is introduced (A7/pMXIG) or AGM-S3-A7 cells (A7) for two weeks.

FIG. 4 shows results when the CD34-positive hematopoietic stem cells were co-cultured with AGM-S3-A9 cells in which SCR-2 was highly expressed (A9/SCR-2), AGM-S3-A9 cells into which a control vector was introduced (A9/pMXIG) or AGM-S3-A9 cells (A9) for two weeks. Also, FIG. 5 shows results when the CD34-positive hematopoietic stem cells were co-cultured with AGM-S3-A7 cells in which SCR-2 was highly expressed, AGM-S3-A7 cells into which a control vector was introduced or AGM-S3-A7 cells for two weeks. As a result, by the co-culture with AGM-S3-A9 cells in which SCR-2 was highly expressed or AGM-S3-A7 cells in which SCR-2 was highly expressed, increases of BFU-E and CFU-C were observed. Therefore, it has been revealed that the activity to support hematopoietic stem cells or hematopoietic progenitor cells, of AGM-S3-A9 or AGM-S3-A7 increases by allowing SCR-2 to be highly expressed. From the results, it has revealed that a gene product of SCR-2 has an activity to support survival or proliferation of hematopoietic stem cells or hematopoietic progenitor cells or an activity to affect stromal cells to enhance a hematopoietic cell-supporting activity of the stromal cells or impart the activity to the stromal cells.

EXAMPLE 3

Cloning of SCR-3 and Activity Determination

By searching GenBank database for the nucleotide sequence shown in SEQ ID NO: 2 with BLAST, it has been found that SCR-3 is the same gene as mouse genes, *Mus musculus* chemokine MMRP2 mRNA of an accession number U15209, *Mus musculus* C10-like chemokine mRNA of U19482 and mouse macrophage inflammatory protein-lgamma mRNA of U49513. The nuclotide sequence of SCR-3 ORF and the amino acid sequence deduced from the nucleotide sequence are shown in SEQ ID NO: 12. Only the amino acid sequence is shown in SEQ ID NO: 13.

Determination of the activity of SCR-3 to support the hematopoietic stem cells or hematopoietic progenitor cells was performed as follows.

(1) Construction of Retrovirus Vector for Expression of Mouse SCR-3

Based on the nucleotide sequence of SCR-3 ORF, SCR-3FxhoI and SCR-3Reco primers having the following nucleotide sequences were prepared, and PCR was performed using AGM-s3-A9 cDNA as a template. An amplified fragment was inserted to the retrovirus vector pMX-IRES-GFP in the same manner as described in (1) of Example 2.

```
SCR-3FxhoI                      (SEQ ID NO: 32)
ccgCTCGAGccaccATGAAGCCTTTTCATACTGCC SCR-3Reco                       (SEQ ID NO: 33)
tccGAATTCttattgtttgtaggtccgtgg
```

(2) Preparation of Stromal Cells Highly Expressing SCR-3

AGM-s3-A7 cells in which SCR-3 was highly expressed were prepared by using the above retrovirus vector in the same manner as (2) of Example 2.

(3) Determination of Activity to Support Hematopoietic Stem Cells of Stromal Cells in which SCR-3 is Highly Expressed In the same manner as described in (III) (2) of Example 1, determination of the activity to support hematopoietic stem cells was performed except that AGM-S3-A7 cells, AGM-S3-A7 cells in which SCR-3 was highly expressed through retrovirus, and AGM-S3-A7 cells into which a control vector was introduced were seeded in a 24-well culture dish (Falcon) at $1 \times 10^5$ cells/well.

Figure 6:
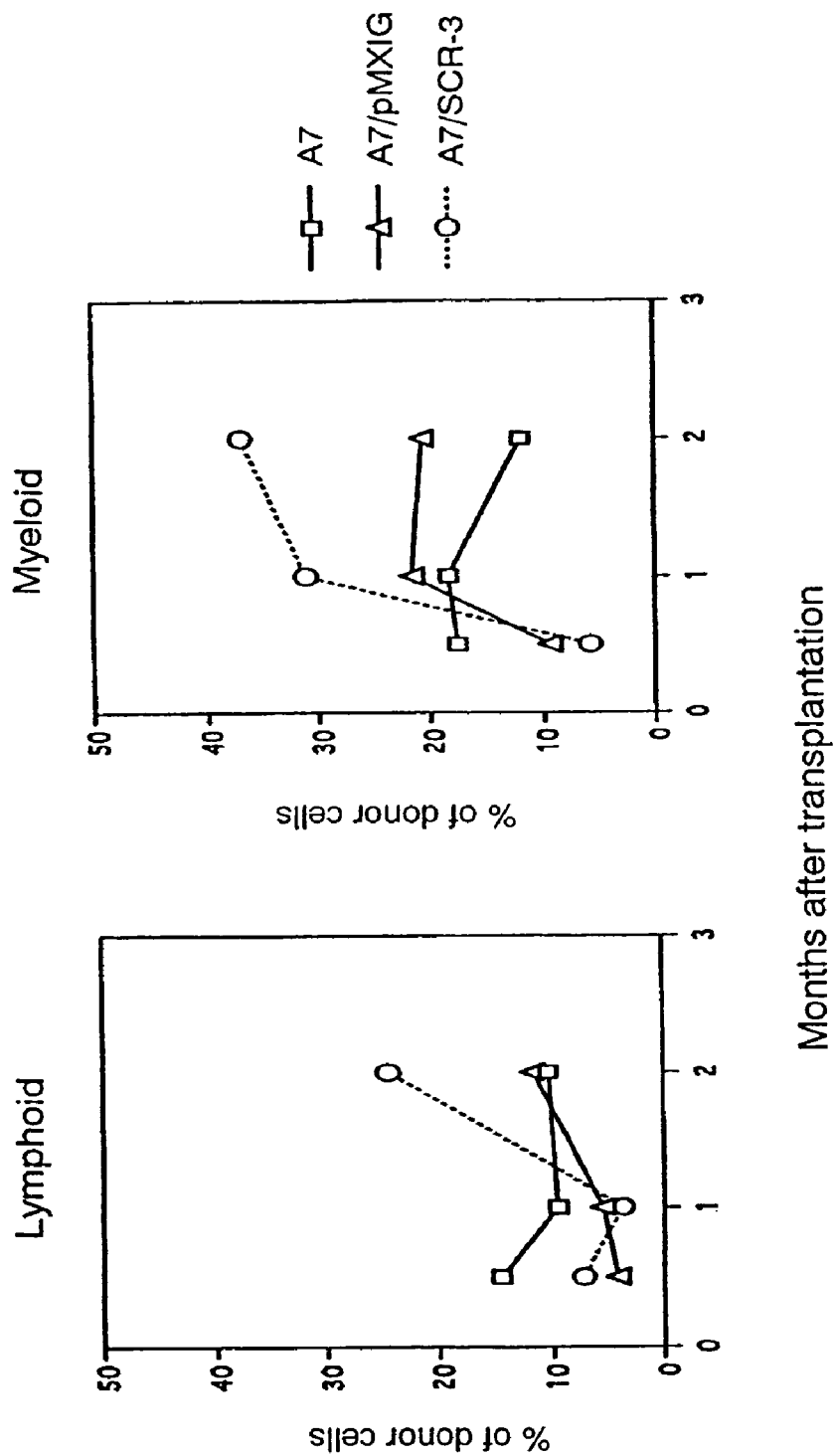
FIG. 6 shows time course of donor derived lymphoid lineage cells or myeloid lineage cells reconstitution in peripheral blood of irradiated recipient mice that received the hematopoietic stem cells co-cultured with AGM-S3-A7 cells in which a gene SCR-3 is highly expressed (A7/SCR-3), AGM-S3-A7 cells into which a control vector is introduced (A7/pMXIG) or AGM-S3-A7 cells.
Figure 7:
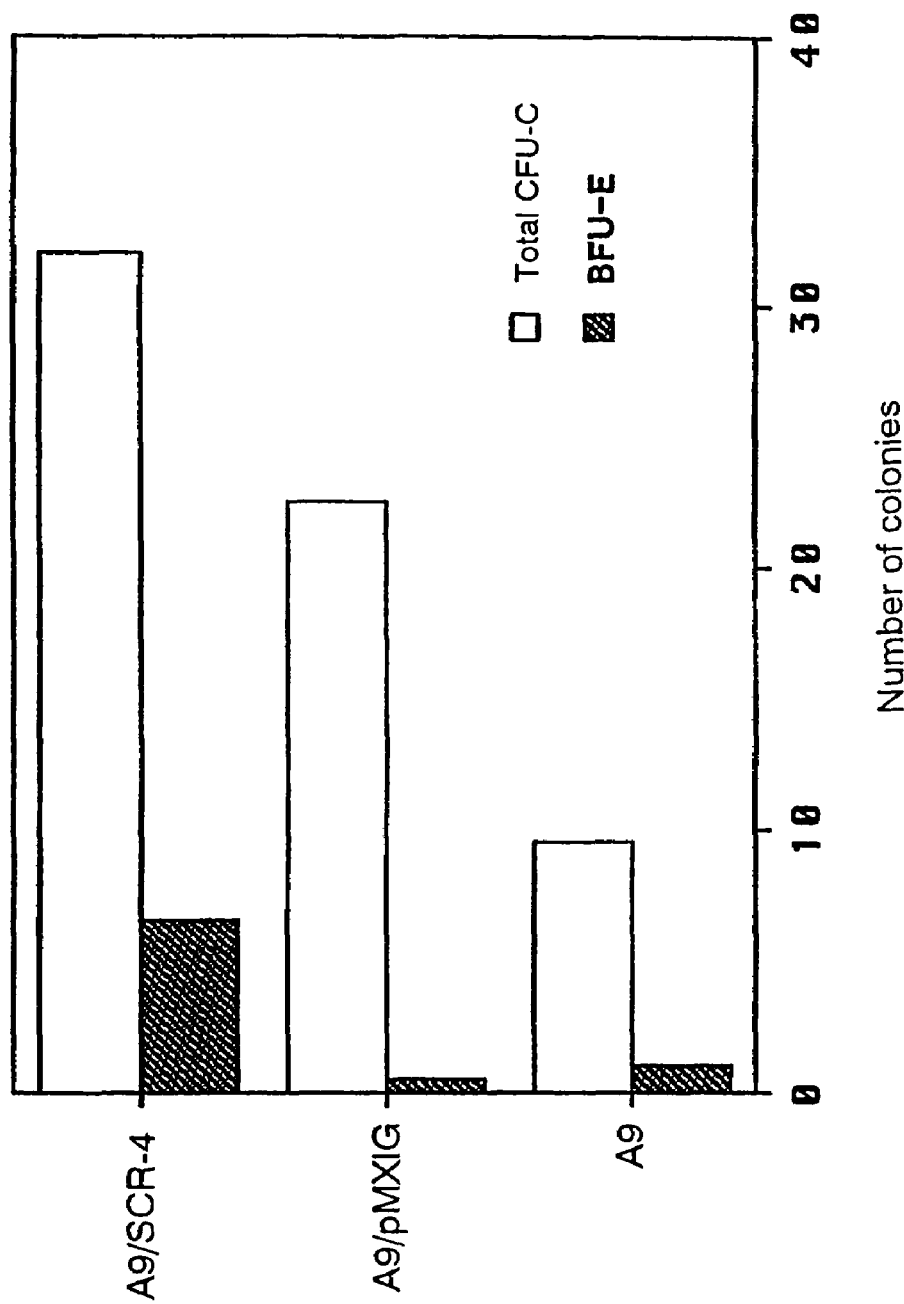
FIG. 7 shows proliferation statuses of hematopoietic stem cells and hematopoietic progenitor cells determined by a clonogenic assay after co-culture of CD34-positive hematopoietic stem cells with AGM-S3-A9 cells in which a gene SCR-4 is highly expressed (A9/SCR-4), AGM-S3-A9 cells into which a control vector is introduced (A9/pMXIG) or AGM-S3-A9 cells (A9) for two weeks.

The results are shown in FIG. 6. Hematopoietic cells co-cultured with AGM-s3-A7 cells in which SCR-3 was highly expressed (A7/SCR-3) showed high chimerism in recipient individuals after the transplantation compared with the parent cell lines or hematopoietic cells co-cultured with the cells into which a control vector was introduced. The high chimerism was observed in myeloid and lymphoid cells two months after the transplantation. Therefore, it is revealed that hematopoietic stem cells and hematopoietic progenitor cells which can reconstitute the hematopoietic system in bodies of irradiated mice have maintained and amplified superiorly to the co-culture with cells into which SCR-3 is not introduced, during the co-culture period. From the results, it is revealed that an activity of stromal cells to support survival or proliferation of hematopoietic stem cells or hematopoietic progenitor cells is increased by high expression of SCR-3. Therefore, it is revealed that a gene product of SCR-3 has an activity to affect hematopoietic stem cells or hematopoietic progenitor cells to support survival or proliferation thereof or an activity to affect stromal cells to enhance a hematopoietic cell-supporting activity of the stromal cells or impart the activity to the stromal cells.

EXAMPLE 4

Cloning of SCR-4 and Activity Determination

By searching GenBank database for the nucleotide sequence shown in SEQ ID NO: 3 with BLAST, it has been found that SCR-4 has a high homology to *Homo sapiens* clone 25077 mRNA of an accession number AF131820, and that SCR-4 is a mouse ortholog. This sequence is described in WO 00/66784.

The nuclotide sequence of ORF of AF131820 and the amino acid sequence deduced from the nucleotide sequence are shown in SEQ ID NO: 16. Only the amino acid sequence is shown in SEQ ID NO: 17.

The nuclotide sequence of ORF of SCR-4 and the amino acid sequence deduced from the nucleotide sequence are shown in SEQ ID NO: 14. Only the amino acid sequence is shown in SEQ ID NO: 15.

Determination of the activity of SCR-4 to support the hematopoietic stem cells or hematopoietic progenitor cells was performed as follows.

(1) Construction of Retrovirus Vector for Expression of Human SCR-4

From 3 µg of mRNA derived from fetal liver (CLONETEC, U.S.A.), cDNA was synthesized by using oligo-dT primer and reverse transcriptase (SuperscriptII, GIBCO-BRL). Using the cDNA as a template, the ORF region of human SCR-4 was amplified by PCR with HSCR-4FxhoI and HSCR-4RecoRV primers having the following nucleotide sequences. An amplified fragment was digested with XhoI and inserted to the retrovirus vector pMX-IRES-GFP in the same manner as described in (1) of Example 2. For the insertion, the pMX-IRES-GFP was digested with a restriction enzyme EcoRI, blunt-ended with KOD DNA synthase (TOYOBO, Japan) and digested with a restriction enzyme XhoI.

```
HSCR-4FxhoI                      (SEQ ID NO: 34)
CCGCTCGAGCCACCatgttggctgcaaggctggtgt HSCR-4RecoRV                     (SEQ ID NO: 35)
CCGGATATCtcatttctttctgttgcctcca
```

(2) Preparation of Stromal Cells Highly Expressing Human SCR-4

AGM-s3-A9 cells in which human SCR-4 was highly expressed were prepared by using the above retrovirus vector in the same manner as (2) of Example 2.

(3) Co-Culture of Human Hematopoietic Stem Cells and Stromal Cells Highly Expressing Human SCR-4, and Determination of Proliferation Statuses of Hematopoietic Stem Cells and Hematopoietic Progenitor Cells by Clonogenic Assay In the same manner as described in (III) (1) 3) to 4) of Example 1, AGM-s3-A9 cells in which SCR-4 was highly expressed through retrovirus, AGM-s3-A9 cells into which a control vector was introduced, or AGM-s3-A9 cells were co-cultured with CD34-positive hematopoietic stem cells derived from human cord blood, and proliferation statuses of hematopoietic stem cells and hematopoietic progenitor cells are determined.

FIG. 6 shows results when the CD34-positive hematopoietic stem cells were co-cultured with AGM-S3-A9 cells in which human SCR-4 was highly expressed, AGM-S3-A9 cells into which a control vector was introduced or AGM-S3-A9 cells for two weeks. As a result, the co-culture with AGM-S3-A9 cells in which human SCR-4 was highly expressed, increases of BFU-E and CFU-C were observed. Therefore, it has been revealed that the activity to support hematopoietic stem cells or hematopoietic progenitor cells, of AGM-S3-A9 increases by allowing human SCR-4 to be highly expressed. From the results, it has been revealed that human SCR-4 has an activity to support survival or proliferation of hematopoietic stem cells or hematopoietic progenitor cells or an activity to affect stromal cells to impart a hematopoietic cell-supporting activity to the stromal cells.

EXAMPLE 5

Cloning of SCR-5 and Activity Determination

In the nucleotide sequence of SEQ ID NO: 4 obtained by the SBH analysis, the presence of ORF was predicted. The nuclotide sequence of ORF and the amino acid sequence deduced from the nucleotide sequence are shown in SEQ ID NO: 18. Only the amino acid sequence is shown in SEQ ID NO: 19.

By searching GenBank database for the nucleotide sequence of SEQ ID NO: 18 with BLAST, it has been found that SCR-5 has a high homology with *Homo sapiens* esophageal cancer related gene 4 portein (ECRG4) mRNA of an accession number AF325503, and that SCR-5 is a mouse ortholog of AF325503. The nucleotide sequence of ORF of AF325503 and the amino acid sequence deduced from the nucleotide sequence are shown in SEQ ID NO: 20. Only the amino acid sequence is shown in SEQ ID NO: 21.

Determination of the activity of SCR-5 to support the hematopoietic stem cells or hematopoietic progenitor cells was performed as follows.

(1) Construction of Retrovirus Vector for Expression of Mouse SCR-5

Based on the nucleotide sequence of SCR-5 ORF, SCR-5FxhoI and SCR-5Rblunt primers having the following nucleotide sequences were prepared for retrovirus cloning, and PCR was performed using DNA having the nucleotide sequence shown in SEQ ID NO: 23 as a template. An amplified fragment was digested with a restriction enzyme XhoI and inserted to the retrovirus vector pMX-IRES-GFP in the same manner as described in (1) of Example 2. For the insertion, the pMX-IRES-GFP was digested with a restriction enzyme EcoRI, blunt-ended with KOD DNA synthase (TOYOBO, Japan) and digested with a restriction enzyme XhoI.

```
SCR-5FxhoI                       (SEQ ID NO: 36)
ccgCTCGAGccaccatgagcacctcgtctgcgcg SCR-5Rblunt                      (SEQ ID NO: 37)
tccGTTAACttaatagtcatcatagttca
```

(2) Preparation of Stromal Cells Highly Expressing SCR-5

AGM-s3-A7 cells in which SCR-5 was highly expressed were prepared by using the above retrovirus vector in the same manner as (2) of Example 2.

(3) Determination of Activity to Support Hematopoietic Stem Cells of Stromal Cells in which SCR-5 is Highly Expressed In the same manner as described in (3) of Example 3, determination of the activity to support hematopoietic stem cells was performed.

Figure 8:
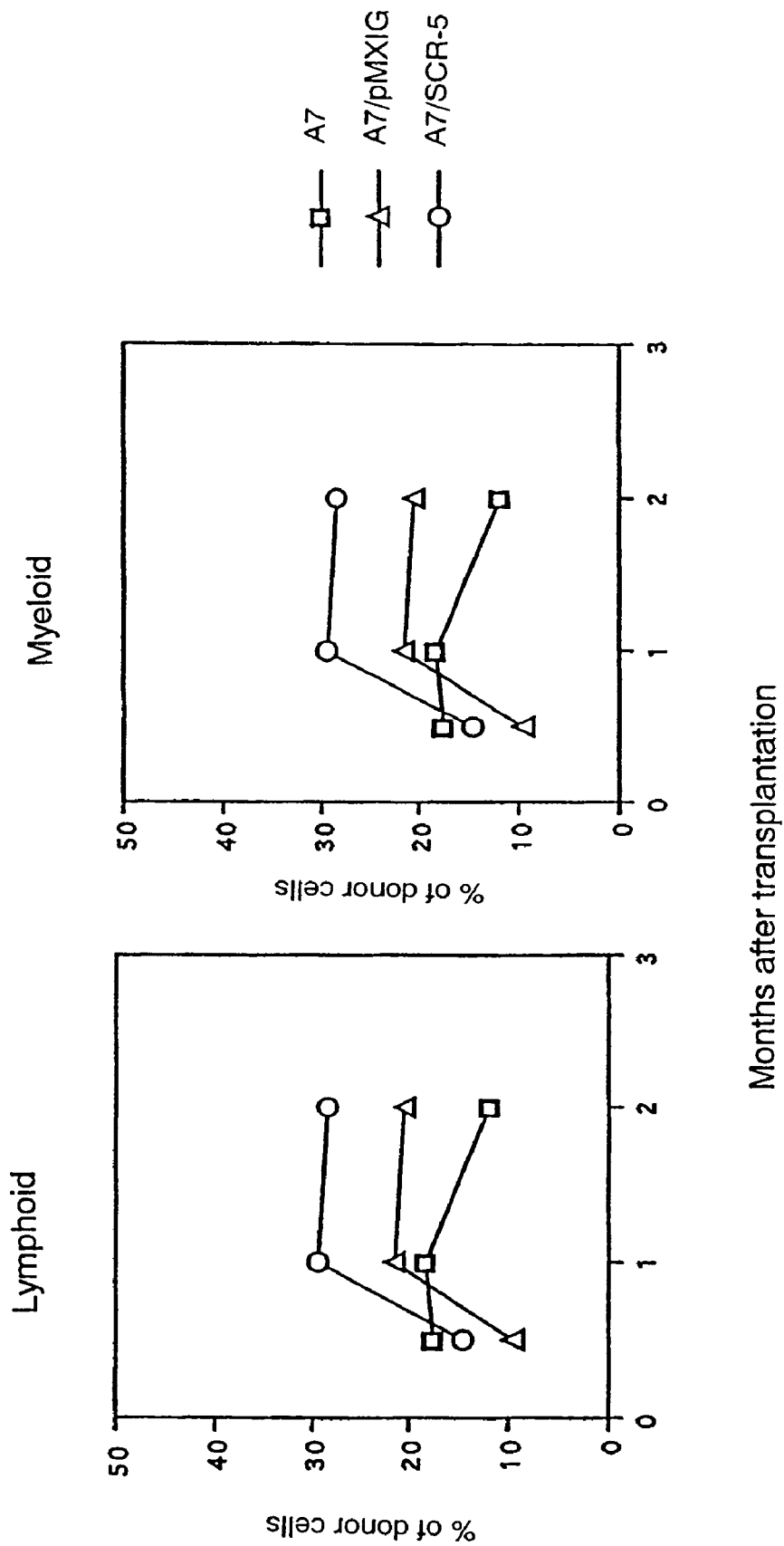
FIG. 8 shows time course of donor derived lymphoid lineage cells or myeloid lineage cells reconstitution in peripheral blood of irradiated recipient mice that received the hematopoietic stem cells co-cultured with AGM-S3-A7 cells in which a gene SCR-5 is highly expressed (A7/SCR-5), AGM-S3-A7 cells into which a control vector is introduced (A7/pMXIG) or AGM-S3-A7 cells.

The results are shown in FIG. 8. Hematopoietic cells co-cultured with AGM-s3-A7 cells in which SCR-5 was highly expressed (A7/SCR-5) showed high chimerism in recipient individuals after the transplantation compared with the parent cell lines or hematopoietic cells co-cultured with the cells into which a control vector was introduced. The high chimerism was observed in myeloid and lymphoid cells two months after the transplantation. Therefore, it is revealed that hematopoietic stem cells and hematopoietic progenitor cells which can reconstitute the hematopoietic system in bodies of irradiated mice have maintained and amplified superiorly to the co-culture with cells into which SCR-5 is not introduced, during the co-culture period. From the results, it is revealed that an activity of stromal cells to support survival or proliferation of hematopoietic stem cells or hematopoietic progenitor cells is increased by high expression of SCR-5. Therefore, it is revealed that a gene product of SCR-5 has an activity to affect hematopoietic stem cells or hematopoietic progenitor cells to support survival or proliferation thereof or an activity to affect stromal cells to enhance a hematopoietic cell-supporting activity of the stromal cells or impart the activity to the stromal cells.

EXAMPLE 6

Cloning of SCR-6 and Activity Determination

Based on the nucleotide sequence of SEQ ID NO: 5, a probe was prepared and AGM-s3-A9 cDNA was screened by hybridization to obtain a gene containing ORF of mouse SCR-6.

AGM-s3-A9 cells (1.4×10$^8$ cells) were dissolved in 20 mL of ISOGEN (Nippon gene, Japan) and total RNAs were prepared according to the attachment. Messenger RNAs were prepared from one milligram of the total RNAs according to the protocol of the mRNA purification kit (Amersham Pharmacia, U.S.A.). By using SMART cDNA library construction kit (CLONTECH, U.S.A.), cDNA libraries divided to 15 fractions were prepared from the 2 μg of the prepared mRNAs according to the attachment. The libraries contained about 400,000 of independent clones in total. For each fraction, PCR was performed under the following conditions to identify a fraction containing SCR-6 cDNA.

Based on the sequence of a partial fragment of the mouse SCR-6 gene, the following primers were prepared, and PCR was performed with 35 cycles of 94° C., 30 seconds, 55° C., 30 seconds and 72° C., 1 minute, by using each fraction of AGM-s3-A9 cDNA libraries as a template.

```
SCR-6F
AGCTCATTACTGTATATTTA (SEQ ID NO: 22; 1971-1990)
(SEQ ID NO: 38)

SCR-6R
GCTATATTTCATAAGTCATC (SEQ ID NO: 22; 2330-2349)
(SEQ ID NO: 39)
```

The PCR product was subjected to 2% agarose gel electrophoresis and a fraction from which the PCR product having the expected size was obtained was identified. For each of two fractions among the positive fractions, 50,000 plaques were seeded on two 15-cm petri dishes and incubated 37° C. for 10 hours. Then, plaques of each petri dish were replicated to a sheet of Biodyne nylon filter (Pall, U.S.A.). The replicated nylon filter was subjected to DNA fixation treatment according to the attachment, and screening with $^{32}$P-labeled DNA probe was performed.

The probe was prepared as follows. PCR was performed with 35 cycles of 94° C., 30 seconds, 55° C., 30 seconds and 72° C., 1 minute, by using SCR-6F and SCR-6R and the plasmid containing a partial fragment of the mouse SCR-6 gene as a template. The PCR product was subjected to 2% agarose gel electrophoresis and the amplified fragment was purified by JETSORB. By using 25 ng of the obtained PCR fragment, $^{32}$P-labeled DNA probe was prepared with Megaprime labeling kit (Amersham Pharmacia, U.S.A.).

Hybridization and washing were performed with ExpressHybSolution (CLONETECH, U.S.A.) according to the attachment. An X-ray film was exposed to the filter and developed with a Fuji film auto developer to analyze the result. A plaque at a position corresponding to the resultant strongly exposed portion was scraped from the petri dish, and seeded again so that about 200 of plaques should appear on 10-cm petri dish. Screening was again performed according to the above-mentioned method to isolate a single plaque. The obtained phage clone was transfected to E. coli strain BM25.8 according to the attachment of SMART cDNA library construction kit, and allowed to be converted to plasmid in the cells to form colony on LB agar medium containing 50 μg/ml ampicilin. A single colony of the transfected E. coli was inoculated to 3 ml of LB medium containing 50 μg/ml ampicilin and cultured at 30° C. overnight. Plasmid was extracted with RPM kit (BIO101, U.S.A.) to obtain about 10 mg of plasmid.

Sequencing the both ends of the inserted fragment with an ABI377 DNA sequencer by using λTriplEx5'LD-Insert Screening Amplimer (CTCGGGAAGCGCGCCATTGTGT-TGGT (SEQ ID NO: 40); CLONTECH, U.S.A.) revealed that it included cDNA containing the nucleotide sequence from nucleotide 1 of SEQ ID NO: 5. The full-length nucleotide sequence was also determined with the ABI377 DNA sequencer. The nuclotide sequence and the amino acid sequence deduced from a nucleotide sequence predicted as ORF in the nucleotide sequence are shown in SEQ ID NO: 22. Only the amino acid sequence is shown in SEQ ID NO: 23.

By searching the cDNA database of KAZUSA DNA Institute for mouse SCR-6 nucleotide sequence with BLAST, it has been found homologous Homo sapiens clone HJ08186R. HJ08186R has a high homology to the nucleotide sequence from guanine at nucleotide position 319 to adenine at nucleotide position 917 of mouse SCR-6, but is not predicted to have an entire ORF sequence.

KF305X primer; 5'-CCG CTC GAG CCG CCC AGA TGC AGT TTC GC-3' (SEQ ID NO: 49) having Xho I site at 5'-end was prepared according to the nucleotide sequence of HJ08186R, 5'-CCG CCC AGA TGC AGT TTC GC-3' (nucleotide position: 10-29 in SEQ ID NO: 49), which is homologous to predicted initial methionine coding region of mouse SCR-6. 3'-RACE was performed with KOD-PLUS- (TOYOBO #KOD201) for the DNA polymerase and the enzyme reaction system by following protocol in the package insert. Primers used for amplification were KF305X primer for 5'-end primer and AP1 primer in Marathon Ready cDNA (CLONTECH) for 3'-end primer (0.2 μM of each final concentration). Marathon Ready cDNA Human Fetal Liver (CLONTECH#7403-1) was used as a template. PCR was performed with GeneAmp PCR System 9700 (Applied Biosystems). Amplification was performed with 94° C. for 5 minutes; 5 cycles of 94° C., 10 seconds, 72° C., 4 minutes; 5 cycles of 94° C., 10 seconds, 70° C., 4 minutes; 20 cycles of 94° C., 10 seconds, 68° C., 4 minutes; 72° C. for 7 minutes and thereafter 4° C. By using 1/50 volume (1 µl) of the amplified product, 2$^{nd}$ amplification was further performed with KF305X primer for 5'-end primer and AP2 primer for 3'-end primer (0.2 µM of each final concentration). The 2$^{nd}$ amplification was performed with 94° C. for 5 minutes; 5 cycles of 94° C., 10 seconds, 72° C., 4 minutes; 5 cycles of 94° C., 10 seconds, 70° C., 4 minutes; 35 cycles of 94° C., 10 seconds, 68° C., 4 minutes; 72° C. for 7 minutes and thereafter 4° C. As a result, an amplified band of about 2 kilo base pairs was obtained.

The 2$^{nd}$ amplified product was incubated with dNTPs (40 µM of final concentration) and 5 units of Takara Taq (Takara Shuzo#R001A) at 72° C. for 7 minutes and subjected to agarose gel electrophoresis. A DNA fragment about 2 kilo base pairs in size was identified and purified by JETSORB Gel Extraction Kit (Genomed#110150). The purified DNA fragment was inserted to the pGEM-T Easy vector (Promega) by conventional method.

The nucleotide sequences of obtained clones were determined with the ABI377 DNA sequencer (Applied Biosystems). The nucleotide sequence and amino acid sequence deduced from a nucleotide sequence predicted as ORF are shown in SEQ ID NO: 47. Only the amino acid sequence is shown in SEQ ID NO: 48. The nucleotide sequence contains a predicted ORF of 732 base pairs in size (nucleotide position: 18-749 in SEQ ID NO: 47) and has homology with the mouse SCR-6 coding region at 92.3% (nucleotide sequence) and 95.9% (amino acid sequence). Thus, the sequence was identified as a counterpart of mouse SCR-6 in human and defined as human SCR-6. The homology was determined with homology search in the compare function of DNASIS version 3.7 (Hitachi Software Engineering).

Determination of the activity of SCR-6 to support the hematopoietic stem cells or hematopoietic progenitor cells was performed as follows.

(1) Construction of Retrovirus Vector for Expression of Mouse SCR-6

Based on the nucleotide sequence of SCR-6 ORF, SCR-6FxhoI and SCR-6Reco primers having the following sequences were prepared for retrovirus cloning, and PCR was performed by using DNA having the nucleotide sequence shown in SEQ ID NO: 22 as a template. An amplified fragment was inserted to the retrovirus vector pMX-IRES-GFP in the same manner as described in (1) of Example 2.

```
SCR-6FxhoI
ccgctcgagccaccATGCGTTTTTGCCTCTCTC      (SEQ ID NO: 41)

SCR-6Reco
cggaattcTTATTGGTTCACTCTGTCTG           (SEQ ID NO: 42)
```

(2) Preparation of Stromal Cells Highly Expressing SCR-6

AGM-s3-A9 cells in which SCR-6 was highly expressed were prepared by using the above retrovirus vector in the same manner as (2) of Example 2.

(3) Co-Culture of Human Hematopoietic Stem Cells and Stromal Cells Highly Expressing SCR-6, and Determination of Proliferation Statuses of Hematopoietic Stem Cells and Hematopoietic Progenitor Cells by Clonogenic Assay In the same manner as described in (III) (1) 3) to 4) of Example 1, AGM-s3-A9 cells in which SCR-6 was highly expressed through retrovirus, AGM-s3-A9 cells into which a control vector was introduced, or AGM-s3-A9 cells were co-cultured with CD34-positive hematopoietic stem cells derived from human cord blood, and proliferation statuses of hematopoietic stem cells and hematopoietic progenitor cells are determined.

Figure 9:
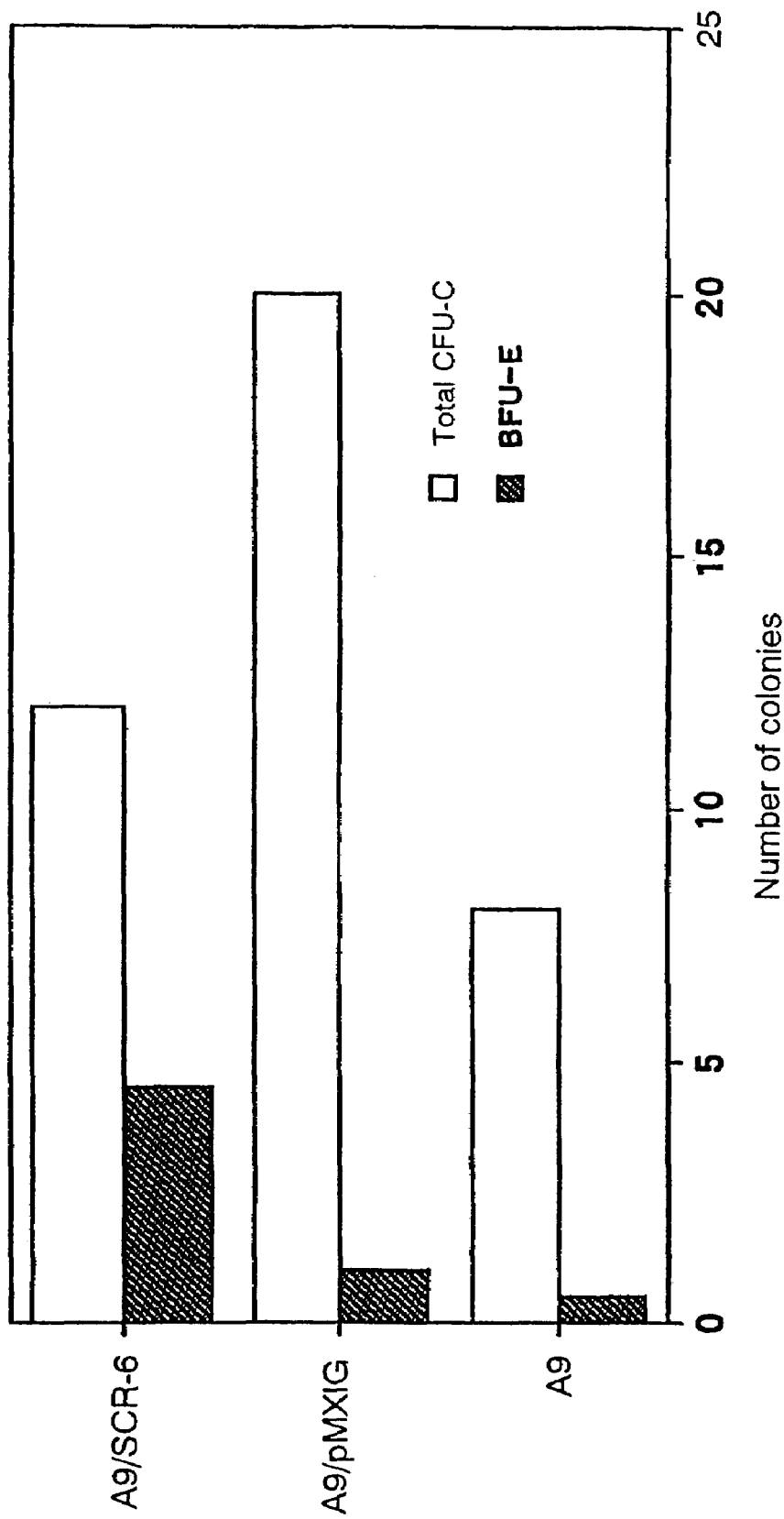
FIG. 9 shows proliferation statuses of hematopoietic stem cells and hematopoietic progenitor cells determined by a clonogenic assay after co-culture of CD34-positive hematopoietic stem cells with AGM-S3-A9 cells in which a gene SCR-6 is highly expressed (A9/SCR-6), AGM-S3-A9 cells into which a control vector is introduced (A9/pMXIG) or AGM-S3-A9 cells (A9) for two weeks.

FIG. 9 shows results when the CD34-positive hematopoietic stem cells were co-cultured with AGM-S3-A9 cells in which SCR-6 was highly expressed (A9/SCR-9), AGM-S3-A9 cells into which a control vector was introduced (A9/pMXIG) or AGM-S3-A9 cells (A9) for two weeks. As a result, the co-culture with AGM-S3-A9 cells in which SCR-6 was highly expressed, increases of BFU-E and CFU-C were observed. Therefore, it has been revealed that the activity to support hematopoietic stem cells or hematopoietic progenitor cells, of AGM-S3-A9 increases by allowing SCR-6 to be highly expressed. From the results, it has been revealed that the gene product of SCR-6 has an activity to support survival or proliferation of hematopoietic stem cells or hematopoietic progenitor cells or an activity to affect stromal cells to enhance a hematopoietic cell-supporting activity of the stromal cells or impart the activity to the stromal cells.

EXAMPLE 7

Cloning of SCR-7 and Activity Determination

In the nucleotide sequence of SEQ ID NO: 6 obtained by the SBH analysis, the presence of ORF was predicted. The nuclotide sequence of ORF and the amino acid sequence deduced from the nucleotide sequence are shown in SEQ ID NO: 24. Only the amino acid sequence is shown in SEQ ID NO: 25.

Determination of the activity of SCR-7 to support the hematopoietic stem cells or hematopoietic progenitor cells was performed as follows.

(1) Construction of Retrovirus Vector for Expression of Mouse SCR-7

Based on the nucleotide sequence of SCR-7 ORF, SCR-7FsalI and SCR-7Reco primers having the following nucleotide sequences were prepared for retrovirus cloning, and PCR was performed using DNA having the nucleotide sequence shown in SEQ ID NO: 24 as a template. An amplified fragment was inserted to the retrovirus vector pMX-IRES-GFP in the same manner as described in (1) of Example 2.

```
SCR-7FSalI
acgcgtcgacccaccATGCCCCGCTACGAGTTG      (SEQ ID NO: 43)

SCR-7Reco
attGAATTCTCACTTCTTCCTCCTCTTTG          (SEQ ID NO: 44)
```

(2) Preparation of Stromal Cells Highly Expressing SCR-7

AGM-s3-A9 cells in which SCR-7 was highly expressed were prepared by using the above retrovirus vector in the same manner as (2) of Example 2.

(3) Co-Culture of Human Hematopoietic Stem Cells and Stromal Cells Highly Expressing SCR-7, and Determination of Proliferation Statuses of Hematopoietic Stem Cells and Hematopoietic Progenitor Cells by Clonogenic Assay In the same manner as described in (III) (1) 3) to 4) of Example 1, AGM-s3-A9 cells in which SCR-7 was highly expressed through retrovirus, AGM-s3-A9 cells into which a control vector was introduced, or AGM-s3-A9 cells were co-cultured with CD34-positive hematopoietic stem cells derived from human cord blood, and proliferation statuses of hematopoietic stem cells and hematopoietic progenitor cells are determined.

Figure 10:
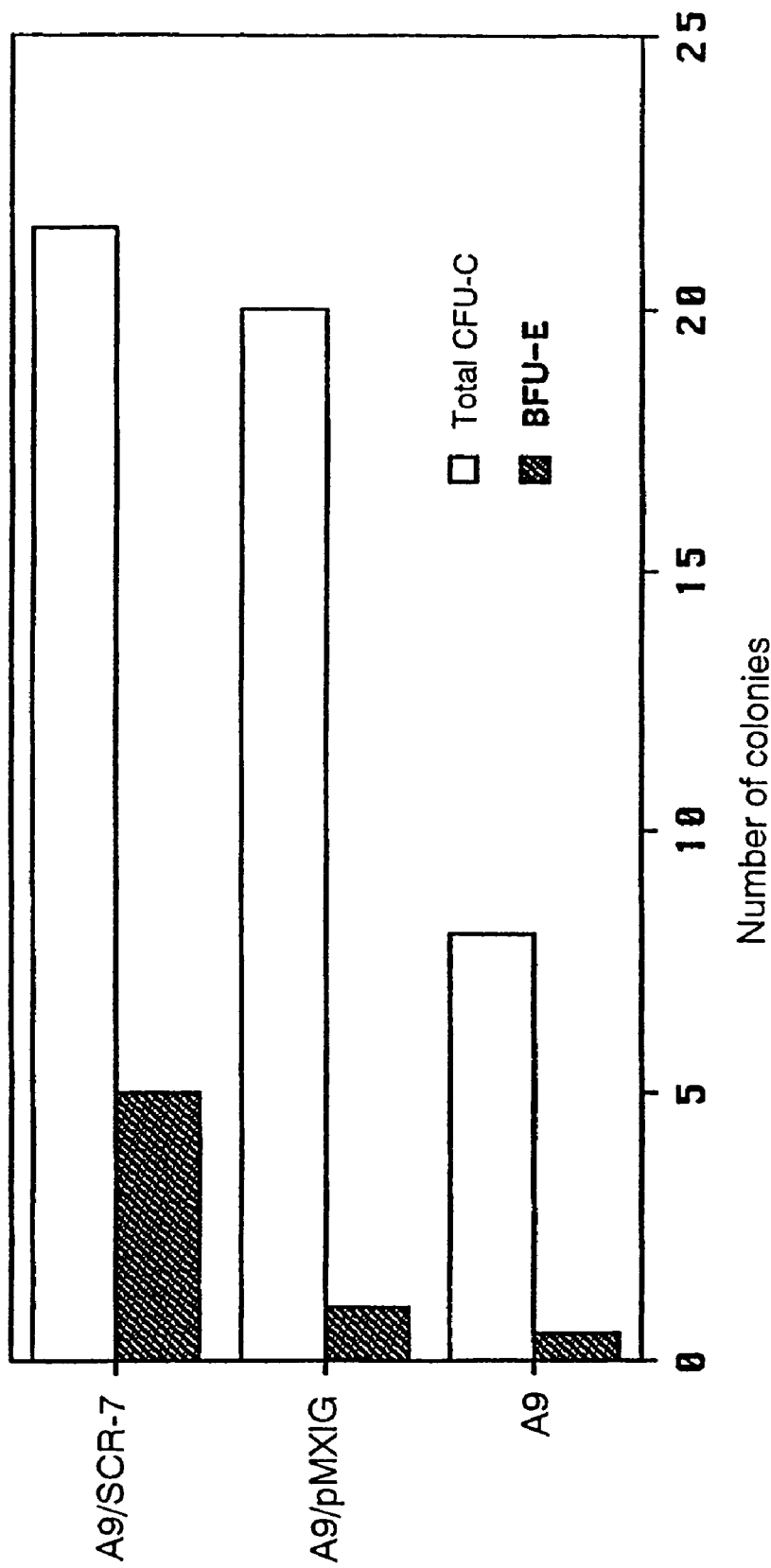
FIG. 10 shows proliferation statuses of hematopoietic stem cells and hematopoietic progenitor cells determined by a clonogenic assay after co-culture of CD34-positive hematopoietic stem cells with AGM-S3-A9 cells in which a gene SCR-7 is highly expressed (A9/SCR-7), AGM-S3-A9 cells into which a control vector is introduced (A9/pMXIG) or AGM-S3-A9 cells (A9) for two weeks.

FIG. 10 shows results when the CD34-positive hematopoietic stem cells were co-cultured with AGM-S3-A9 cells in which SCR-0.7 was highly expressed (A9/SCR-7), AGM-S3-A9 cells into which a control vector was introduced (A9/ pMXIG) or AGM-S3-A9 cells (A9) for two weeks. As a result, the co-culture with AGM-S3-A9 cells in which SCR-7 was highly expressed, increases of BFU-E and CFU-C were observed. Therefore, it has been revealed that the activity to support hematopoietic stem cells or hematopoietic progenitor cells, of AGM-S3-A9 increases by allowing SCR-7 to be highly expressed. From the results, it has been revealed that the gene product of SCR-7 has an activity to support survival or proliferation of hematopoietic stem cells or hematopoietic progenitor cells or an activity to affect stromal cells to enhance a hematopoietic cell-supporting activity of the stromal cells or impart the activity to the stromal cells.

EXAMPLE 8

Cloning of SCR-8 and Activity Determination

By searching GenBank database for the nucleotide sequence shown in SEQ ID NO: 7 with BLAST, it has been found that SCR-8 is the same gene as *Mus musculus* mRNA for ADAM23 of an accession number AB009673. The nuclotide sequence of SCR-8 ORF and the amino acid sequence deduced from the nucleotide sequence are shown in SEQ ID NO: 26. Only the amino acid sequence is shown in SEQ ID NO: 27.

Also, the sequence encoding Human MDC3 protein [*Homo sapiens*] described by JP 11155574-A has a homology of not less than 90% with SCR-8 and, therefore, is a human ortholog of SCR-8. The nucleotide sequence of this ORF and the amino acid sequence deduced from the nucleotide sequence are shown in SEQ ID NO: 28. Only the amino acid sequence is shown in SEQ ID NO: 29.

Determination of the activity of SCR-8 to support the hematopoietic stem cells or hematopoietic progenitor cells was performed as follows.

(1) Construction of Retrovirus Vector for Expression of Mouse SCR-8

Based on the nucleotide sequence of SCR-8 ORF, SCR-8FxhoI and SCR-8Reco primers having the following nucleotide sequences were prepared, and PCR was performed using AGM-s3-A9 cDNA as a template. An amplified fragment was inserted to the retrovirus vector pMX-IRES-GFP in the same manner as described in (1) of Example 2.

```
SCR-8FxhoI                                    (SEQ ID NO: 45)
ccgctcgagccaccATGAAGCCGCCCGGCAGCATC SCR-8Reco                                     (SEQ ID NO: 46)
cggaattcTCAGATGGGGCCTTGCTGAGT
```

(2) Preparation of Stromal Cells Highly Expressing SCR-8

AGM-s3-A9 cells in which SCR-8 was highly expressed were prepared by using the above retrovirus vector in the same manner as (2) of Example 2.

(3) Co-Culture of Human Hematopoietic Stem Cells and Stromal Cells Highly Expressing SCR-8, and Determination of Proliferation Statuses of Hematopoietic Stem Cells and Hematopoietic Progenitor Cells by Clonogenic Assay In the same manner as described in (III) (1) 3) to 4) of Example 1, AGM-s3-A9 cells in which SCR-8 was highly expressed through retrovirus, AGM-s3-A9 cells into which a control vector was introduced, or AGM-s3-A9 cells were co-cultured with CD34-positive hematopoietic stem cells derived from human cord blood, and proliferation statuses of hematopoietic stem cells and hematopoietic progenitor cells are determined.

Figure 11:
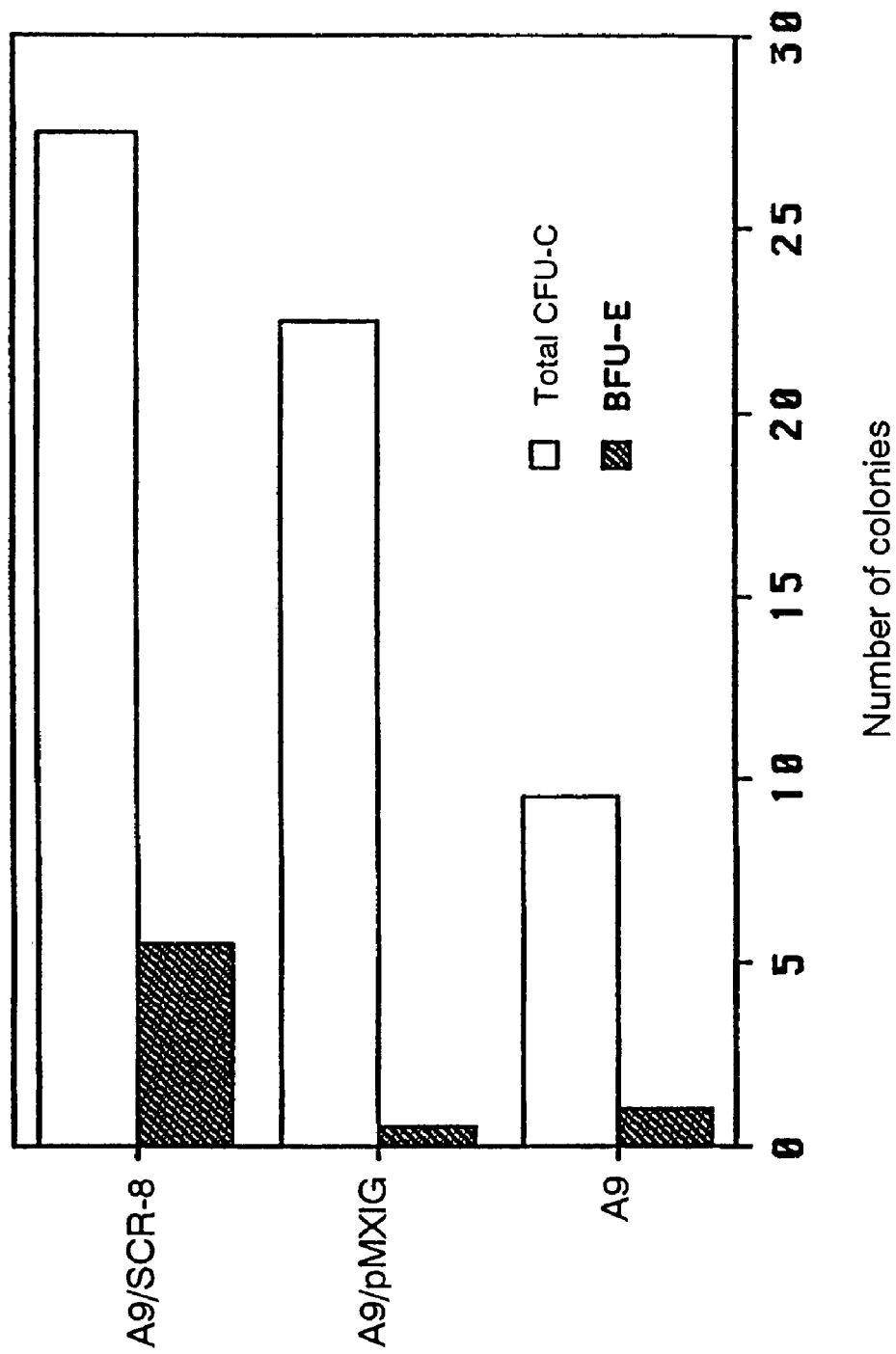
FIG. 11 shows proliferation statuses of hematopoietic stem cells and hematopoietic progenitor cells determined by a clonogenic assay after co-culture of CD34-positive hematopoietic stem cells with AGM-S3-A9 cells in which a gene SCR-8 is highly expressed (A9/SCR-8), AGM-S3-A9 cells into which a control vector is introduced (A9/pMXIG) or AGM-S3-A9 cells (A9) for two weeks.

FIG. 11 shows results when the CD34-positive hematopoietic stem cells were co-cultured with AGM-S3-A9 cells in which SCR-8 was highly expressed, AGM-S3-A9 cells into which a control vector was introduced or AGM-S3-A9 cells for two weeks. As a result, the co-culture with AGM-S3-A9 cells in which SCR-8 was highly expressed, increases of BFU-E and CFU-C were observed. Therefore, it has been revealed that the activity to support hematopoietic stem cells or hematopoietic progenitor cells, of AGM-S3-A9 increases by allowing SCR-8 to be highly expressed. From the results, it has been revealed that the gene product of SCR-8 has an activity to support survival or proliferation of hematopoietic stem cells or hematopoietic progenitor cells or an activity to affect stromal cells to enhance a hematopoietic cell-supporting activity of the stromal cells or impart the activity to the stromal cells.

What is claimed is:

1. An isolated polypeptide which is an expression product of the nucleic acid of SEQ ID NO: 47, wherein the polypeptide has an activity to support proliferation of erythroid progenitor cells.

2. The polypeptide according to claim 1, comprising the amino acid sequence of SEQ ID NO: 48.

3. The polypeptide according to claim 1, which is modified with one or more modifying agents selected from the group consisting of polyethylene glycol (PEG), dextran, poly(N-vinyl-pyrrolidone), polypropylene glycol homopolymer, copolymer of polypropylene oxide/ethylene oxide, polyoxyethylated polyol and polyvinyl alcohol.

4. A composition having an effect to support proliferation of erythroid progenitor cells, comprising an effective amount of a polypeptide according to any one of claims 1 to 3.

* * * * *